(12) United States Patent
Connor

(10) Patent No.: US 9,011,365 B2
(45) Date of Patent: Apr. 21, 2015

(54) ADJUSTABLE GASTROINTESTINAL BIFURCATION (AGB) FOR REDUCED ABSORPTION OF UNHEALTHY FOOD

(71) Applicant: Robert A. Connor, Forest Lake, MN (US)

(72) Inventor: Robert A. Connor, Forest Lake, MN (US)

(73) Assignee: Medibotics LLC, Forest Lake, MN (US)

( * ) Notice: Subject to any disclaimer, the term of this patent is extended or adjusted under 35 U.S.C. 154(b) by 52 days.

(21) Appl. No.: 13/797,966

(22) Filed: Mar. 12, 2013

(65) Prior Publication Data

US 2014/0275747 A1  Sep. 18, 2014

(51) Int. Cl.
*A61M 5/00* (2006.01)
*A61F 5/00* (2006.01)

(52) U.S. Cl.
CPC .................... *A61F 5/0076* (2013.01)

(58) Field of Classification Search
CPC ... A61F 5/0076; A61F 5/0079; A61F 5/0003; A61F 5/0036; A61F 5/004
USPC ............ 604/8–9, 540, 318; 623/23.64, 23.65, 623/23.68; 600/37
See application file for complete search history.

(56) References Cited

U.S. PATENT DOCUMENTS

| | | | |
|---|---|---|---|
| 3,411,507 A | 11/1968 | Wingrove | |
| 3,818,906 A | 6/1974 | Stubbs | |
| 3,856,942 A | 12/1974 | Murphy | |
| 3,885,576 A | 5/1975 | Symmes | |
| 3,911,099 A | 10/1975 | Defoney et al. | |
| 3,972,995 A | 8/1976 | Tsuk et al. | |
| 4,039,653 A | 8/1977 | Defoney et al. | |
| 4,059,686 A | 11/1977 | Tanaka et al. | |
| 4,075,769 A | 2/1978 | Young | |
| 4,100,401 A | 7/1978 | Tutt et al. | |
| 4,133,315 A | 1/1979 | Berman et al. | |
| 4,159,347 A | 6/1979 | Yoshida et al. | |
| 4,207,673 A | 6/1980 | DiGirolamo et al. | |
| 4,210,637 A | 7/1980 | Wurtman et al. | |
| 4,212,079 A | 7/1980 | Segar et al. | |
| 4,218,611 A | 8/1980 | Cannon | |
| 4,221,959 A | 9/1980 | Sessler | |
| 4,292,299 A | 9/1981 | Suzuki et al. | |
| 4,310,316 A | 1/1982 | Thomann | |
| 4,321,674 A | 3/1982 | Krames et al. | |
| 4,355,645 A | 10/1982 | Mitani et al. | |
| 4,387,777 A | 6/1983 | Ash | |
| 4,416,267 A | 11/1983 | Garren et al. | |
| 4,471,771 A | 9/1984 | Brown | |

(Continued)

FOREIGN PATENT DOCUMENTS

WO   WO 2006/014496   7/2005

*Primary Examiner* — Philip R Wiest
*Assistant Examiner* — Ariana Zimbouski

(57) ABSTRACT

This invention is a device and method for adjustably and reversibly reducing nutrient absorption from food passing through a person's gastrointestinal tract using an Adjustable Gastrointestinal Bifurcation (AGB) and a flow-control member. The Adjustable Gastrointestinal Bifurcation (AGB) includes: a first food-flow route (comprising a first branch of the AGB) through the person's gastrointestinal tract wherein there is normal absorption of nutrients from food; and a second food-flow route (comprising a second branch of the AGB) through the person's gastrointestinal tract wherein there is reduced absorption of nutrients from food. The flow-control member adjusts the types and/or amounts of food which are diverted through the second food-flow route versus the first food-flow route.

19 Claims, 9 Drawing Sheets

(56) References Cited

U.S. PATENT DOCUMENTS

| | | | |
|---|---|---|---|
| 4,491,578 A | 1/1985 | Peikin | |
| 4,497,798 A | 2/1985 | Lambert | |
| 4,519,400 A | 5/1985 | Brenman et al. | |
| 4,582,492 A | 4/1986 | Etter et al. | |
| 4,592,339 A | 6/1986 | Kuzmak et al. | |
| 4,615,697 A | 10/1986 | Robinson | |
| 4,637,405 A | 1/1987 | Brenman et al. | |
| 4,641,653 A | 2/1987 | Rockey | |
| 4,650,218 A | 3/1987 | Hawke | |
| 4,686,624 A | 8/1987 | Blum et al. | |
| 4,689,235 A | 8/1987 | Barnes et al. | |
| 4,694,827 A | 9/1987 | Weiner et al. | |
| 4,738,259 A | 4/1988 | Brown et al. | |
| 4,740,365 A | 4/1988 | Yukimatsu et al. | |
| 4,764,378 A | 8/1988 | Keith et al. | |
| 4,796,182 A | 1/1989 | Duboff | |
| 4,822,597 A | 4/1989 | Faust et al. | |
| 4,823,808 A | 4/1989 | Clegg et al. | |
| 4,875,533 A | 10/1989 | Mihara et al. | |
| 4,911,256 A | 3/1990 | Attikiouzel | |
| 4,914,819 A | 4/1990 | Ash | |
| 4,925,446 A | 5/1990 | Garay et al. | |
| 4,935,225 A | 6/1990 | Curtis et al. | |
| 4,951,197 A | 8/1990 | Mellinger | |
| 4,965,553 A | 10/1990 | DelBiondo et al. | |
| 4,975,682 A | 12/1990 | Kerr et al. | |
| 5,011,472 A | 4/1991 | Aebischer et al. | |
| 5,013,716 A | 5/1991 | Cherukuri et al. | |
| 5,033,561 A | 7/1991 | Hettinger | |
| 5,067,488 A | 11/1991 | Fukada et al. | |
| 5,074,868 A | 12/1991 | Kuzmak | |
| 5,173,588 A | 12/1992 | Harrah | |
| 5,188,104 A | 2/1993 | Wernicke et al. | |
| 5,194,003 A | 3/1993 | Garay et al. | |
| 5,226,429 A | 7/1993 | Kuzmak | |
| 5,233,520 A | 8/1993 | Kretsch et al. | |
| 5,234,454 A | 8/1993 | Bangs | |
| 5,259,399 A * | 11/1993 | Brown | 128/897 |
| 5,263,480 A | 11/1993 | Wernicke et al. | |
| 5,263,491 A | 11/1993 | Thornton | |
| 5,284,132 A | 2/1994 | Geier | |
| 5,290,808 A | 3/1994 | Sofia | |
| 5,292,344 A | 3/1994 | Douglas | |
| 5,299,356 A | 4/1994 | Maxwell | |
| 5,301,679 A | 4/1994 | Taylor | |
| 5,318,519 A | 6/1994 | Wilk | |
| 5,388,043 A | 2/1995 | Hettinger | |
| 5,398,688 A | 3/1995 | Laniado | |
| 5,405,641 A | 4/1995 | Kurihara et al. | |
| 5,412,564 A | 5/1995 | Ecer | |
| 5,421,089 A | 6/1995 | Dubus et al. | |
| 5,423,872 A | 6/1995 | Cigaina | |
| 5,424,719 A | 6/1995 | Ravid | |
| 5,449,368 A | 9/1995 | Kuzmak | |
| 5,456,677 A | 10/1995 | Spector | |
| 5,472,685 A | 12/1995 | Gaffar | |
| 5,478,989 A | 12/1995 | Shepley | |
| 5,497,772 A | 3/1996 | Schulman et al. | |
| 5,540,730 A | 7/1996 | Terry et al. | |
| 5,542,420 A | 8/1996 | Goldman et al. | |
| 5,563,850 A | 10/1996 | Hanapole | |
| 5,601,604 A | 2/1997 | Vincent | |
| 5,603,971 A | 2/1997 | Porzio et al. | |
| 5,605,698 A | 2/1997 | Ueno | |
| 5,643,207 A | 7/1997 | Rise | |
| 5,673,691 A | 10/1997 | Abrams et al. | |
| 5,690,691 A | 11/1997 | Chen et al. | |
| 5,691,927 A | 11/1997 | Gump | |
| 5,704,350 A | 1/1998 | Williams | |
| 5,716,385 A | 2/1998 | Mittal et al. | |
| 5,720,771 A | 2/1998 | Snell | |
| 5,729,479 A | 3/1998 | Golan | |
| 5,730,722 A | 3/1998 | Wilk | |
| 5,782,798 A | 7/1998 | Rise | |
| 5,792,210 A | 8/1998 | Wamubu et al. | |
| 5,795,304 A | 8/1998 | Sun et al. | |
| 5,817,006 A | 10/1998 | Bergh et al. | |
| 5,819,735 A | 10/1998 | Mansfield et al. | |
| 5,836,312 A | 11/1998 | Moore | |
| 5,836,994 A | 11/1998 | Bourgeois | |
| 5,839,901 A | 11/1998 | Karkanen | |
| 5,841,115 A | 11/1998 | Shepley | |
| 5,858,967 A | 1/1999 | Weigle et al. | |
| 5,861,014 A | 1/1999 | Familoni | |
| 5,868,141 A | 2/1999 | Ellias | |
| 5,890,128 A | 3/1999 | Diaz et al. | |
| 5,891,185 A | 4/1999 | Freed et al. | |
| 5,908,301 A | 6/1999 | Lutz | |
| 5,924,422 A | 7/1999 | Gustafson | |
| 5,942,244 A | 8/1999 | Friedman et al. | |
| 5,979,449 A | 11/1999 | Steer | |
| 5,989,188 A | 11/1999 | Birkhoelzer | |
| 5,993,473 A | 11/1999 | Chan et al. | |
| 5,995,872 A | 11/1999 | Bourgeois | |
| 6,024,281 A | 2/2000 | Shepley | |
| 6,032,676 A | 3/2000 | Moore | |
| 6,040,531 A | 3/2000 | Miller-Kovach | |
| 6,067,991 A | 5/2000 | Forsell | |
| 6,083,006 A | 7/2000 | Coffman | |
| 6,083,249 A | 7/2000 | Familoni | |
| 6,091,992 A | 7/2000 | Bourgeois et al. | |
| 6,093,167 A | 7/2000 | Houben et al. | |
| 6,095,949 A | 8/2000 | Arai | |
| 6,104,955 A | 8/2000 | Bourgeois | |
| 6,112,749 A | 9/2000 | Hall et al. | |
| 6,115,635 A | 9/2000 | Bourgeois | |
| 6,123,980 A | 9/2000 | Pearson et al. | |
| 6,135,950 A | 10/2000 | Adams | |
| 6,145,503 A | 11/2000 | Smith | |
| 6,154,676 A | 11/2000 | Levine | |
| 6,159,145 A | 12/2000 | Satoh | |
| 6,183,775 B1 | 2/2001 | Ventouras | |
| 6,185,452 B1 | 2/2001 | Schulman et al. | |
| 6,207,638 B1 | 3/2001 | Portman | |
| 6,216,039 B1 | 4/2001 | Bourgeois | |
| 6,218,358 B1 | 4/2001 | Firestein et al. | |
| 6,224,873 B1 | 5/2001 | Jones | |
| 6,230,052 B1 | 5/2001 | Wolff et al. | |
| 6,235,274 B1 | 5/2001 | Lou et al. | |
| 6,243,607 B1 | 6/2001 | Mintchev et al. | |
| 6,248,390 B1 | 6/2001 | Stillman | |
| 6,280,761 B1 | 8/2001 | Santus | |
| 6,283,914 B1 | 9/2001 | Mansfield et al. | |
| 6,285,897 B1 | 9/2001 | Kilcoyne et al. | |
| 6,319,523 B1 | 11/2001 | Zhou | |
| 6,327,503 B1 | 12/2001 | Familoni | |
| 6,334,073 B1 | 12/2001 | Levine | |
| 6,336,136 B1 | 1/2002 | Harris | |
| 6,341,295 B1 | 1/2002 | Stotler | |
| 6,365,128 B1 | 4/2002 | Bennett-Guerrero | |
| 6,376,657 B1 | 4/2002 | Van Heerden et al. | |
| 6,387,329 B1 | 5/2002 | Lewis et al. | |
| 6,387,408 B1 | 5/2002 | Illum et al. | |
| 6,413,545 B1 | 7/2002 | Alviar et al. | |
| 6,419,903 B1 | 7/2002 | Xu et al. | |
| 6,422,243 B1 | 7/2002 | Daram | |
| 6,425,862 B1 | 7/2002 | Brown | |
| 6,454,785 B2 | 9/2002 | De Hoyos Garza | |
| 6,473,368 B1 | 10/2002 | Stanfield | |
| 6,478,736 B1 | 11/2002 | Mault | |
| 6,485,710 B2 | 11/2002 | Zuckerman | |
| 6,488,953 B2 | 12/2002 | Halliday et al. | |
| 6,506,152 B1 | 1/2003 | Lackey et al. | |
| 6,508,762 B2 | 1/2003 | Karnieli | |
| 6,513,532 B2 | 2/2003 | Mault et al. | |
| 6,535,764 B2 | 3/2003 | Imran et al. | |
| 6,547,801 B1 | 4/2003 | Dargent et al. | |
| 6,551,235 B2 | 4/2003 | Forsell | |
| 6,553,386 B1 | 4/2003 | Alabaster | |
| 6,558,400 B2 | 5/2003 | Deem et al. | |
| 6,564,101 B1 | 5/2003 | Zikria | |
| 6,571,127 B1 | 5/2003 | Ben-Haim et al. | |
| 6,571,200 B1 | 5/2003 | Mault | |
| 6,572,629 B2 | 6/2003 | Kalloo et al. | |

(56) References Cited

U.S. PATENT DOCUMENTS

| | | |
|---|---|---|
| 6,579,301 B1 | 6/2003 | Bales et al. |
| 6,587,719 B1 | 7/2003 | Barrett et al. |
| 6,591,137 B1 | 7/2003 | Fischell et al. |
| 6,595,929 B2 | 7/2003 | Stivoric et al. |
| 6,600,953 B2 | 7/2003 | Flesler et al. |
| 6,605,038 B1 | 8/2003 | Teller et al. |
| 6,609,025 B2 | 8/2003 | Barrett et al. |
| 6,610,277 B2 | 8/2003 | Zuckerman |
| 6,610,367 B2 | 8/2003 | Lewis et al. |
| 6,627,206 B2 | 9/2003 | Lloyd |
| 6,635,015 B2 | 10/2003 | Sagel |
| 6,675,041 B2 | 1/2004 | Dickinson |
| 6,675,809 B1 | 1/2004 | Stack et al. |
| 6,684,104 B2 | 1/2004 | Gordon et al. |
| 6,694,182 B1 | 2/2004 | Yamazaki et al. |
| 6,715,485 B1 | 4/2004 | Djupesland |
| 6,733,512 B2 | 5/2004 | Mcghan |
| 6,735,477 B2 | 5/2004 | Levine |
| 6,735,479 B2 | 5/2004 | Fabian et al. |
| 6,745,214 B2 | 6/2004 | Inoue et al. |
| 6,760,626 B1 | 7/2004 | Boveja |
| 6,765,488 B2 | 7/2004 | Stanfield |
| 6,826,428 B1 | 11/2004 | Chen et al. |
| 6,832,114 B1 | 12/2004 | Whitehurst et al. |
| 6,856,938 B2 | 2/2005 | Kurtz |
| 6,861,405 B2 | 3/2005 | Desir et al. |
| 6,878,885 B2 | 4/2005 | Miller-Kovach |
| 6,879,859 B1 | 4/2005 | Boveja |
| 6,893,406 B2 | 5/2005 | Takeuchi et al. |
| 6,893,654 B2 | 5/2005 | Pinney et al. |
| 6,902,751 B1 | 6/2005 | Schleifenbaum et al. |
| 6,917,897 B2 | 7/2005 | Mork |
| 6,922,590 B1 | 7/2005 | Whitehurst |
| 6,942,848 B2 | 9/2005 | Nelson et al. |
| 6,949,264 B1 | 9/2005 | Mcgrew et al. |
| 6,950,707 B2 | 9/2005 | Whitehurst |
| 6,966,875 B1 | 11/2005 | Longobardi |
| 6,981,980 B2 | 1/2006 | Sampson et al. |
| 6,993,391 B2 | 1/2006 | Flesler et al. |
| 7,006,871 B1 | 2/2006 | Darvish et al. |
| 7,020,508 B2 | 3/2006 | Stivoric et al. |
| 7,020,531 B1 | 3/2006 | Colliou et al. |
| 7,025,984 B1 | 4/2006 | Jandacek et al. |
| 7,033,373 B2 | 4/2006 | DeLaTorre et al. |
| 7,037,343 B2 | 5/2006 | Imran |
| 7,037,344 B2 | 5/2006 | Kagan et al. |
| 7,041,311 B2 | 5/2006 | Grainger et al. |
| 7,043,295 B2 | 5/2006 | Starkebaum |
| 7,044,739 B2 | 5/2006 | Matson |
| 7,054,690 B2 | 5/2006 | Imran |
| 7,066,945 B2 | 6/2006 | Hashiba et al. |
| 7,072,720 B2 | 7/2006 | Puskas |
| 7,076,305 B2 | 7/2006 | Imran et al. |
| 7,108,680 B2 | 9/2006 | Rohr et al. |
| 7,112,186 B2 | 9/2006 | Shah |
| 7,115,297 B2 | 10/2006 | Stillman |
| 7,120,498 B2 | 10/2006 | Imran et al. |
| 7,121,283 B2 | 10/2006 | Stack et al. |
| 7,122,152 B2 | 10/2006 | Lewis et al. |
| 7,138,107 B2 | 11/2006 | Adams et al. |
| 7,141,071 B2 | 11/2006 | Imran |
| 7,152,607 B2 | 12/2006 | Stack et al. |
| 7,167,750 B2 | 1/2007 | Knudson et al. |
| 7,177,693 B2 | 2/2007 | Starkebaum |
| 7,220,284 B2 | 5/2007 | Kagan et al. |
| 7,229,658 B1 | 6/2007 | Inoue et al. |
| 7,236,822 B2 | 6/2007 | Dobak |
| 7,238,380 B2 | 7/2007 | Stillman |
| 7,239,912 B2 | 7/2007 | Dobak |
| 7,241,880 B2 | 7/2007 | Adler et al. |
| 7,247,023 B2 | 7/2007 | Peplinski et al. |
| 7,247,323 B2 | 7/2007 | George et al. |
| 7,261,690 B2 | 8/2007 | Teller et al. |
| 7,276,229 B1 | 10/2007 | Baker et al. |
| 7,285,090 B2 | 10/2007 | Stivoric et al. |
| 7,288,099 B2 | 10/2007 | Deem et al. |
| 7,288,101 B2 | 10/2007 | Deem et al. |
| 7,299,091 B2 | 11/2007 | Barrett et al. |
| 7,330,753 B2 | 2/2008 | Policker et al. |
| 7,354,454 B2 | 4/2008 | Stack et al. |
| 7,361,141 B2 | 4/2008 | Nissila et al. |
| 7,402,400 B2 | 7/2008 | Zuker et al. |
| 7,409,647 B2 | 8/2008 | Elber et al. |
| 7,430,450 B2 | 9/2008 | Imran |
| 7,437,195 B2 | 10/2008 | Policker et al. |
| 7,440,806 B1 | 10/2008 | Whitehurst et al. |
| 7,454,002 B1 | 11/2008 | Gardner et al. |
| 7,470,251 B2 | 12/2008 | Shah |
| 7,477,944 B1 | 1/2009 | Whitehurst et al. |
| 7,477,947 B2 | 1/2009 | Pines et al. |
| 7,483,746 B2 | 1/2009 | Lee et al. |
| 7,493,171 B1 | 2/2009 | Whitehurst et al. |
| 7,500,937 B2 | 3/2009 | Hercules |
| 7,502,649 B2 | 3/2009 | Ben-Haim et al. |
| 7,503,922 B2 | 3/2009 | Deem et al. |
| 7,509,174 B2 | 3/2009 | Imran et al. |
| 7,510,559 B2 | 3/2009 | Deem et al. |
| 7,512,442 B2 | 3/2009 | Flesler et al. |
| 7,524,877 B2 | 4/2009 | Rosenfeld et al. |
| 7,529,582 B1 | 5/2009 | Dilorenzo |
| 7,541,356 B2 | 6/2009 | Rosenfeld et al. |
| 7,551,964 B2 | 6/2009 | Dobak |
| 7,558,629 B2 | 7/2009 | Keimel et al. |
| 7,580,751 B2 | 8/2009 | Starkebaum |
| 7,590,452 B2 | 9/2009 | Imran et al. |
| 7,595,023 B2 | 9/2009 | Lewis et al. |
| 7,599,736 B2 | 10/2009 | Dilorenzo |
| 7,601,178 B2 | 10/2009 | Imran |
| 7,620,454 B2 | 11/2009 | Dinsmoor et al. |
| 7,632,517 B2 | 12/2009 | Dugger et al. |
| 7,643,887 B2 | 1/2010 | Imran |
| 7,648,479 B2 | 1/2010 | Solovay et al. |
| 7,651,868 B2 | 1/2010 | Mcdevitt et al. |
| 7,657,310 B2 | 2/2010 | Buras |
| 7,664,551 B2 | 2/2010 | Cigaina |
| 7,682,306 B2 | 3/2010 | Shah |
| 7,689,276 B2 | 3/2010 | Dobak |
| 7,689,277 B2 | 3/2010 | Dobak |
| 7,689,437 B1 | 3/2010 | Teller et al. |
| 7,695,446 B2 | 4/2010 | Levine et al. |
| 7,699,863 B2 | 4/2010 | Marco et al. |
| 7,702,386 B2 | 4/2010 | Dobak et al. |
| 7,702,394 B2 | 4/2010 | Imran |
| 7,717,843 B2 | 5/2010 | Balbierz et al. |
| 7,727,147 B1 | 6/2010 | Osorio et al. |
| 7,727,546 B2 | 6/2010 | Moneymaker et al. |
| 7,729,771 B2 | 6/2010 | Knudson et al. |
| 7,738,961 B2 | 6/2010 | Sharma |
| 7,740,624 B2 | 6/2010 | Klein et al. |
| 7,742,818 B2 | 6/2010 | Dinsmoor et al. |
| 7,753,870 B2 | 7/2010 | Demarais et al. |
| 7,756,582 B2 | 7/2010 | Imran et al. |
| 7,758,493 B2 | 7/2010 | Gingras |
| 7,769,635 B2 | 8/2010 | Simons-Nikolova |
| 7,771,382 B2 | 8/2010 | Levine et al. |
| 7,775,966 B2 | 8/2010 | Dlugos et al. |
| 7,775,967 B2 | 8/2010 | Gertner |
| 7,785,291 B2 | 8/2010 | Marco et al. |
| 7,790,671 B2 | 9/2010 | Stojanovic-Susulic |
| 7,794,425 B2 | 9/2010 | Gobel |
| 7,794,447 B2 | 9/2010 | Dann et al. |
| 7,798,954 B2 | 9/2010 | Birk et al. |
| 7,803,195 B2 | 9/2010 | Levy et al. |
| 7,815,629 B2 | 10/2010 | Klein et al. |
| 7,820,208 B2 | 10/2010 | Hirsch |
| 7,832,407 B2 | 11/2010 | Gertner |
| 7,833,279 B2 | 11/2010 | Knudson et al. |
| 7,833,280 B2 | 11/2010 | Stack et al. |
| 7,835,796 B2 | 11/2010 | Maschino et al. |
| 7,837,643 B2 | 11/2010 | Levine et al. |
| 7,837,669 B2 | 11/2010 | Dann et al. |
| 7,840,269 B2 | 11/2010 | Policker et al. |
| 7,840,278 B1 | 11/2010 | Puskas |
| 7,841,978 B2 | 11/2010 | Gertner |

(56) References Cited

U.S. PATENT DOCUMENTS

| | | |
|---|---|---|
| 7,846,138 B2 | 12/2010 | Dann et al. |
| 7,851,000 B2 | 12/2010 | Boghani et al. |
| 7,851,005 B2 | 12/2010 | Bingley et al. |
| 7,851,006 B2 | 12/2010 | Bingley et al. |
| 7,854,745 B2 | 12/2010 | Brister et al. |
| 7,857,730 B2 | 12/2010 | Dugan |
| 7,862,574 B2 | 1/2011 | Deem et al. |
| 7,879,068 B2 | 2/2011 | Dlugos et al. |
| 7,879,376 B2 | 2/2011 | Boghani et al. |
| 7,881,797 B2 | 2/2011 | Griffin et al. |
| 7,882,150 B2 | 2/2011 | Badyal |
| 7,909,754 B2 | 3/2011 | Hassler et al. |
| 7,909,838 B2 | 3/2011 | Deem et al. |
| 7,909,839 B2 | 3/2011 | Fields |
| 7,914,468 B2 | 3/2011 | Shalon et al. |
| 7,931,694 B2 | 4/2011 | Imran |
| 7,935,065 B2 | 5/2011 | Martin et al. |
| 7,935,073 B2 | 5/2011 | Levine et al. |
| 7,937,145 B2 | 5/2011 | Dobak |
| 7,938,769 B2 | 5/2011 | Gertner |
| 7,941,221 B2 | 5/2011 | Foley |
| 7,945,323 B2 | 5/2011 | Jaax et al. |
| 7,949,506 B1 | 5/2011 | Hill et al. |
| 7,959,567 B2 | 6/2011 | Stivoric et al. |
| 7,963,907 B2 | 6/2011 | Gertner |
| 7,967,780 B2 | 6/2011 | Goebel |
| 7,972,346 B2 | 7/2011 | Bachmann et al. |
| 7,972,618 B2 | 7/2011 | Fuisz et al. |
| 7,974,672 B2 | 7/2011 | Shults et al. |
| 7,977,060 B2 | 7/2011 | Zuker et al. |
| 7,979,127 B2 | 7/2011 | Imran |
| 7,981,162 B2 | 7/2011 | Stack et al. |
| 7,986,995 B2 | 7/2011 | Knudson et al. |
| 7,988,617 B2 | 8/2011 | Gertner |
| 7,988,630 B1 | 8/2011 | Osorio et al. |
| 7,999,674 B2 | 8/2011 | Kamen |
| 8,001,974 B2 | 8/2011 | Makower et al. |
| 8,002,758 B2 | 8/2011 | Kamen et al. |
| 8,010,204 B2 | 8/2011 | Knudson et al. |
| 8,012,140 B1 | 9/2011 | Kagan et al. |
| 8,016,744 B2 | 9/2011 | Dlugos et al. |
| 8,016,745 B2 | 9/2011 | Hassler et al. |
| 8,019,421 B2 | 9/2011 | Darvish et al. |
| 8,029,455 B2 | 10/2011 | Stack et al. |
| 8,034,065 B2 | 10/2011 | Coe et al. |
| 8,034,118 B2 | 10/2011 | Imran |
| 8,043,206 B2 | 10/2011 | Birk |
| 8,048,169 B2 | 11/2011 | Burnett et al. |
| 8,057,420 B2 | 11/2011 | Meade et al. |
| 8,060,220 B2 | 11/2011 | Liebergesell et al. |
| 8,062,285 B2 | 11/2011 | Langloss et al. |
| 8,066,689 B2 | 11/2011 | Mitelberg et al. |
| 8,066,780 B2 | 11/2011 | Chen et al. |
| 8,067,185 B2 | 11/2011 | Zoller et al. |
| 8,070,673 B2 | 12/2011 | Gertner et al. |
| 8,070,743 B2 | 12/2011 | Kagan et al. |
| 8,070,768 B2 | 12/2011 | Kim et al. |
| 8,073,707 B2 | 12/2011 | Teller et al. |
| 8,075,451 B2 | 12/2011 | Dugan |
| 8,075,577 B2 | 12/2011 | Deem et al. |
| 8,080,022 B2 | 12/2011 | Deem et al. |
| 8,080,025 B2 | 12/2011 | Deem et al. |
| 8,082,039 B2 | 12/2011 | Kim et al. |
| 8,083,756 B2 | 12/2011 | Gannoe et al. |
| 8,083,757 B2 | 12/2011 | Gannoe et al. |
| 8,087,937 B2 | 1/2012 | Peplinski et al. |
| 8,095,218 B2 | 1/2012 | Gross et al. |
| 8,095,219 B2 | 1/2012 | Lee et al. |
| 8,100,870 B2 | 1/2012 | Marcotte et al. |
| 8,109,895 B2 | 2/2012 | Williams et al. |
| 8,109,920 B2 | 2/2012 | Boyden et al. |
| 8,112,281 B2 | 2/2012 | Yeung et al. |
| 8,119,359 B2 | 2/2012 | Adler et al. |
| 8,123,765 B2 | 2/2012 | Deem et al. |
| 8,135,470 B2 | 3/2012 | Keimel et al. |
| 8,137,261 B2 | 3/2012 | Kierath et al. |
| 8,137,301 B2 | 3/2012 | Levine et al. |
| 8,137,366 B2 | 3/2012 | Deem et al. |
| 8,137,367 B2 | 3/2012 | Deem et al. |
| 8,142,469 B2 | 3/2012 | Sosnowski et al. |
| 8,142,513 B2 | 3/2012 | Shalon et al. |
| 8,143,062 B2 | 3/2012 | Hirsch |
| 8,143,215 B2 | 3/2012 | Hirsch |
| 8,145,299 B2 | 3/2012 | Dobak |
| 8,147,441 B2 | 4/2012 | Gannoe et al. |
| 8,150,508 B2 | 4/2012 | Craig |
| 8,157,731 B2 | 4/2012 | Teller et al. |
| 8,158,082 B2 | 4/2012 | Imran |
| 8,162,871 B2 | 4/2012 | Levine et al. |
| 8,162,969 B2 | 4/2012 | Brister et al. |
| 8,173,113 B1 | 5/2012 | Scholz et al. |
| 8,177,853 B2 | 5/2012 | Stack et al. |
| 8,180,592 B2 | 5/2012 | Yuen et al. |
| 8,181,655 B2 | 5/2012 | Bardach et al. |
| 8,182,459 B2 | 5/2012 | Dann et al. |
| 8,185,206 B2 | 5/2012 | Starkebaum et al. |
| 8,187,289 B2 | 5/2012 | Tacchino et al. |
| 8,187,297 B2 | 5/2012 | Makower et al. |
| 8,192,350 B2 | 6/2012 | Ortiz et al. |
| 8,192,455 B2 | 6/2012 | Brazzini et al. |
| 8,197,498 B2 | 6/2012 | Coleman et al. |
| 8,198,048 B2 | 6/2012 | Zuker et al. |
| 8,202,291 B1 | 6/2012 | Brister et al. |
| 8,206,456 B2 | 6/2012 | Stack et al. |
| 8,209,037 B2 | 6/2012 | Laufer et al. |
| 8,211,128 B1 | 7/2012 | Facundus et al. |
| 8,211,186 B2 | 7/2012 | Belhe et al. |
| 8,214,049 B2 | 7/2012 | Brynelsen et al. |
| 8,216,158 B2 | 7/2012 | Johnson |
| 8,217,001 B2 | 7/2012 | Cowley et al. |
| 8,219,171 B2 | 7/2012 | Benoist |
| 8,226,593 B2 | 7/2012 | Graham et al. |
| 8,226,602 B2 | 7/2012 | Quijana et al. |
| 8,229,676 B2 | 7/2012 | Hyde et al. |
| 8,230,865 B2 | 7/2012 | Shalon |
| 8,233,954 B2 | 7/2012 | Kling et al. |
| 8,236,023 B2 | 8/2012 | Birk et al. |
| 8,236,242 B2 | 8/2012 | Drucker et al. |
| 8,236,285 B2 | 8/2012 | Dugger et al. |
| 8,236,348 B2 | 8/2012 | Gin et al. |
| 8,239,027 B2 | 8/2012 | Imran |
| 8,241,202 B2 | 8/2012 | Balbierz et al. |
| 8,251,888 B2 | 8/2012 | Roslin et al. |
| 8,252,009 B2 | 8/2012 | Weller et al. |
| 8,252,744 B2 | 8/2012 | Stojanovic-Susulic et al. |
| 8,265,758 B2 | 9/2012 | Policker et al. |
| 8,267,888 B2 | 9/2012 | Marco et al. |
| 8,275,438 B2 | 9/2012 | Simpson et al. |
| 8,280,505 B2 | 10/2012 | Craig |
| 8,282,598 B2 | 10/2012 | Belhe et al. |
| 8,282,623 B2 | 10/2012 | Klein et al. |
| 8,282,666 B2 | 10/2012 | Birk |
| 8,285,488 B2 | 10/2012 | Hyde et al. |
| 8,287,453 B2 | 10/2012 | Li et al. |
| 8,287,554 B2 | 10/2012 | Cerier et al. |
| 8,287,898 B2 | 10/2012 | Jandacek et al. |
| 8,290,712 B2 | 10/2012 | Hyde et al. |
| 8,292,800 B2 | 10/2012 | Stone et al. |
| 8,292,911 B2 | 10/2012 | Brister et al. |
| 8,295,926 B2 | 10/2012 | Dobak |
| 8,295,932 B2 | 10/2012 | Bitton et al. |
| 8,298,142 B2 | 10/2012 | Simpson et al. |
| 8,299,930 B2 | 10/2012 | Schmid-Schonbein |
| 8,301,256 B2 | 10/2012 | Policker et al. |
| 8,303,573 B2 | 11/2012 | Boyden et al. |
| 8,303,669 B2 | 11/2012 | Meade et al. |
| 8,308,630 B2 | 11/2012 | Birk et al. |
| 8,310,368 B2 | 11/2012 | Hoover et al. |
| 8,311,769 B2 | 11/2012 | Yuen et al. |
| 8,311,770 B2 | 11/2012 | Yuen et al. |
| 8,314,224 B2 | 11/2012 | Adler et al. |
| 8,317,677 B2 | 11/2012 | Bertolote et al. |
| 8,321,030 B2 | 11/2012 | Maniak et al. |
| 8,321,141 B2 | 11/2012 | Hyde et al. |

(56) References Cited

U.S. PATENT DOCUMENTS

| | | |
|---|---|---|
| 8,323,180 B2 | 12/2012 | Birk et al. |
| 8,328,420 B2 | 12/2012 | Abreu |
| 8,333,754 B2 | 12/2012 | Boyden et al. |
| 8,334,367 B2 | 12/2012 | Adler |
| 8,337,566 B2 | 12/2012 | Stack et al. |
| 8,340,772 B2 | 12/2012 | Vase et al. |
| 8,345,930 B2 | 1/2013 | Tamrakar et al. |
| 8,346,363 B2 | 1/2013 | Darvish et al. |
| 8,355,875 B2 | 1/2013 | Hyde et al. |
| 8,363,913 B2 | 1/2013 | Boushey et al. |
| 2001/0037127 A1 | 11/2001 | De Hoyos Garza |
| 2001/0049470 A1 | 12/2001 | Mault et al. |
| 2002/0022774 A1 | 2/2002 | Karnieli |
| 2002/0027164 A1 | 3/2002 | Mault et al. |
| 2002/0047867 A1 | 4/2002 | Mault et al. |
| 2002/0049482 A1 | 4/2002 | Fabian et al. |
| 2002/0072780 A1 | 6/2002 | Foley |
| 2002/0109600 A1 | 8/2002 | Mault et al. |
| 2002/0124017 A1 | 9/2002 | Mault |
| 2002/0133378 A1 | 9/2002 | Mault et al. |
| 2002/0156351 A1 | 10/2002 | Sagel |
| 2002/0187204 A1 | 12/2002 | Alviar et al. |
| 2003/0009202 A1 | 1/2003 | Levine |
| 2003/0021822 A1 | 1/2003 | Lloyd |
| 2003/0059737 A1 | 3/2003 | Hall |
| 2003/0065257 A1 | 4/2003 | Mault et al. |
| 2003/0076983 A1 | 4/2003 | Cox |
| 2003/0095936 A1 | 5/2003 | Light |
| 2003/0113310 A1 | 6/2003 | Van Laere et al. |
| 2003/0152607 A1 | 8/2003 | Mault |
| 2003/0163354 A1 | 8/2003 | Shamoun |
| 2003/0165799 A1 | 9/2003 | Bisogno |
| 2003/0167024 A1 | 9/2003 | Imran et al. |
| 2003/0171711 A1 | 9/2003 | Rohr et al. |
| 2003/0208110 A1 | 11/2003 | Mault et al. |
| 2003/0219513 A1 | 11/2003 | Gordon |
| 2004/0034289 A1 | 2/2004 | Teller et al. |
| 2004/0044376 A1 | 3/2004 | Flesler et al. |
| 2004/0059393 A1 | 3/2004 | Policker et al. |
| 2004/0071801 A1 | 4/2004 | Edell et al. |
| 2004/0073142 A1 | 4/2004 | Takeuchi et al. |
| 2004/0088023 A1 | 5/2004 | Imran et al. |
| 2004/0109886 A1 | 6/2004 | Rigby |
| 2004/0122452 A1 | 6/2004 | Deem et al. |
| 2004/0122453 A1 | 6/2004 | Deem et al. |
| 2004/0131661 A1 | 7/2004 | Auffret et al. |
| 2004/0133081 A1 | 7/2004 | Teller et al. |
| 2004/0147816 A1 | 7/2004 | Policker et al. |
| 2004/0151771 A1 | 8/2004 | Gin et al. |
| 2004/0152957 A1 | 8/2004 | Stivoric et al. |
| 2004/0156920 A1 | 8/2004 | Kane |
| 2004/0162595 A1 | 8/2004 | Foley |
| 2004/0167583 A1 | 8/2004 | Knudson et al. |
| 2004/0172142 A1 | 9/2004 | Stack et al. |
| 2004/0186528 A1 | 9/2004 | Ries et al. |
| 2004/0192760 A1 | 9/2004 | Whittle et al. |
| 2004/0231299 A1 | 11/2004 | Yakushigawa et al. |
| 2004/0243195 A1 | 12/2004 | Imran et al. |
| 2004/0244669 A1 | 12/2004 | Gin et al. |
| 2004/0247702 A1 | 12/2004 | Rajendran et al. |
| 2005/0004436 A1 | 1/2005 | Nissila et al. |
| 2005/0008994 A1 | 1/2005 | Bisogno |
| 2005/0014111 A1 | 1/2005 | Matson |
| 2005/0037031 A1 | 2/2005 | Jackson |
| 2005/0038415 A1 | 2/2005 | Rohr et al. |
| 2005/0053555 A1 | 3/2005 | Pederson |
| 2005/0065571 A1 | 3/2005 | Imran |
| 2005/0090873 A1 | 4/2005 | Imran |
| 2005/0096514 A1 | 5/2005 | Starkebaum |
| 2005/0096637 A1 | 5/2005 | Heruth |
| 2005/0112149 A1 | 5/2005 | Belote et al. |
| 2005/0113649 A1 | 5/2005 | Bergantino |
| 2005/0113650 A1 | 5/2005 | Pacione et al. |
| 2005/0146419 A1 | 7/2005 | Porter |
| 2005/0149142 A1 | 7/2005 | Starkebaum |
| 2005/0222638 A1 | 10/2005 | Foley et al. |
| 2005/0240253 A1 | 10/2005 | Tyler et al. |
| 2005/0247213 A1 | 11/2005 | Slilaty |
| 2005/0263160 A1 | 12/2005 | Utley et al. |
| 2005/0266385 A1 | 12/2005 | Bisogno |
| 2005/0277900 A1 | 12/2005 | Klein et al. |
| 2005/0283096 A1 | 12/2005 | Chau et al. |
| 2005/0287495 A1 | 12/2005 | Longley |
| 2006/0015016 A1 | 1/2006 | Thornton |
| 2006/0020298 A1 | 1/2006 | Camilleri et al. |
| 2006/0031102 A1 | 2/2006 | Teller et al. |
| 2006/0036395 A1 | 2/2006 | Shaya et al. |
| 2006/0064037 A1 | 3/2006 | Shalon et al. |
| 2006/0074459 A1 | 4/2006 | Flesler et al. |
| 2006/0074716 A1 | 4/2006 | Tilles et al. |
| 2006/0079944 A1 | 4/2006 | Imran |
| 2006/0089571 A1 | 4/2006 | Gertner |
| 2006/0089699 A1 | 4/2006 | Imran |
| 2006/0105068 A1 | 5/2006 | Fleischner |
| 2006/0106332 A1 | 5/2006 | Knudson et al. |
| 2006/0122468 A1 | 6/2006 | Tavor |
| 2006/0122474 A1 | 6/2006 | Teller et al. |
| 2006/0129201 A1 | 6/2006 | Lee et al. |
| 2006/0173238 A1 | 8/2006 | Starkebaum |
| 2006/0173508 A1 | 8/2006 | Stone et al. |
| 2006/0189853 A1 | 8/2006 | Brown |
| 2006/0193795 A1 | 8/2006 | Zuckerman |
| 2006/0197670 A1 | 9/2006 | Breibart |
| 2006/0199997 A1 | 9/2006 | Hassler et al. |
| 2006/0206169 A1 | 9/2006 | Schuler |
| 2006/0229504 A1 | 10/2006 | Johnson |
| 2006/0235448 A1 | 10/2006 | Roslin et al. |
| 2006/0235487 A1 | 10/2006 | Meyer et al. |
| 2006/0252983 A1 | 11/2006 | Lembo et al. |
| 2006/0263750 A1 | 11/2006 | Gordon |
| 2006/0264699 A1 | 11/2006 | Gertner |
| 2006/0264730 A1 | 11/2006 | Stivoric et al. |
| 2007/0016262 A1 | 1/2007 | Gross et al. |
| 2007/0021979 A1 | 1/2007 | Cosentino et al. |
| 2007/0027366 A1 | 2/2007 | Osburn |
| 2007/0027493 A1 | 2/2007 | Ben-Haim et al. |
| 2007/0027498 A1 | 2/2007 | Maschino et al. |
| 2007/0028453 A1 | 2/2007 | Crow |
| 2007/0030339 A1 | 2/2007 | Findlay et al. |
| 2007/0042058 A1 | 2/2007 | George et al. |
| 2007/0048369 A1 | 3/2007 | Foreman et al. |
| 2007/0050058 A1 | 3/2007 | Zuziak et al. |
| 2007/0059672 A1 | 3/2007 | Shaw |
| 2007/0060812 A1 | 3/2007 | Harel et al. |
| 2007/0077300 A1 | 4/2007 | Wynn et al. |
| 2007/0082843 A1 | 4/2007 | Stojanovic-Susulic et al. |
| 2007/0089335 A1 | 4/2007 | Smith et al. |
| 2007/0093910 A1 | 4/2007 | Imran |
| 2007/0098856 A1 | 5/2007 | LePine |
| 2007/0104783 A1 | 5/2007 | Domb et al. |
| 2007/0104805 A1 | 5/2007 | Udell |
| 2007/0106129 A1 | 5/2007 | Srivathsa et al. |
| 2007/0106138 A1 | 5/2007 | Beiski et al. |
| 2007/0135846 A1 | 6/2007 | Knudson et al. |
| 2007/0149994 A1 | 6/2007 | Sosnowski et al. |
| 2007/0150021 A1 | 6/2007 | Chen et al. |
| 2007/0156013 A1 | 7/2007 | Birk |
| 2007/0160735 A1 | 7/2007 | Stillman |
| 2007/0162085 A1 | 7/2007 | Dilorenzo |
| 2007/0173703 A1 | 7/2007 | Lee et al. |
| 2007/0179355 A1 | 8/2007 | Rosen |
| 2007/0179556 A1 | 8/2007 | Ben-Haim et al. |
| 2007/0196436 A1 | 8/2007 | Abrahams et al. |
| 2007/0203521 A1 | 8/2007 | Dobak et al. |
| 2007/0207199 A1 | 9/2007 | Sogin |
| 2007/0208593 A1 | 9/2007 | Hercules |
| 2007/0250083 A1 | 10/2007 | Deem et al. |
| 2007/0255334 A1 | 11/2007 | Keimel et al. |
| 2007/0265598 A1 | 11/2007 | Karasik |
| 2007/0265645 A1 | 11/2007 | Birk et al. |
| 2007/0265646 A1 | 11/2007 | Mccoy et al. |
| 2007/0276293 A1 | 11/2007 | Gertner |
| 2007/0293885 A1 | 12/2007 | Binmoeller |
| 2007/0299320 A1 | 12/2007 | Policker et al. |

(56) References Cited

U.S. PATENT DOCUMENTS

| | | |
|---|---|---|
| 2008/0014327 A1 | 1/2008 | Stillman |
| 2008/0021512 A1 | 1/2008 | Knudson et al. |
| 2008/0033345 A1* | 2/2008 | Langloss et al. ............... 604/28 |
| 2008/0033364 A1 | 2/2008 | Kamen et al. |
| 2008/0033365 A1 | 2/2008 | Solovay et al. |
| 2008/0039809 A1 | 2/2008 | Kamen et al. |
| 2008/0044797 A1 | 2/2008 | Bardach et al. |
| 2008/0046013 A1 | 2/2008 | Lozano |
| 2008/0051824 A1 | 2/2008 | Gertner |
| 2008/0058887 A1 | 3/2008 | Griffin et al. |
| 2008/0065168 A1 | 3/2008 | Bitton et al. |
| 2008/0075813 A1 | 3/2008 | Smith et al. |
| 2008/0086179 A1 | 4/2008 | Sharma |
| 2008/0091146 A1 | 4/2008 | Solovay et al. |
| 2008/0102143 A1 | 5/2008 | Freis et al. |
| 2008/0114336 A1* | 5/2008 | Sei ............................. 604/540 |
| 2008/0137486 A1 | 6/2008 | Czarenk et al. |
| 2008/0138447 A1 | 6/2008 | Riggins et al. |
| 2008/0141282 A1 | 6/2008 | Elber et al. |
| 2008/0147002 A1 | 6/2008 | Gertner |
| 2008/0152705 A1 | 6/2008 | Udell et al. |
| 2008/0154191 A1 | 6/2008 | Gobel |
| 2008/0161654 A1 | 7/2008 | Teller et al. |
| 2008/0161655 A1 | 7/2008 | Teller et al. |
| 2008/0161717 A1 | 7/2008 | Gertner |
| 2008/0167536 A1 | 7/2008 | Teller et al. |
| 2008/0167537 A1 | 7/2008 | Teller et al. |
| 2008/0167538 A1 | 7/2008 | Teller et al. |
| 2008/0167539 A1 | 7/2008 | Teller et al. |
| 2008/0171920 A1 | 7/2008 | Teller et al. |
| 2008/0171921 A1 | 7/2008 | Teller et al. |
| 2008/0171922 A1 | 7/2008 | Teller et al. |
| 2008/0172072 A1 | 7/2008 | Pool et al. |
| 2008/0183238 A1 | 7/2008 | Chen |
| 2008/0188766 A1 | 8/2008 | Gertner |
| 2008/0195171 A1 | 8/2008 | Sharma |
| 2008/0208240 A1 | 8/2008 | Paz |
| 2008/0221644 A1 | 9/2008 | Vallapureddy et al. |
| 2008/0243071 A1 | 10/2008 | Quijano et al. |
| 2008/0255093 A1 | 10/2008 | Tam et al. |
| 2008/0255955 A1 | 10/2008 | Simons-Nikolova |
| 2008/0262411 A1 | 10/2008 | Dobak |
| 2008/0262557 A1 | 10/2008 | Brown |
| 2008/0267444 A1 | 10/2008 | Simons-Nikolova |
| 2008/0270947 A1 | 10/2008 | Elber et al. |
| 2008/0275309 A1 | 11/2008 | Stivoric et al. |
| 2008/0275484 A1 | 11/2008 | Gertner |
| 2008/0276461 A1 | 11/2008 | Gold |
| 2008/0319471 A1 | 12/2008 | Sosnowski et al. |
| 2009/0012433 A1 | 1/2009 | Fernstrom et al. |
| 2009/0018594 A1 | 1/2009 | Laufer et al. |
| 2009/0018605 A1 | 1/2009 | Imran et al. |
| 2009/0018606 A1 | 1/2009 | Sparks et al. |
| 2009/0030474 A1 | 1/2009 | Brynelsen et al. |
| 2009/0030475 A1 | 1/2009 | Brynelsen et al. |
| 2009/0062725 A1 | 3/2009 | Goebel |
| 2009/0062881 A1 | 3/2009 | Gross et al. |
| 2009/0081291 A1 | 3/2009 | Gin et al. |
| 2009/0088816 A1 | 4/2009 | Harel et al. |
| 2009/0093767 A1 | 4/2009 | Kelleher |
| 2009/0112800 A1 | 4/2009 | Athsani |
| 2009/0118797 A1 | 5/2009 | Kliger et al. |
| 2009/0123380 A1 | 5/2009 | Hirsch |
| 2009/0123524 A1 | 5/2009 | Hirsch |
| 2009/0123579 A1 | 5/2009 | Hirsch |
| 2009/0130178 A1 | 5/2009 | Oronsky et al. |
| 2009/0131968 A1 | 5/2009 | Birk |
| 2009/0149910 A1 | 6/2009 | Imran et al. |
| 2009/0157106 A1 | 6/2009 | Marcotte et al. |
| 2009/0171375 A1* | 7/2009 | Coe et al. ..................... 606/151 |
| 2009/0176526 A1 | 7/2009 | Altman |
| 2009/0177068 A1 | 7/2009 | Stivoric et al. |
| 2009/0191514 A1 | 7/2009 | Barnow |
| 2009/0192534 A1 | 7/2009 | Ortiz et al. |
| 2009/0192535 A1 | 7/2009 | Kasic |
| 2009/0197963 A1 | 8/2009 | Llewellyn |
| 2009/0204063 A1* | 8/2009 | Policker et al. ............... 604/26 |
| 2009/0204131 A1 | 8/2009 | Ortiz et al. |
| 2009/0204132 A1 | 8/2009 | Ortiz et al. |
| 2009/0214445 A1 | 8/2009 | Boghani et al. |
| 2009/0216255 A1 | 8/2009 | Coe et al. |
| 2009/0219159 A1 | 9/2009 | Morgenstern |
| 2009/0240194 A1 | 9/2009 | Keimel et al. |
| 2009/0240340 A1 | 9/2009 | Levine et al. |
| 2009/0247992 A1 | 10/2009 | Shalon et al. |
| 2009/0248171 A1 | 10/2009 | Levine et al. |
| 2009/0253105 A1 | 10/2009 | Lepine |
| 2009/0259246 A1 | 10/2009 | Eskaros et al. |
| 2009/0259274 A1 | 10/2009 | Simon et al. |
| 2009/0259279 A1 | 10/2009 | Dobak |
| 2009/0261987 A1 | 10/2009 | Sun |
| 2009/0264951 A1 | 10/2009 | Sharma |
| 2009/0270904 A1 | 10/2009 | Birk et al. |
| 2009/0275973 A1 | 11/2009 | Chen et al. |
| 2009/0281449 A1 | 11/2009 | Thrower et al. |
| 2009/0299434 A1 | 12/2009 | Imran et al. |
| 2009/0306462 A1 | 12/2009 | Lechner |
| 2009/0312785 A1 | 12/2009 | Stone et al. |
| 2009/0312817 A1 | 12/2009 | Hogle et al. |
| 2010/0004755 A1 | 1/2010 | Imran |
| 2010/0049274 A1 | 2/2010 | Cholette |
| 2010/0055245 A1 | 3/2010 | Havekotte et al. |
| 2010/0057564 A1 | 3/2010 | Godsey et al. |
| 2010/0062119 A1 | 3/2010 | Miller-Kovach |
| 2010/0062402 A1 | 3/2010 | Miller-Kovach |
| 2010/0076345 A1 | 3/2010 | Soffer et al. |
| 2010/0079291 A1 | 4/2010 | Kroll et al. |
| 2010/0080875 A1 | 4/2010 | Miller-Kovach |
| 2010/0087706 A1 | 4/2010 | Syed et al. |
| 2010/0094374 A1 | 4/2010 | Imran |
| 2010/0094375 A1 | 4/2010 | Donders et al. |
| 2010/0098783 A1 | 4/2010 | Sommerfeld et al. |
| 2010/0100116 A1 | 4/2010 | Brister et al. |
| 2010/0100117 A1 | 4/2010 | Brister et al. |
| 2010/0106130 A1 | 4/2010 | Solovay et al. |
| 2010/0106131 A1 | 4/2010 | Klein et al. |
| 2010/0109876 A1 | 5/2010 | Schmid-Schonbein |
| 2010/0111383 A1 | 5/2010 | Boushey et al. |
| 2010/0114125 A1 | 5/2010 | Albrecht et al. |
| 2010/0114150 A1 | 5/2010 | Magal |
| 2010/0125176 A1 | 5/2010 | Hyde et al. |
| 2010/0125177 A1 | 5/2010 | Hyde et al. |
| 2010/0125178 A1 | 5/2010 | Hyde et al. |
| 2010/0125179 A1 | 5/2010 | Hyde et al. |
| 2010/0125180 A1 | 5/2010 | Hyde et al. |
| 2010/0125181 A1 | 5/2010 | Hyde et al. |
| 2010/0125417 A1 | 5/2010 | Hyde et al. |
| 2010/0125418 A1 | 5/2010 | Hyde et al. |
| 2010/0125419 A1 | 5/2010 | Hyde et al. |
| 2010/0125420 A1 | 5/2010 | Hyde et al. |
| 2010/0130998 A1 | 5/2010 | Alverdy |
| 2010/0135945 A1 | 6/2010 | Murdock et al. |
| 2010/0137897 A1 | 6/2010 | Brister et al. |
| 2010/0145301 A1 | 6/2010 | Magal |
| 2010/0145378 A1 | 6/2010 | Gertner |
| 2010/0152532 A1 | 6/2010 | Marcotte |
| 2010/0152764 A1 | 6/2010 | Merkle |
| 2010/0160745 A1 | 6/2010 | Hills et al. |
| 2010/0168815 A1 | 7/2010 | Knudson et al. |
| 2010/0173269 A1 | 7/2010 | Puri et al. |
| 2010/0183700 A1 | 7/2010 | Stojanovic-Susulic |
| 2010/0191155 A1 | 7/2010 | Kim et al. |
| 2010/0194573 A1 | 8/2010 | Hoover et al. |
| 2010/0204669 A1 | 8/2010 | Knight |
| 2010/0204723 A1 | 8/2010 | Gertner |
| 2010/0205209 A1 | 8/2010 | Jokinen |
| 2010/0209897 A1 | 8/2010 | Utley et al. |
| 2010/0215584 A1 | 8/2010 | Passe |
| 2010/0217194 A1 | 8/2010 | Pang |
| 2010/0228080 A1 | 9/2010 | Tavori et al. |
| 2010/0228160 A1 | 9/2010 | Schweizer |
| 2010/0234682 A1 | 9/2010 | Gertner |
| 2010/0234917 A1 | 9/2010 | Imran |
| 2010/0240962 A1 | 9/2010 | Contant |

(56) References Cited

U.S. PATENT DOCUMENTS

| | | |
|---|---|---|
| 2010/0241090 A1 | 9/2010 | Klein et al. |
| 2010/0256775 A1 | 10/2010 | Belhe et al. |
| 2010/0267643 A1 | 10/2010 | Baron et al. |
| 2010/0268306 A1 | 10/2010 | Maniak et al. |
| 2010/0274274 A1 | 10/2010 | Roslin et al. |
| 2010/0286660 A1 | 11/2010 | Gross |
| 2010/0286745 A1 | 11/2010 | Imran |
| 2010/0291515 A1 | 11/2010 | Pinnisi et al. |
| 2010/0298631 A1 | 11/2010 | Stack et al. |
| 2010/0298632 A1 | 11/2010 | Levine et al. |
| 2010/0298812 A1 | 11/2010 | Wolkenstorfer |
| 2010/0305468 A1 | 12/2010 | Policker et al. |
| 2010/0305656 A1 | 12/2010 | Imran et al. |
| 2010/0312049 A1 | 12/2010 | Forsell |
| 2010/0312050 A1 | 12/2010 | Forsell |
| 2010/0312147 A1 | 12/2010 | Gertner |
| 2010/0316768 A1 | 12/2010 | Stillman |
| 2010/0324358 A1 | 12/2010 | Birk et al. |
| 2010/0324361 A1 | 12/2010 | Forsell |
| 2010/0324432 A1 | 12/2010 | Bjorling et al. |
| 2010/0331616 A1 | 12/2010 | Forsell |
| 2010/0331617 A1 | 12/2010 | Forsell |
| 2010/0332000 A1 | 12/2010 | Forsell |
| 2010/0332571 A1 | 12/2010 | Healey et al. |
| 2011/0004266 A1 | 1/2011 | Sharma |
| 2011/0009690 A1 | 1/2011 | Belhe et al. |
| 2011/0009887 A1 | 1/2011 | Harris et al. |
| 2011/0009895 A1 | 1/2011 | Gertner |
| 2011/0009896 A1 | 1/2011 | Forsell |
| 2011/0009980 A1 | 1/2011 | Levy et al. |
| 2011/0015665 A1 | 1/2011 | Marco et al. |
| 2011/0015666 A1 | 1/2011 | Marco et al. |
| 2011/0021968 A1 | 1/2011 | Knudson et al. |
| 2011/0022072 A1 | 1/2011 | Marco et al. |
| 2011/0034760 A1 | 2/2011 | Brynelsen et al. |
| 2011/0034967 A1 | 2/2011 | Chen et al. |
| 2011/0034968 A1 | 2/2011 | Knudson et al. |
| 2011/0040232 A1 | 2/2011 | Magal |
| 2011/0040318 A1 | 2/2011 | Marco et al. |
| 2011/0060308 A1 | 3/2011 | Stokes et al. |
| 2011/0060358 A1 | 3/2011 | Stokes et al. |
| 2011/0065660 A1 | 3/2011 | Baron et al. |
| 2011/0066207 A1 | 3/2011 | Imran |
| 2011/0082407 A1 | 4/2011 | Aronne |
| 2011/0082442 A1 | 4/2011 | Solovay et al. |
| 2011/0087076 A1 | 4/2011 | Brynelsen et al. |
| 2011/0087137 A1 | 4/2011 | Hanoun |
| 2011/0087146 A1 | 4/2011 | Ryan et al. |
| 2011/0092998 A1 | 4/2011 | Hirszowicz et al. |
| 2011/0098725 A1 | 4/2011 | Cox et al. |
| 2011/0104336 A1 | 5/2011 | Stillman |
| 2011/0106129 A1 | 5/2011 | Gertner |
| 2011/0106273 A1* | 5/2011 | Belhe et al. ............... 623/23.64 |
| 2011/0125063 A1 | 5/2011 | Shalon et al. |
| 2011/0125211 A1 | 5/2011 | Griffin et al. |
| 2011/0130626 A1 | 6/2011 | Hassler et al. |
| 2011/0136909 A1 | 6/2011 | Imada et al. |
| 2011/0152899 A1 | 6/2011 | Deem et al. |
| 2011/0160129 A1 | 6/2011 | Imran |
| 2011/0160699 A1 | 6/2011 | Imran |
| 2011/0166065 A1 | 7/2011 | Bhanot et al. |
| 2011/0166582 A1 | 7/2011 | Syed et al. |
| 2011/0172693 A1 | 7/2011 | Forsell |
| 2011/0178480 A1 | 7/2011 | Solovay et al. |
| 2011/0178544 A1 | 7/2011 | Sosnowski et al. |
| 2011/0182477 A1 | 7/2011 | Tamrakar et al. |
| 2011/0184229 A1 | 7/2011 | Raven et al. |
| 2011/0184247 A1 | 7/2011 | Contant et al. |
| 2011/0190719 A1 | 8/2011 | Kamen et al. |
| 2011/0196411 A1 | 8/2011 | Forsell |
| 2011/0196504 A1 | 8/2011 | Imran |
| 2011/0201874 A1 | 8/2011 | Birk et al. |
| 2011/0207994 A1 | 8/2011 | Burrell et al. |
| 2011/0207995 A1 | 8/2011 | Snow et al. |
| 2011/0208209 A1 | 8/2011 | Ewers et al. |
| 2011/0208216 A1 | 8/2011 | Fobi et al. |
| 2011/0213385 A1 | 9/2011 | Ewers et al. |
| 2011/0213448 A1 | 9/2011 | Kim |
| 2011/0213469 A1 | 9/2011 | Chin et al. |
| 2011/0218407 A1 | 9/2011 | Haberman et al. |
| 2011/0224155 A1 | 9/2011 | Tachdjian et al. |
| 2011/0224714 A1 | 9/2011 | Gertner |
| 2011/0230502 A1 | 9/2011 | Tachdjian et al. |
| 2011/0230938 A1 | 9/2011 | Simon et al. |
| 2011/0238035 A1 | 9/2011 | Jaax et al. |
| 2011/0244514 A1 | 10/2011 | Zuker et al. |
| 2011/0245598 A1 | 10/2011 | Gertner |
| 2011/0245752 A1 | 10/2011 | Levine et al. |
| 2011/0251495 A1 | 10/2011 | Province et al. |
| 2011/0269711 A1 | 11/2011 | Adden et al. |
| 2011/0270025 A1 | 11/2011 | Fridez et al. |
| 2011/0270030 A1 | 11/2011 | Birk et al. |
| 2011/0270344 A1 | 11/2011 | Knudson et al. |
| 2011/0270410 A1 | 11/2011 | Stack et al. |
| 2011/0275887 A1 | 11/2011 | Birk |
| 2011/0276112 A1 | 11/2011 | Simon et al. |
| 2011/0276312 A1 | 11/2011 | Shalon et al. |
| 2011/0282411 A1 | 11/2011 | Knudson et al. |
| 2011/0295055 A1 | 12/2011 | Albrecht et al. |
| 2011/0295056 A1 | 12/2011 | Aldridge et al. |
| 2011/0295057 A1 | 12/2011 | Aldridge et al. |
| 2011/0295335 A1 | 12/2011 | Sharma et al. |
| 2011/0295336 A1 | 12/2011 | Sharma et al. |
| 2011/0306824 A1 | 12/2011 | Perron et al. |
| 2011/0307023 A1 | 12/2011 | Tweden et al. |
| 2011/0307027 A1 | 12/2011 | Sharma et al. |
| 2011/0307028 A1 | 12/2011 | Sharma et al. |
| 2011/0307075 A1 | 12/2011 | Sharma |
| 2011/0313240 A1 | 12/2011 | Phillips et al. |
| 2011/0314849 A1 | 12/2011 | Park et al. |
| 2011/0318717 A1 | 12/2011 | Adamowicz |
| 2011/0319924 A1 | 12/2011 | Cole et al. |
| 2011/0319969 A1 | 12/2011 | Dobak |
| 2012/0004590 A1 | 1/2012 | Stack et al. |
| 2012/0004676 A1 | 1/2012 | Vargas |
| 2012/0009551 A1 | 1/2012 | Pinnisi |
| 2012/0010459 A1 | 1/2012 | Lau et al. |
| 2012/0010590 A1 | 1/2012 | Imran |
| 2012/0015021 A1 | 1/2012 | Mizrahi et al. |
| 2012/0015432 A1 | 1/2012 | Adler |
| 2012/0016287 A1 | 1/2012 | Stack et al. |
| 2012/0016392 A1 | 1/2012 | Silverman et al. |
| 2012/0021388 A1 | 1/2012 | Arbuckle et al. |
| 2012/0022319 A1 | 1/2012 | Muller |
| 2012/0022322 A1 | 1/2012 | Pasricha |
| 2012/0022430 A1 | 1/2012 | Stack et al. |
| 2012/0029550 A1 | 2/2012 | Forsell |
| 2012/0029591 A1 | 2/2012 | Simon et al. |
| 2012/0029601 A1 | 2/2012 | Simon et al. |
| 2012/0031805 A1 | 2/2012 | Stolarczyk |
| 2012/0036875 A1 | 2/2012 | Yun et al. |
| 2012/0040893 A1 | 2/2012 | Cowley et al. |
| 2012/0041463 A1 | 2/2012 | Forsell |
| 2012/0041465 A1 | 2/2012 | Shalon |
| 2012/0041509 A1 | 2/2012 | Knudson et al. |
| 2012/0046674 A1 | 2/2012 | Augarten et al. |
| 2012/0053426 A1 | 3/2012 | Webster et al. |
| 2012/0053504 A1 | 3/2012 | Kagan et al. |
| 2012/0053613 A1 | 3/2012 | Weitzner et al. |
| 2012/0053653 A1 | 3/2012 | Hiernaux et al. |
| 2012/0053660 A1 | 3/2012 | Dobak |
| 2012/0055718 A1 | 3/2012 | Chen |
| 2012/0058217 A1 | 3/2012 | Patty |
| 2012/0059216 A1 | 3/2012 | Perron |
| 2012/0065571 A1 | 3/2012 | Thompson et al. |
| 2012/0065706 A1 | 3/2012 | Vallapureddy et al. |
| 2012/0067937 A1 | 3/2012 | Menzel |
| 2012/0071812 A1 | 3/2012 | Mitelberg et al. |
| 2012/0071900 A1 | 3/2012 | Vahid et al. |
| 2012/0071947 A1 | 3/2012 | Gupta et al. |
| 2012/0072233 A1 | 3/2012 | Hanlon et al. |
| 2012/0077154 A1 | 3/2012 | Highet et al. |
| 2012/0078071 A1 | 3/2012 | Bohm et al. |
| 2012/0083650 A1 | 4/2012 | Raven |

(56) References Cited

U.S. PATENT DOCUMENTS

| | | |
|---|---|---|
| 2012/0083669 A1 | 4/2012 | Abujbara |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0083855 A1 | 4/2012 | Gross et al. |
| 2012/0084053 A1 | 4/2012 | Yuen et al. |
| 2012/0084054 A1 | 4/2012 | Yuen et al. |
| 2012/0088962 A1 | 4/2012 | Franklin et al. |
| 2012/0089168 A1 | 4/2012 | Baker et al. |
| 2012/0089170 A1 | 4/2012 | Dominguez |
| 2012/0089172 A1 | 4/2012 | Babkes et al. |
| 2012/0094942 A1 | 4/2012 | Baron et al. |
| 2012/0095288 A1 | 4/2012 | Snow et al. |
| 2012/0095384 A1 | 4/2012 | Babkes et al. |
| 2012/0095492 A1 | 4/2012 | Babkes et al. |
| 2012/0095494 A1 | 4/2012 | Dominguez et al. |
| 2012/0095495 A1 | 4/2012 | Babkes et al. |
| 2012/0095496 A1 | 4/2012 | Dominguez et al. |
| 2012/0095497 A1 | 4/2012 | Babkes et al. |
| 2012/0095499 A1 | 4/2012 | Babkes et al. |
| 2012/0096405 A1 | 4/2012 | Seo |
| 2012/0101594 A1 | 4/2012 | Fogel |
| 2012/0101874 A1 | 4/2012 | Ben-Haim et al. |
| 2012/0108921 A1 | 5/2012 | Raven et al. |
| 2012/0109051 A1 | 5/2012 | Harrell |
| 2012/0115111 A1 | 5/2012 | Lepine |
| 2012/0115778 A1 | 5/2012 | Karsenty et al. |
| 2012/0116182 A1 | 5/2012 | Wong et al. |
| 2012/0116285 A1 | 5/2012 | Duggirala |
| 2012/0116286 A1 | 5/2012 | Williams et al. |
| 2012/0116536 A1 | 5/2012 | Imran |
| 2012/0123465 A1 | 5/2012 | Nihalani |
| 2012/0126983 A1 | 5/2012 | Breibart |
| 2012/0130273 A1 | 5/2012 | Hassler et al. |
| 2012/0143279 A1 | 6/2012 | Ekchian et al. |
| 2012/0144912 A1 | 6/2012 | Kates et al. |
| 2012/0149996 A1 | 6/2012 | Stivoric et al. |
| 2012/0150316 A1 | 6/2012 | Carvalho |
| 2012/0157409 A1 | 6/2012 | Cherkassky |
| 2012/0160893 A1 | 6/2012 | Harris et al. |
| 2012/0165792 A1 | 6/2012 | Ortiz et al. |
| 2012/0165793 A1 | 6/2012 | Ortiz et al. |
| 2012/0165794 A1 | 6/2012 | Ortiz et al. |
| 2012/0165796 A1 | 6/2012 | Ortiz et al. |
| 2012/0165843 A1 | 6/2012 | Gannoe et al. |
| 2012/0165845 A1 | 6/2012 | Harris et al. |
| 2012/0165855 A1 | 6/2012 | Shalon et al. |
| 2012/0170801 A1 | 7/2012 | De Oliveira et al. |
| 2012/0172782 A1 | 7/2012 | Thompson |
| 2012/0177730 A1 | 7/2012 | Baron et al. |
| 2012/0179665 A1 | 7/2012 | Baarman et al. |
| 2012/0184893 A1 | 7/2012 | Thompson et al. |
| 2012/0190919 A1 | 7/2012 | Phillips et al. |
| 2012/0191123 A1 | 7/2012 | Brister et al. |
| 2012/0191124 A1 | 7/2012 | Brister et al. |
| 2012/0191125 A1 | 7/2012 | Babkes et al. |
| 2012/0191126 A1 | 7/2012 | Pecor et al. |
| 2012/0195954 A1 | 8/2012 | Maynard |
| 2012/0197069 A1 | 8/2012 | Lau et al. |
| 2012/0201725 A1 | 8/2012 | Imran |
| 2012/0203061 A1 | 8/2012 | Birk |
| 2012/0203081 A1 | 8/2012 | Leboeuf et al. |
| 2012/0208748 A1 | 8/2012 | Chen et al. |
| 2012/0209354 A1 | 8/2012 | Raykhman |
| 2012/0209400 A1 | 8/2012 | Schurr |
| 2012/0214140 A1 | 8/2012 | Brynelsen et al. |
| 2012/0215061 A1 | 8/2012 | Fridez et al. |
| 2012/0215062 A1 | 8/2012 | Coe |
| 2012/0215152 A1 | 8/2012 | Levine et al. |
| 2012/0215249 A1 | 8/2012 | Brazzini et al. |
| 2012/0221037 A1 | 8/2012 | Birk et al. |
| 2012/0221495 A1 | 8/2012 | Landers |
| 2012/0226471 A1 | 9/2012 | Yuen et al. |
| 2012/0226472 A1 | 9/2012 | Yuen et al. |
| 2012/0232361 A1 | 9/2012 | Birk |
| 2012/0232459 A1 | 9/2012 | Dann et al. |
| 2012/0232460 A1 | 9/2012 | Raven et al. |
| 2012/0232576 A1 | 9/2012 | Brister et al. |
| 2012/0232577 A1 | 9/2012 | Birk et al. |
| 2012/0245553 A1 | 9/2012 | Raven et al. |
| 2012/0253259 A1 | 10/2012 | Belhe et al. |
| 2012/0253260 A1 | 10/2012 | Belhe et al. |
| 2012/0253378 A1 | 10/2012 | Makower et al. |
| 2012/0259389 A1 | 10/2012 | Starkebaum et al. |
| 2012/0259427 A1 | 10/2012 | Graham et al. |
| 2012/0265030 A1 | 10/2012 | Li |
| 2012/0265224 A1 | 10/2012 | Coleman et al. |
| 2012/0265234 A1 | 10/2012 | Brister et al. |
| 2012/0271217 A1 | 10/2012 | Stack et al. |
| 2012/0277619 A1 | 11/2012 | Starkebaum et al. |
| 2012/0277661 A1 | 11/2012 | Bernard et al. |
| 2012/0277814 A1 | 11/2012 | Schuler |
| 2012/0277837 A1 | 11/2012 | Schuler |
| 2012/0283766 A1 | 11/2012 | Makower et al. |
| 2012/0289992 A1 | 11/2012 | Quijano et al. |
| 2012/0295233 A1 | 11/2012 | Cooperman |
| 2012/0296157 A1 | 11/2012 | Tozzi et al. |
| 2012/0296348 A1 | 11/2012 | Saadat et al. |
| 2012/0296354 A1 | 11/2012 | Hsu et al. |
| 2012/0299723 A1 | 11/2012 | Hafezi et al. |
| 2012/0302936 A1 | 11/2012 | Belhe et al. |
| 2012/0310295 A1 | 12/2012 | Libbus et al. |
| 2012/0313776 A1 | 12/2012 | Utter |
| 2012/0316387 A1 | 12/2012 | Volker |
| 2012/0316451 A1 | 12/2012 | Province et al. |
| 2012/0316459 A1 | 12/2012 | Abreu |
| 2012/0316932 A1 | 12/2012 | Rahman et al. |
| 2012/0317167 A1 | 12/2012 | Rahman et al. |
| 2012/0323099 A1 | 12/2012 | Mothilal et al. |
| 2012/0326873 A1 | 12/2012 | Utter |
| 2013/0002435 A1 | 1/2013 | Utter |
| 2013/0004923 A1 | 1/2013 | Utter |
| 2013/0006063 A1 | 1/2013 | Wang |
| 2013/0006125 A1 | 1/2013 | Kroll et al. |
| 2013/0006807 A1 | 1/2013 | Bai et al. |
| 2013/0027060 A1 | 1/2013 | Tralshawala |
| 2013/0029807 A1 | 1/2013 | Amsel |

\* cited by examiner

ADJUSTABLE GASTROINTESTINAL BIFURCATION (AGB) FOR REDUCED ABSORPTION OF UNHEALTHY FOOD

CROSS-REFERENCE TO RELATED APPLICATIONS

This patent application claims the priority benefit of U.S. Provisional Patent Application No. 61/746,263 entitled "Adjustable Gastrointestinal Bifurcation (AGB) for Reduced Absorption of Unhealthy Food" filed on Dec. 27, 2012 by Robert A. Connor of Medibotics, LLC.

FEDERALLY SPONSORED RESEARCH

Not Applicable

SEQUENCE LISTING OR PROGRAM

Not Applicable

BACKGROUND

Field of Invention

This invention relates to energy balance, weight loss, and proper nutrition.

Introduction to Energy Balance and Proper Nutrition

The United States population has some of the highest prevalence rates of obese and overweight people in the world. Further, these rates have increased dramatically during recent decades. In the late 1990's, around one in five Americans was obese. Today, that figure has increased to around one in three. It is estimated that around one in five American children is now obese. The prevalence of Americans who are generally overweight is estimated to be as high as two out of three.

This increase in the prevalence of Americans who are overweight or obese has become one of the most common causes of health problems in the United States. Potential adverse health effects from obesity include: cancer (especially endometrial, breast, prostate, and colon cancers); cardiovascular disease (including heart attack and arterial sclerosis); diabetes (type 2); digestive diseases; gallbladder disease; hypertension; kidney failure; obstructive sleep apnea; orthopedic complications; osteoarthritis; respiratory problems; stroke; metabolic syndrome (including hypertension, abnormal lipid levels, and high blood sugar); impairment of quality of life in general including stigma and discrimination; and even death.

There are estimated to be over a quarter-million obesity-related deaths each year in the United States. The tangible costs to American society of obesity have been estimated at over $100 billion dollars per year. This does not include the intangible costs of human pain and suffering. Despite the considerable effort that has been focused on developing new approaches for preventing and treating obesity, the problem is growing. There remains a serious unmet need for new ways to help people to moderate their consumption of unhealthy food, better manage their energy balance, and lose weight in a healthy and sustainable manner.

Obesity is a complex disorder with multiple interacting causal factors including genetic factors, environmental factors, and behavioral factors. A person's behavioral factors include the person's caloric intake (the types and quantities of food which the person consumes) and caloric expenditure (the calories that the person burns in regular activities and exercise). Energy balance is the net difference between caloric intake and caloric expenditure. Other factors being equal, energy balance surplus (caloric intake greater than caloric expenditure) causes weight gain and energy balance deficit (caloric intake less than caloric expenditure) causes weight loss.

Since many factors contribute to obesity, good approaches to weight management are comprehensive in nature. Proper nutrition and management of caloric intake are key parts of a comprehensive approach to weight management. Consumption of "junk food" that is high in simple sugars and saturated fats has increased dramatically during the past couple decades, particularly in the United States. This has contributed significantly to the obesity epidemic. For many people, relying on willpower and dieting is not sufficient to moderate their consumption of unhealthy "junk food." The results are dire consequences for their health and well-being.

The invention that is disclosed herein directly addresses this problem by helping a person to selectively reduce absorption of nutrients from unhealthy food. The invention that is disclosed herein is an innovative technology that can be a key part of a comprehensive system that helps a person to reduce their consumption of unhealthy food, to better manage their energy balance, and to lose weight in a healthy and sustainable manner. In the following sections, we categorize and review the prior art, provide a summary of this invention and its advantages over the prior art, and then provide some detailed examples of how this invention can be embodied to help a person to improve their nutrition and to manage their weight.

Categorization and Review of the Prior Art

It can be challenging to classify prior art into discrete categories. This is the certainly the case in the field of energy balance, weight management, and proper nutrition. There are numerous examples of potentially-relevant prior art. However, classification of the prior art into categories, even if imperfect, is an invaluable tool for reviewing the prior art, identifying its limitations, and setting the stage for discussion of the advantages of the invention that is disclosed in subsequent sections. Towards this end, I now identify 50 general categories of prior art and list examples of prior art which appear to be best classified into each category. This categorization and discussion of the prior art helps to identify limitations of the prior art which are corrected by the invention disclosed herein in subsequent sections. The categories of prior art that are most relevant to this invention are marked with an asterisk "*".

The 50 categories of prior art that I will now discuss are as follows: (1) little or no automated measurement of food consumption, (2) consumed manufactured compound or specifically-isolated natural substance, (3) substance sprinkled on food, (4) manually-ingested spray or pulse, (5) substance-emitting lipstick or toothpaste, (6) substance-emitting adhesive patch in the mouth, (7) dissolving film in mouth, (8) tablet or gum in mouth, (9) intraoral drug delivery, (10) motion guided or directed pill, (11) general implanted drug pump, (12) food purchasing monitoring or modification, (13) food scale, (14) portion size control, (15) mouth size or function modification, (16) chewing and swallowing monitoring, (17) hand and/or arm motion monitoring and modification (wrist), (18) hand and/or arm motion monitoring and modification (utensil), (19) utensil with sensor other than motion sensor, (20) other modification of eating speed, (21) photo identification of food (bar code or other packaging-based code), (22) photo identification of food (manual picture taking and identification), (23) photo identification of food (manual picture taking and automated identification), (24) photo identification of food (automated picture taking and identification), (25*) gastric band, (26*) gastric band with sensor, (27*) gastrointestinal (GI) bypass and tissue plication, (28*) pumping food out of the stomach through an intra-abdominal pathway, (29*) gastric tube, (30*) enzyme flow modification, (31*) gastrointestinal (GI) volume or pressure or flow modification, (32*) gastrointestinal (GI) volume or pressure or flow modification (with drug), (33*) gastrointestinal (GI) sleeve or liner, (34*) gastrointestinal (GI) sleeve or liner (with drug), (35) electrical stimulation (general), (36) electrical stimulation (with glucose sensor), (37) electrical stimulation (with general sensor), (38) electrical stimulation (with taste modification), (39) electrical stimulation (with drug), (40) electrical stimulation (with drug and sensor), (41) salivation stimulation, (42*) general sensor (glucose), (43*) general sensor (electromagnetic), (44*) general sensor (chemical), (45*) general sensor (microwave), (46*) sensor (intraoral), (47*) sensor (general), (48) blood analysis, (49) general energy balance feedback, and (50) miscellaneous energy balance related.

1. Little (or No) Automatic Measurement of Food Consumption

This category includes prior art with little (or no) automatic measurement of food consumption. The vast majority of art in this category requires a person to take specific action (apart from the actual act of eating) in order to record food consumption. For many years, people did this using pencil and paper. Now they can do it with computer assistance (such as an application on a mobile electronic device), but even the computer-assisted methods in this category still rely on specific human action to record food consumption.

Interfaces for the human action required to record food consumption can include: touch screen; voice and/or speech recognition; keyboard, keypad, or buttons; and mouse, trackball, or touchpad. Gesture recognition may become a more popular interface in future years. Devices comprising art in this category can be worn on a person (e.g. a wrist-mounted band or necklace), carried by a person (e.g. a mobile phone or electronic tablet), or stationary (e.g. a desktop computer). Some wrist-mounted bands and food-serving utensils that do not explicitly track caloric intake are nonetheless included in this category because of their innovative measurement of caloric output and their general relevance to energy balance.

Recent art in this category makes manual recording of food consumption easier with computer-assisted features such as menu-driven user interfaces and voice recognition. These can definitely make it easier for someone to associate specific nutrients or calorie amounts with specific common foods through the use of a food-nutrient database. However, even recent art in this category still requires specific action by a person associated with each eating event apart from the actual act of eating. They offer little (or no) automatic monitoring of food consumption. If a person does not record each food consumption event, then such a device is unaware that food has been consumed. Long-term compliance with manual food logs is notoriously low. People tend to under-estimate calories consumed (especially for unstructured snacking). The accuracy of caloric intake monitoring with art in this category still depends largely, or entirely, on the voluntary compliance of the person whose actions are needed to manually record food consumption. Also, even if food consumption is properly recorded, the success of such art in actually modifying food consumption further depends on the effectiveness of its behavioral modification methods.

Examples of prior art that appear to be best classified in this category include: U.S. Pat. No. 4,100,401 (Jul. 11, 1978 Tutt et al.) "Calorie Calculator-Chronometer", U.S. Pat. No. 4,212,079 (Jul. 8, 1980 Segar et al.) "Electronic Calorie Counter", U.S. Pat. No. 4,218,611 (Aug. 19, 1980 Cannon) "Method and Apparatus for Controlling Eating Behavior", U.S. Pat. No. 4,221,959 (Sep. 9, 1980 Sessler) "Checking Device for Checking the Food Intake", U.S. Pat. No. 4,310,316 (Jan. 12, 1982 Thomann) "Diet Control Apparatus", U.S. Pat. No. 4,321,674 (Mar. 23, 1982 Krames et al.) "Nutritional Value Accumulating and Display Device", U.S. Pat. No. 4,650,218 (Mar. 17, 1987 Hawke) "Method and Apparatus for Controlling Caloric Intake", U.S. Pat. No. 4,686,624 (Aug. 11, 1987 Blum et al.) "Portable Apparatus for Acquiring and Processing Data Relative to the Dietetics and/or the Health of a Person", U.S. Pat. No. 4,796,182 (Jan. 3, 1989 Duboff) "Diet Monitor and Display Device", U.S. Pat. No. 5,173,588 (Dec. 22, 1992 Harrah) "Food Consumption Monitor", U.S. Pat. No. 5,478,989 (Dec. 26, 1995 Shepley) "Nutritional Information System for Shoppers", U.S. Pat. No. 5,542,420 (Aug. 6, 1996 Goldman et al.) "Personalized Method and System for Storage, Communication, Analysis, and Processing of Health-Related Data", U.S. Pat. No. 5,673,691 (Oct. 7, 1997 Abrams et al.) "Apparatus to Control Diet and Weight Using Human Behavior Modification Techniques", U.S. Pat. No. 5,691,927 (Nov. 25, 1997 Gump) "Nutritional Aid and Method", U.S. Pat. No. 5,704,350 (Jan. 6, 1998 Williams) "Nutritional Microcomputer and Method", U.S. Pat. No. 5,729,479 (Mar. 17, 1998 Golan) "Multifunctional Diet Calculator", U.S. Pat. No. 5,836,312 (Nov. 17, 1998 Moore) "Computer-Assisted System and Method for Adjudging the Effect of Consumable Intakes on Physiological Parameters", U.S. Pat. No. 5,839,901 (Nov. 24, 1998 Karkanen) "Integrated Weight Loss Control Method", U.S. Pat. No. 5,841,115 (Nov. 24, 1998 Shepley) "Nutritional Information System for Shoppers", U.S. Pat. No. 5,890,128 (Mar. 30, 1999 Diaz et al.) "Personalized Hand Held Calorie Computer (ECC)", U.S. Pat. No. 5,989,188 (Nov. 23, 1999 Birkhoelzer) "Method and Apparatus for Determining the Energy Balance of a Living Subject on the Basis of Energy Used and Nutrition Intake", U.S. Pat. No. 6,024,281 (Feb. 15, 2000 Shepley) "Nutritional Information System for Shoppers", and U.S. Pat. No. 6,032,676 (Mar. 7, 2000 Moore) "Method for Correlating Consumable Intakes with Physiological Parameters".

Examples of prior art that appear to be best classified in this category also include: U.S. Pat. No. 6,040,531 (Mar. 21, 2000 Miller-Kovach) "Process For Controlling Body Weight", U.S. Pat. No. 6,083,006 (Jul. 4, 2000 Coffman) "Personalized Nutrition Planning", U.S. Pat. No. 6,095,949 (Aug. 1, 2000 Arai) "Health Management Device", U.S. Pat. No. 6,336,136 (Jan. 1, 2002 Harris) "Internet Weight Reduction System", U.S. Pat. No. 6,341,295 (Jan. 22, 2002 Stotler) "Virtual Reality Integrated Caloric Tabulator", U.S. Pat. No. 6,478,736 (Nov. 12, 2002 Mault) "Integrated Calorie Management System", U.S. Pat. No. 6,506,152 (Jan. 14, 2003 Lackey et al.) "Caloric Energy Balance Monitor", U.S. Pat. No. 6,553,386 (Apr. 22, 2003 Alabaster) "System and Method for Computerized Visual Diet Behavior Analysis and Training", U.S. Pat. No. 6,571,200 (May 27, 2003 Mault) "Monitoring Caloric Expenditure Resulting from Body Activity", U.S. Pat. No. 6,595,929 (Jul. 22, 2003 Stivoric et al.) "System for Monitoring Health Wellness and Fitness Having a Method and Apparatus for Improved Measurement of Heat Flow", U.S. Pat. No. 6,605,038 (Aug. 12, 2003 Teller et al.) "System for Monitoring Health, Wellness and Fitness", U.S. Pat. No. 6,635,015 (Oct. 21, 2003 Sagel) "Body Weight Management System", U.S. Pat. No. 6,675,041 (Jan. 6, 2004 Dickinson)

"Electronic Apparatus and Method for Monitoring Net Calorie Intake", U.S. Pat. No. 6,694,182 (Feb. 17, 2004 Yamazaki et al.) "Wearable Calorie Calculator", U.S. Pat. No. 6,745,214 (Jun. 1, 2004 Inoue et al.) "Calorie Control Apparatus with Voice Recognition", U.S. Pat. No. 6,856,938 (Feb. 15, 2005 Kurtz) "Weight Monitoring Computer", U.S. Pat. No. 6,878,885 (Apr. 12, 2005 Miller-Kovach) "Process for Controlling Body Weight", U.S. Pat. No. 6,917,897 (Jul. 12, 2005 Mork) "Food and Exercise Calculator", U.S. Pat. No. 7,020,508 (Mar. 28, 2006 Stivoric et al.) "Apparatus for Detecting Human Physiological and Contextual Information", U.S. Pat. No. 7,261,690 (Aug. 28, 2007 Teller et al.) "Apparatus for Monitoring Health, Wellness and Fitness", U.S. Pat. No. 7,285,090 (Oct. 23, 2007 Stivoric et al.) "Apparatus for Detecting, Receiving, Deriving and Displaying Human Physiological and Contextual Information", and U.S. Pat. No. 7,361,141 (Apr. 22, 2008 Nissila et al.) "Method and Device for Weight Management of Humans".

Examples of prior art that appear to be best classified in this category also include: U.S. Pat. No. 7,454,002 (Nov. 18, 2008 Gardner et al.) "Integrating Personal Data Capturing Functionality into a Portable Computing Device and a Wireless Communication Device", 7500937 (Mar. 10, 2009 Hercules) "Diet Compliance System", U.S. Pat. No. 7,689,437 (Mar. 30, 2010 Teller et al.) "System for Monitoring Health, Wellness and Fitness", U.S. Pat. No. 7,857,730 (Dec. 28, 2010 Dugan) "Methods and Apparatus for Monitoring and Encouraging Health and Fitness", U.S. Pat. No. 7,949,506 (May 24, 2011 Hill et al.) "Method for Determining and Compensating for a Weight Loss Energy Gap", U.S. Pat. No. 7,959,567 (Jun. 14, 2011 Stivoric et al.) "Device to Enable Quick Entry of Caloric Content", U.S. Pat. No. 8,073,707 (Dec. 6, 2011 Teller et al.) "System for Detecting Monitoring and Reporting an Individual's Physiological or Contextual Status", U.S. Pat. No. 8,075,451 (Dec. 13, 2011 Dugan) "Methods and Apparatus for Monitoring and Encouraging Health and Fitness", U.S. Pat. No. 8,087,937 (Jan. 3, 2012 Peplinski et al.) "System and Method for Monitoring Weight and Nutrition", U.S. Pat. No. 8,157,731 (Apr. 17, 2012 Teller et al.) "Method and Apparatus for Auto Journaling of Continuous or Discrete Body States Utilizing Physiological and/or Contextual Parameters", U.S. Pat. No. 8,180,592 (May 15, 2012 Yuen et al.) "Portable Monitoring Devices and Methods of Operating Same", U.S. Pat. No. 8,311,769 (Nov. 13, 2012 Yuen et al.) "Portable Monitoring Devices and Methods of Operating Same", and U.S. Pat. No. 8,311,770 (Nov. 13, 2012 Yuen et al.) "Portable Monitoring Devices and Methods of Operating Same".

Examples of prior art that appear to be best classified in this category also include U.S. patent applications: 20020133378 (Sep. 9, 2002 Mault et al.) "System and Method of Integrated Calorie Management", 20020156351 (Oct. 24, 2002 Sagel) "Body Weight Management System", 20030152607 (Aug. 14, 2003 Mault) "Caloric Management System and Method with Voice Recognition", 20030165799 (Sep. 4, 2003 Bisogno) "Computer Program, Method, and System for Monitoring Nutrition Content of Consumables and for Facilitating Menu Planning", 20030219513 (Nov. 27, 2003 Gordon) "Personal Nutrition Control Method", 20040034289 (Feb. 19, 2004 Teller et al.) "System for Monitoring Health, Wellness and Fitness", 20040133081 (Jul. 8, 2004 Teller et al.) "Method and Apparatus for Auto Journaling of Continuous or Discrete Body States Utilizing Physiological and/or Contextual Parameters", 20040133081 (Jul. 8, 2004 Teller et al.) "Method and Apparatus for Auto Journaling of Continuous or Discrete Body States Utilizing Physiological and/or Contextual Parameters", 20040152957 (Aug. 5, 2004 Stivoric et al.) "Apparatus for Detecting, Receiving, Deriving and Displaying Human Physiological and Contextual Information", 20050004436 (Jan. 6, 2005 Nissila et al.) "Method and Device for Weight Management of Humans", 20050008994 (Jan. 13, 2005 Bisogno) "Computer Program, Method, and System for Monitoring Nutrition Content of Consumables and for Facilitating Menu Planning", 20050113650 (May 26, 2005 Pacione et al.) "System for Monitoring and Managing Body Weight and Other Physiological Conditions Including Iterative and Personalized Planning . . . ", 20050247213 (Nov. 10, 2005 Slilaty) "Method of Identifying Particular Attributes of Food Products Consistent with Consumer Needs and/or Desires", 20050266385 (Dec. 1, 2005 Bisogno) "Computer Program, Method, and System for Monitoring Nutrition Content of Consumables and for Facilitating Menu Planning", 20060031102 (Feb. 9, 2006 Teller et al.) "System for Detecting Monitoring and Reporting an Individual's Physiological or Contextual Status", 20060036395 (Feb. 16, 2006 Shaya et al.) "Method and Apparatus for Measuring and Controlling Food Intake of an Individual", 20060074716 (Apr. 6, 2006 Tilles et al.) "System and Method for Providing Customized Interactive and Flexible Nutritional Counseling", and 20060122474 (Jun. 8, 2006 Teller et al.) "Apparatus for Monitoring Health Wellness and Fitness".

Examples of prior art that appear to be best classified in this category also include U.S. patent applications: 20060264730 (Nov. 23, 2006 Stivoric et al.) "Apparatus for Detecting Human Physiological and Contextual Information", 20070027366 (Feb. 1, 2007 Osburn) "Device and System for Entering and Monitoring Dietary Data", 20070089335 (Apr. 26, 2007 Smith et al.) "Nutrient Consumption/Expenditure Planning and Tracking Apparatus System and Method", 20070106129 (May 10, 2007 Srivathsa et al.) "Dietary Monitoring System for Comprehensive Patient Management", 20070179355 (Aug. 2, 2007 Rosen) "Mobile Self-Management Compliance and Notification Method, System and Computer Program Product", 20070208593 (Sep. 6, 2007 Hercules) "Diet Compliance System", 20080161654 (Jul. 3, 2008 Teller et al.) "Method and Apparatus for Auto Journaling of Body States and Providing Derived Physiological States Utilizing Physiological and/or Contextual Parameter", 20080161655 (Jul. 3, 2008 Teller et al.) ibid, 20080167536 (Jul. 10, 2008 Teller et al.) ibid, 20080167537 (Jul. 10, 2008 Teller et al.) ibid, 20080167538 (Jul. 10, 2008 Teller et al.) ibid, 20080167539 (Jul. 10, 2008 Teller et al.) ibid, 20080171920 (Jul. 17, 2008 Teller et al.) ibid, 20080171921 (Jul. 17, 2008 Teller et al.) ibid, 20080171922 (Jul. 17, 2008 Teller et al.) ibid, 20080275309 (Nov. 6, 2008 Stivoric et al.) "Input Output Device for Use with Body Monitor", 20090177068 (Jul. 9, 2009 Stivoric et al.) "Method and Apparatus for Providing Derived Glucose Information Utilizing Physiological and/or Contextual Parameters", 20090191514 (Jul. 30, 2009 Barnow) "Calorie Counter", 20100057564 (Mar. 4, 2010 Godsey et al.) "System and Method for Fitness Motivation", 20100062119 (Mar. 11, 2010 Miller-Kovach) "Processes and Systems for Achieving and Assisting in Improved Nutrition", 20100062402 (Mar. 11, 2010 Miller-Kovach) "Processes and Systems Using and Producing Food Healthfulness Data Based on Linear Combinations of Nutrients", 20100079291 (Apr. 1, 2010 Kroll et al.) "Personalized Activity Monitor and Weight Management System", 20100080875 (Apr. 1, 2010 Miller-Kovach) "Processes and Systems for Achieving and Assisting in Improved Nutrition Based on Food Energy Data and Relative Healthfulness Data", and 20100228160 (Sep. 9, 2010 Schweizer) "Apparatus for Activity Monitoring".

Examples of prior art that appear to be best classified in this category also include U.S. patent applications: 20110087137 (Apr. 14, 2011 Hanoun) "Mobile Fitness and Personal Caloric Management System", 20120031805 (Feb. 9, 2012 Stolarczyk) "Daily Meal Planning System", 20120072233 (Mar. 22, 2012 Hanlon et al.) "Medical Health Information System for Health Assessment, Weight Management and Meal Planning", 20120083669 (Apr. 5, 2012 Abujbara) "Personal Nutrition and Wellness Advisor", 20120083705 (Apr. 5, 2012 Yuen et al.) "Activity Monitoring Systems and Methods of Operating Same", 20120083714 (Apr. 5, 2012 Yuen et al.) "Activity Monitoring Systems and Methods of Operating Same", 20120083715 (Apr. 5, 2012 Yuen et al.) "Portable Monitoring Devices and Methods of Operating Same", 20120083716 (Apr. 5, 2012 Yuen et al.) "Portable Monitoring Devices and Methods of Operating Same", 20120084053 (Apr. 5, 2012 Yuen et al.) "Portable Monitoring Devices and Methods of Operating Same", 20120084054 (Apr. 5, 2012 Yuen et al.) "Portable Monitoring Devices and Methods of Operating Same", 20120096405 (Apr. 19, 2012 Seo) "Apparatus and Method for Diet Management", 20120126983 (May 24, 2012 Breibart) "Method and Associated Device for Personal Weight Control or Weight Loss", 20120221495 (Aug. 30, 2012 Landers) "Digital Weight Loss Aid", 20120226471 (Sep. 6, 2012 Yuen et al.) "Portable Monitoring Devices and Methods of Operating Same", 20120226472 (Sep. 6, 2012 Yuen et al.) "Portable Monitoring Devices and Methods of Operating Same", 20120295233 (Nov. 22, 2012 Cooperman) "Computerized System and Method for Monitoring Food Consumption", 20120316932 (Dec. 13, 2012 Rahman et al.) "Wellness Application for Data-Capable Band", 20120317167 (Dec. 13, 2012 Rahman et al.) "Wellness Application for Data-Capable Band", 20130002435 (Jan. 3, 2013 Utter) "Sleep Management Method and Apparatus for a Wellness Application Using Data from a Data-Capable Band", 20130006063 (Jan. 3, 2013 Wang) "Physiological Condition, Diet and Exercise Plan Recommendation and Management System", 20130006125 (Jan. 3, 2013 Kroll et al.) "Personalized Activity Monitor and Weight Management System", and 20130029807 (Jan. 31, 2013 Amsel) "Health Tracking Program".

2. Consumed Manufactured Compound or Specifically-Isolated Natural Substance

Prior art in this category includes manufactured compounds and specifically-isolated natural substances that are either added to food as an ingredient during food preparation or are consumed independently of food consumption in order to modify a person's food consumption. This category includes pharmaceuticals and specific food ingredients that are intended as appetite suppressants. For many years people have been seeking a "magic" pill that can address obesity with good results and tolerable side effects.

There are many examples of prior art in this category and we have only included those which appear to be most relevant. For the purposes of this categorization, we have created a separate subsequent category for substances which a person can sprinkle on food at the time of consumption. We have also included separate categories for inventions whose primary therapeutic modality is a device, but which also emit or elude a drug as a secondary mode of action. The success of art in this category for modifying food consumption depends on the substance's ability to actually modify the person's food consumption without intolerable side effects. Compliance and effectiveness can be problematic, especially if a drug's side effects are very unpleasant.

Examples of prior art that appear to be best classified in this category include: U.S. Pat. No. 4,159,347 (Jun. 26, 1979 Yoshida et al.) "Flavoring with Cyclic Acetals of 2-Methyl-2-Pentenal", U.S. Pat. No. 4,210,637 (Jul. 1, 1980 Wurtman et al.) "Composition and Method for Suppressing Appetite for Calories as Carbohydrates", U.S. Pat. No. 4,491,578 (Jan. 1, 1985 Peikin) "Method of Stimulating Satiety in Mammals", U.S. Pat. No. 4,497,798 (Feb. 5, 1985 Lambert) "Appetite Suppressant", U.S. Pat. No. 4,689,235 (Aug. 25, 1987 Barnes et al.) "Encapsulation Matrix Composition and Encapsulate Containing Same", U.S. Pat. No. 4,740,365 (Apr. 26, 1988 Yukimatsu et al.) "Sustained-Release Preparation Applicable to Mucous Membrane in Oral Cavity", U.S. Pat. No. 5,013,716 (May 7, 1991 Cherukuri et al.) "Unpleasant Taste Masking Compositions and Methods for Preparing Same", U.S. Pat. No. 5,290,808 (Mar. 1, 1994 Sofia) "Method to Control the Intake of Food", U.S. Pat. No. 5,405,641 (Apr. 11, 1995 Kurihara et al.) "Taste-Modification Composition and Method for Stabilizing Taste-Modifier", U.S. Pat. No. 5,472,685 (Dec. 5, 1995 Gaffar) "Antiplaque Oral Compositions", U.S. Pat. No. 5,605,698 (Feb. 25, 1997 Ueno) "Oral Composition", U.S. Pat. No. 5,858,967 (Jan. 12, 1999 Weigle et al.) "Appetite Supression Factor and Related Methods", U.S. Pat. No. 6,123,980 (Sep. 26, 2000 Pearson et al.) "Preparing Granulated Sugar Blends and Products", U.S. Pat. No. 6,207,638 (Mar. 27, 2001 Portman) "Nutritional Intervention Composition for Enhancing and Extending Satiety", U.S. Pat. No. 6,224,873 (May 1, 2001 Jones) "Regulation of Appetite Body Weight and Athletic Function with Materials Derived from Citrus Varieties", U.S. Pat. No. 6,235,274 (May 22, 2001 Lou et al.) "Microparticles Which Controllably Release Olfactorily Active Substances Methods of Using Same and Processes for Preparing Same", U.S. Pat. No. 6,248,390 (Jun. 19, 2001 Stillman) "Fiber-Water: Water Containing Soluble Fiber", U.S. Pat. No. 6,319,523 (Nov. 20, 2001 Zhou) "Composition and Method for Inhibiting Oral Bacteria", U.S. Pat. No. 6,376,657 (Apr. 23, 2002 Van Heerden et al.) "Pharmaceutical Compositions Having Appetite Suppressant Activity", U.S. Pat. No. 6,413,545 (Jul. 2, 2002 Alviar et al.) "Diet Composition and Method of Weight Management", U.S. Pat. No. 6,610,277 (Aug. 26, 2003 Zuckerman) "Appetite Suppressant Toothpaste", and U.S. Pat. No. 6,861,405 (Mar. 1, 2005 Desir et al.) "Compositions and Methods Relating to Glucose Metabolism, Weight Control, and Food Intake".

Examples of prior art that appear to be best classified in this category also include: U.S. Pat. No. 6,942,848 (Sep. 13, 2005 Nelson et al.) "Cyclodextrins in Dental Products", U.S. Pat. No. 7,025,984 (Apr. 11, 2006 Jandacek et al.) "Compositions and Methods for Body Weight Management", U.S. Pat. No. 7,115,297 (Oct. 3, 2006 Stillman) "Nutritionally Fortified Liquid Composition with Added Value Delivery Systems/Elements/Additives", U.S. Pat. No. 7,138,107 (Nov. 21, 2006 Adams et al) "Inhibition of Olfactory Neurosensory Function to Treat Eating Disorders and Obesity", U.S. Pat. No. 7,229,658 (Jun. 12, 2007 Inoue et al.) "Compositions Containing Sucralose and Application Thereof", U.S. Pat. No. 7,238,380 (Jul. 3, 2007 Stillman) "Water Containing Soluble Fiber", U.S. Pat. No. 7,276,229 (Oct. 2, 2007 Baker et al.) "Oral Compositions", U.S. Pat. No. 7,402,400 (Jul. 22, 2008 Zuker et al.) "Mammalian Sweet Taste Receptors", U.S. Pat. No. 7,524,877 (Apr. 28, 2009 Rosenfeld et al.) "Compounds for Use in Weight Loss and Appetite Suppression in Humans", U.S. Pat. No. 7,541,356 (Jun. 2, 2009 Rosenfeld et al.) "Compounds for Use in Weight Loss and Appetite Suppression in Humans", U.S. Pat. No. 7,632,517 (Dec. 15, 2009 Dugger et al.) "Buccal Polar and Non-Polar Spray Containing Zolpidem", U.S. Pat. No. 7,851,005 (Dec. 14, 2010 Bingley et al.) "Taste Potentiator Compositions and Beverages Containing Same", U.S. Pat. No. 7,851,006 (Dec. 14, 2010 Bingley et al.)

"Taste Potentiator Compositions and Beverages Containing Same", U.S. Pat. No. 7,879,376 (Feb. 1, 2011 Boghani et al.) "Taste Potentiator Compositions and Edible Confectionery and Chewing Gum Products Containing Same", U.S. Pat. No. 7,977,060 (Jul. 12, 2011 Zuker et al.) "Mammalian Sweet Taste Receptors", U.S. Pat. No. 8,119,359 (Feb. 21, 2012 Adler et al.) "Methods of Indentifying Sweet Taste Modulators", U.S. Pat. No. 8,143,215 (Mar. 27, 2012 Hirsch) "Method of Promoting Weight Loss", U.S. Pat. No. 8,198,048 (Jun. 12, 2012 Zuker et al.) "Mammalian Sweet Taste Receptors", U.S. Pat. No. 8,217,001 (Jul. 10, 2012 Cowley et al.) "Modification of Feeding Behavior", U.S. Pat. No. 8,236,285 (Aug. 7, 2012 Dugger et al.) "Buccal, Polar and Non-Polar Spray Containing Zolpidem", and U.S. Pat. No. 8,287,898 (Oct. 16, 2012 Jandacek et al.) "Compositions and Methods for Body Weight Management".

Examples of prior art that appear to be best classified in this category also include U.S. patent applications: 20020187204 (Dec. 12, 2002 Alviar et al.) "Diet Composition and Method of Weight Management", 20030113310 (Jun. 19, 2003 Van Laere et al.) "Method for the Treatment of Obesity, Overweight and Fluctuations in Blood Insuline and/or Glucose Levels", 20040071801 (Apr. 15, 2004 Edell et al.) "Herbal Formulation of Gymnema Sylvestre as a Dietary Aid", 20040156920 (Aug. 12, 2004 Kane) "Extracts From Plant and Non-Plant Biomass and Uses Thereof", 20040192760 (Sep. 30, 2004 Whittle et al.) "Pharmaceutical Formulations", 20040247702 (Dec. 9, 2004 Rajendran et al.) "Caralluma Extract Products and Processes for Making the Same", 20050053555 (Mar. 10, 2005 Pederson) "Appetite Control Compositions and Methods of Use", 20060105068 (May 18, 2006 Fleischner) "Dietary Supplement Formulations Containing Hoodia Gordonii", 20060193795 (Aug. 31, 2006 Zuckerman) "Appetite Suppressant Mouth Spray", 20070104805 (May 10, 2007 Udell) "Compositions of Hoodia Gordonii and Pinolenic Acid Derivatives", 20070160735 (Jul. 12, 2007 Stillman) "Water Containing Soluble Fiber", 20070196436 (Aug. 23, 2007 Abrahams et al.) "Process for Preparing an Edible Composition Comprising Steroidal Glycosides", 20080014327 (Jan. 17, 2008 Stillman) "Water Containing Soluble Fiber", 20080102143 (May 1, 2008 Freis et al.) "Uses for the Extract of a Plant of the Family Asclepiadaceae", 20080138447 (Jun. 12, 2008 Riggins et al.) "Method for Administering Appetite Suppressant and Composition Thereof", 20080152705 (Jun. 26, 2008 Udell et al.) "Corosolic Acid Formulation and Its Application for Weight-Loss Management and Blood Sugar Balance", and 20080255093 (Oct. 16, 2008 Tam et al.) "Compositions and Methods for Treating Obesity and Related Disorders".

Examples of prior art that appear to be best classified in this category also include U.S. patent applications: 20100098783 (Apr. 22, 2010 Sommerfeld et al.) "Appetite Suppressant Composition", 20100215584 (Aug. 26, 2010 Passe) "Compositions and Methods of Modulating the Taste and Smell Receptors and Screening Methods Therefore", 20100267643 (Oct. 21, 2010 Baron et al.) "Chemosensory Receptor Ligand-Based Therapies", 20100316768 (Dec. 16, 2010 Stillman) "Nutritionally Fortified Liquid Composition with Added Value Delivery Systems/Elements/Additives", 20110065660 (Mar. 17, 2011 Baron et al.) "Chemosensory Receptor Ligand-Based Therapies", 20110082407 (Apr. 7, 2011 Aronne) "Combination Therapies for the Treatment of Obesity", 20110104336 (May 5, 2011 Stillman) "Water Containing Soluble Fiber", 20110136909 (Jun. 9, 2011 Imada et al.) "Method for Suppressing Excessive Appetite", 20110166065 (Jul. 7, 2011 Bhanot et al.) "Modulation Of Glucose-6-Phosphatase Translocase Expression", 20110224155 (Sep. 15, 2011 Tachdjian et al.) "Modulation of Chemosensory Receptors and Ligands Associated Therewith", 20110230502 (Sep. 22, 2011 Tachdjian et al.) "Modulation of Chemosensory Receptors and Ligands Associated Therewith", 20110244514 (Oct. 6, 2011 Zuker et al.) "Mammalian Sweet Taste Receptors", 20120040893 (Feb. 16, 2012 Cowley et al.) "Modification of Feeding Behaviour", 20120094942 (Apr. 19, 2012 Baron et al.) "Chemosensory Receptor Ligand-Based Therapies", 20120115778 (May 10, 2012 Karsenty et al.) "Methods of Suppressing Appetite by the Administration of Antagonists of the Serotonin HTR1a or HTR2b Receptors or Inhibitors of TPH2", 20120157409 (Jun. 21, 2012 Cherkassky) "Appetite Suppressant Product and Method", 20120177730 (Jul. 12, 2012 Baron et al.) "Chemosensory Receptor Ligand-Based Therapies", and 20120208748 (Aug. 16, 2012 Chen et al.) "Peptide Compositions and Methods for Treating Patients". Examples of prior art that appear to be best classified in this category also include EP 1685834 "Use of Pinolenic Acid for the Treatment Of Obesity" and EP 2072048 "Use of Pinolenic Acid for the Treatment Of Obesity".

3. Substance Sprinkled on Food

Prior art in this category includes manufactured and specifically-isolated substances or compounds that a person voluntarily adds to their food slightly before or during food consumption in order to modify their food consumption. For example, this category includes substances that a person sprinkles on their food with the intent of suppressing their appetite. In various examples, such a substance can change the flavor, smell, or appearance of food with the intent of dampening a person's appetite.

The success of art in this category in modifying food consumption depends on the ability of the sprinkled substance to actually modify the person's food consumption and the consistency with which the person regularly sprinkles the substance on food each time they eat. This can be problematic, especially if the substance makes food taste less appealing or if a specific food has a surface to which the sprinkled substance does not adhere. Also, if a person does not have enough willpower and discipline to avoid eating unhealthy food in the first place, then it is not clear that this person would have enough willpower and discipline to always sprinkle an appetite-suppressing additive on their food each time that they eat.

Examples of prior art that appear to be best classified in this category include: U.S. Pat. No. 5,603,971 (Feb. 18, 1997 Porzio et al.) "Encapsulation Compositions", U.S. Pat. No. 6,112,749 (Sep. 5, 2000 Hall et al.) "Flavor Dot Odorizer and Method", U.S. Pat. No. 6,902,751 (Jun. 7, 2005 Schleifenbaum et al.) "Encapsulated Flavorings", U.S. Pat. No. 7,727,546 (Jun. 1, 2010 Moneymaker et al.) "Nutrient System for Individualized Responsive Dosing Regimens", U.S. Pat. No. 7,820,208 (Oct. 26, 2010 Hirsch) "Method of Assaying Satiety Enhancing Tastants (Alan Hirsch)", U.S. Pat. No. 8,143,062 (Mar. 27, 2012 Hirsch) "Method and Composition for Enhancing Weight Loss", and U.S. Pat. No. 8,143,215 (Mar. 27, 2012 Hirsch) "Method of Promoting Weight Loss"; and U.S. patent applications 20040231299 (Nov. 25, 2004 Yakushigawa et al.) "Flavoring System and Method", 20080075813 (Mar. 27, 2008 Smith et al.) "Seasoning and Method for Enhancing and Potentiating Food Flavor Utilizing Microencapsulation While Reducing Dietary Sodium Intake", 20090123380 (May 14, 2009 Hirsch) "Method of Assaying Satiety Enhancing Tastants (Alan Hirsch)", 20090123524 (May 14, 2009 Hirsch) "Packaged Satiety Enhancing Composition (Alan Hirsch)", 20090123579 (May 14, 2009 Hirsch) "Method of Promoting Weight Loss (Alan Hirsh)", 20090214445 (Aug. 27, 2009 Boghani et al.) "Delivery Systems for Managing Release of Functional Ingredients in an Edible Composition", and 20120058217 (Mar. 8, 2012 Patty) "Taste Deterrent and Diet Method".

4. Manually-Administered Spray or Pulse

This category of prior art includes oral and nasal sprays, mists, and pulses that contain a consumption-modifying substance. As was the case with art involving a sprinkled food additive, the success of art in this category depends on the ability of the sprayed substance to actually modify a person's food consumption and the regularity with which the person sprays the substance into their mouth or nose every time that they eat. In an example, a sprayed substance can be absorbed into tissue for a systemic (pharmacologic) appetite-suppressant effect. In another example, a sprayed substance can be released into a person's oral cavity or nasal cavities for a localized anesthetic effect. In an example, this substance can mask or block the taste or smell of food.

In order for this approach to work, a person must exercise consistent voluntary compliance in spraying the substance into their mouth or nose prior to consumption of (selected types of) food. However, if a person does not have enough willpower and discipline to avoid eating unhealthy food in the first place, then it is not clear that this person would have enough willpower and discipline to consistently spray something into their nose or mouth before every meal or snack.

Examples of prior art that appear to be best classified in this category include: U.S. Pat. No. 4,935,225 (Jun. 19, 1990 Curtis et al.) "Appetite Suppressant Dentifrice", U.S. Pat. No. 5,284,132 (Feb. 8, 1994 Geier) "Device for the Transnasal or Oral Administration of Drugs or the Like", U.S. Pat. No. 5,456,677 (Oct. 10, 1995 Spector) "Method for Oral Spray Administration of Caffeine", U.S. Pat. No. 6,715,485 (Apr. 6, 2004 Djupesland) "Nasal Delivery Device", U.S. Pat. No. 7,935,065 (May 3, 2011 Martin et al.) "Oral Device", and patent application 20050037031 (Feb. 17, 2005 Jackson) "Methods for Diet and Weight Control by Altering the Senses of Smell and Taste".

5. Substance-Emitting Lipstick or Toothpaste

This category of prior art includes lipstick or toothpaste that releases a consumption-modifying substance. In order to be effective, the lipstick or toothpaste must release a genuinely consumption-modifying substance in sufficient amounts over a long-enough duration to affect food consumption. If it only releases the substance for a short time or tapers off rapidly, then the lipstick or toothpaste must be applied frequently which relies heavily on the person's voluntary compliance. If it releases the substance for a long time, then the prior art does not disclose how this approach would enable selective modification of unhealthy food consumption; it would affect consumption of healthy foods as well as unhealthy foods. In order for this approach to be effective: the substance in the lipstick or toothpaste must really reduce food consumption when used; the substance must be released from the lipstick or toothpaste in sufficient quantity, and over a sufficient duration, to be effective; and the person must have consistent voluntary compliance in using the lipstick or toothpaste. Also, many people do not wear lipstick. For these reasons, art in this category is limited for consistent modification of food consumption.

Examples of prior art that appear to be best classified in this category include: U.S. Pat. No. 6,485,710 (Nov. 26, 2002 Zuckerman) "Appetite Suppressant Toothpaste" and U.S. Pat. No. 7,247,323 (Jul. 24, 2007 George et al.) "Delivery System for Appetite Suppressant"; and U.S. patent applications 20030095936 (May 22, 2003 Light) "Lip Gloss Composition", 20070042058 (Feb. 22, 2007 George et al.) "Delivery System for Appetite Suppressant", and 20100135945 (Jun. 3, 2010 Murdock et al.) "Gymnema-Containing Lip Balm Compositions and Associated Method".

6. Substance-Emitting Adhesive Patch in the Mouth

Prior art in this category includes temporary substance-emitting patches that a person attaches (e.g. through adhesion) within their oral cavity in order to modify their food consumption. In various examples, such a patch can be attached to a person's upper palate or teeth. In an example, this substance can be absorbed into tissue (such as through mucosal delivery) to cause a systemic (pharmacological) appetite-suppressant effect. In an example, this substance can be released into the person's oral cavity or nasal cavity to cause a localized anesthetic effect. The intent is to reduce a person's appetite by gradual emission of an appetite-suppressing substance.

The success of this approach depends on: whether the person regularly uses and replaces the patch, whether the patch emits the substance for a sufficiently long time and in a sufficiently consistent dosage to affect all of a person's meals throughout the day, and whether the substance actually reduces the person's appetite even when consistently emitted. If the effect of the patch lasts for a short time, then the patch must be replaced frequently, which requires high voluntary compliance by the person. If the effect lasts for a long time, then the prior art does not disclose how this approach would enable selective consumption modification (allowing healthy food but discouraging unhealthy food). All of these factors make this approach problematic.

Examples of prior art that appear to be best classified in this category include: U.S. Pat. No. 3,972,995 (Aug. 3, 1976 Tsuk et al.) "Dosage Form", U.S. Pat. No. 4,059,686 (Nov. 22, 1977 Tanaka et al.) "Pharmaceutical Preparation for Oral Cavity Administration", U.S. Pat. No. 4,292,299 (Sep. 29, 1981 Suzuki et al.) "Slow-Releasing Medical Preparation to be Administered by Adhering to a Wet Mucous Surface", U.S. Pat. No. 4,615,697 (Oct. 7, 1986 Robinson) "Bioadhesive Compositions and Methods of Treatment Therewith", U.S. Pat. No. 4,764,378 (Aug. 16, 1988 Keith et al.) "Buccal Drug Dosage Form", U.S. Pat. No. 6,387,408 (May 14, 2002 Illum et al.) "Adhesive Drug Delivery Composition", U.S. Pat. No. 6,488,953 (Dec. 3, 2002 Halliday et al.) "Oral Transmucosal Delivery", and U.S. Pat. No. 8,173,113 (May 8, 2012 Scholz et al.) "Bioadhesive Composition and Patch"; and U.S. patent applications 20040109886 (Jun. 10, 2004 Rigby) "Methods and Apparatus for Transdermal Delivery of Abusable Drugs with a Deterrent Agent", 20070104783 (May 10, 2007 Domb et al.) "Double-Layered Absorbable Solid Compositions for the Topical Treatment of Oral Mucosal Disorders", 20090130178 (May 21, 2009 Oronsky et al.) "Formulation for Decreasing Tobacco, Alcohol, Drug or Food Consumption", and 20120015021 (Jan. 19, 2012 Mizrahi et al.) "Anti-Appetite Adhesive Compositions".

7. Dissolving Film in Mouth

This category of prior art includes dissolvable films which a person inserts into their mouth and which slowly release a consumption-modifying substance. Unlike art in the prior category, these films are not attached to tissue within a person's oral cavity. Since inserting and ingesting the film can interfere with the process of food consumption, a person must have sufficient willpower and discipline to insert the film in advance of eating. Further, if the substance in the mouth is diluted by food consumption, then the person may have to insert a dissolvable film multiple times during the same meal.

In order for this approach to work, the person must exercise consistent voluntary compliance in inserting the film into their mouth before eating (selected types of) food. However, if a person does not have enough willpower and discipline to avoid eating unhealthy food in the first place, then it is not clear that this person would have enough willpower and discipline to consistently insert a dissolvable film into their mouth before each snack or meal.

Examples of prior art that appear to be best classified in this category include: U.S. Pat. No. 6,419,903 (Jul. 16, 2002 Xu et al.) "Breath Freshening Film" and U.S. Pat. No. 7,972,618 (Jul. 5, 2011 Fuisz et al.) "Edible Water-Soluble Film Containing a Foam Reducing Flavoring Agent"; and patent application 20040131661 (Jul. 8, 2004 Auffret et al.) "Process for Making Orally Consumable Dosage Forms".

8. Tablet or Gum in Mouth

This category of prior art includes tablets, lozenges, and chewing gum that are inserted into the mouth and slowly release a consumption-modifying substance. Since inserting and ingesting a tablet, lozenge, or chewing gum can interfere with the process of food consumption, the person must have sufficient willpower and discipline to insert the tablet, lozenge, or chewing gum well in advance of eating. Further, if the substance in the mouth is diluted by food consumption, then the person may have to insert a tablet, lozenge, or chewing gum multiple times during the same meal.

In order for this approach to work, the person must exercise consistent voluntary compliance in inserting the tablet, lozenge, or chewing gum into their mouth before eating (selected types of) food. However, if a person does not have enough willpower and discipline to avoid eating unhealthy food in the first place, then it is not clear that this person would have enough willpower and discipline to consistently pop a tablet, lozenge, or chewing gum into their mouth before each snack or meal.

Examples of prior art that appear to be best classified in this category include: U.S. Pat. No. 3,856,942 (Dec. 24, 1974 Murphy) "Appetite Control Composition", U.S. Pat. No. 3,911,099 (Oct. 7, 1975 Defoney et al.) "Long-Acting Articles for Oral Delivery and Process", U.S. Pat. No. 4,039,653 (Aug. 2, 1977 Defoney et al.) "Long-Acting Articles for Oral Delivery and Process", U.S. Pat. No. 4,822,597 (Apr. 18, 1989 Faust et al.) "Anesthetic-Containing Chewing Gum Compositions", U.S. Pat. No. 5,942,244 (Aug. 24, 1999 Friedman et al.) "Local Oral Herbal Slow Release Tablets", U.S. Pat. No. 6,183,775 (Feb. 6, 2001 Ventouras) "Buccal Delivery System", U.S. Pat. No. 6,280,761 (Aug. 28, 2001 Santus) "Nicotine Lozenge (Santus)", U.S. Pat. No. 6,893,654 (May 17, 2005 Pinney et al.) "Two-Stage Transmucosal Medicine Delivery System for Symptom Relief", U.S. Pat. No. 6,949,264 (Sep. 27, 2005 Mcgrew et al.) "Nutraceuticals or Nutritional Supplements and Method of Making", U.S. Pat. No. 7,851,000 (Dec. 14, 2010 Boghani et al.) "Taste Potentiator Compositions and Edible Confectionery and Chewing Gum Products Containing Same", and U.S. Pat. No. 8,236,348 (Aug. 7, 2012 Gin et al.) "Long-Lasting, Flavored Dosage Forms for Sustained Release of Beneficial Agents within the Mouth"; and U.S. patent applications 20040151771 (Aug. 5, 2004 Gin et al.) "Long-Lasting, Flavored Dosage Forms for Sustained Release of Beneficial Agents Within the Mouth", 20040247669 (Dec. 9, 2004 Gin et al.) "Long-Lasting Flavored Dosage Forms for Sustained Release of Beneficial Agents within the Mouth", 20050112149 (May 26, 2005 Belote et al.) "Single-Dose Taste Inhibitor Units", 20070048369 (Mar. 1, 2007 Foreman et al.) "Mucosal Delivery Tablet", 20090081291 (Mar. 26, 2009 Gin et al.) "Sustained Release Dosage Forms for Delivery of Agents to an Oral Cavity of a User", and 20120195954 (Aug. 2, 2012 Maynard) "Method of Reducing Appetite".

9. Intraoral Drug Delivery

Prior art in this category includes pharmaceutical compounds that are delivered intra-orally. In an example, a compound can be delivered locally (e.g. by injection) in order to selectively target intraoral tissue. In another example, a compound can be delivered systemically via mucosal absorption. This approach depends on the ability of the pharmaceutical compound to actually reduce a person's appetite and on patient compliance with intra-oral drug administration.

Examples of prior art that appear to be best classified in this category include: U.S. Pat. No. 5,194,003 (Mar. 16, 1993 Garay et al.) "Removable Device for Delivering Beneficial Agents Orally" and U.S. Pat. No. 8,181,655 (May 22, 2012 Bardach et al.) "Therapeutic and Protective Dental Device Useful as an Intra-Oral Delivery System"; and patent application 20080044797 (Feb. 21, 2008 Bardach et al.) "Inserts for Use with Oral Appliances".

10. Motion Guided or Directed Pill

Prior art in this category includes "smart pills" whose movement, placement, attachment, and/or activation within specific body structures can be remotely guided and controlled. In an example, such pills can be guided to a particular location along a person's gastrointestinal tract and then activated when they reach this location. Such activation can include remote-controlled attachment to specific body tissue and/or remote-controlled localized emission of a pharmaceutical compound. In an example, local intragastric drug delivery can be more targeted and effective than systemic drug delivery.

Examples of prior art that appear to be best classified in this category include: U.S. Pat. No. 8,109,920 (Feb. 7, 2012 Boyden et al.) "Medical or Veterinary Digestive Tract Utilization Systems and Methods", U.S. Pat. No. 8,219,171 (Jul. 10, 2012 Benoist) "Delivery Device for Implantable Monitor", U.S. Pat. No. 8,303,573 (Nov. 6, 2012 Boyden et al.) "Medical or Veterinary Digestive Tract Utilization Systems and Methods", and U.S. Pat. No. 8,333,754 (Dec. 18, 2012 Boyden et al.) "Medical or Veterinary Digestive Tract Utilization Systems and Methods"; and U.S. patent applications 20110160129 (Jun. 30, 2011 Imran) "Therapeutic Agent Preparations for Delivery Into a Lumen of the Intestinal Tract Using a Swallowable Drug Delivery Device", 20110160699 (Jun. 30, 2011 Imran) "Swallowable Drug Delivery Device and Methods of Drug Delivery", 20120010590 (Jan. 12, 2012 Imran) "Swallowable Drug Delivery Device and Method of Delivery", 20120165792 (Jun. 28, 2012 Ortiz et al.) "Pill Catchers", 20120165793 (Jun. 28, 2012 Ortiz et al.) "Pill Catchers", 20120165794 (Jun. 28, 2012 Ortiz et al.) "Pill Catchers", and 20120165796 (Jun. 28, 2012 Ortiz et al.) "Pill Catchers".

11. General Implanted Drug Pump

This category of prior art includes implantable drug pumps that are used to achieve a consumption-modifying effect. Not all implantable drug pumps are reviewed here, only those which are particularly relevant to modification of food consumption and related metabolic processes. In an example, an implantable pump can pump a drug into a location along the person's digestive tract. In an example, an implantable drug pump can pump a pharmaceutical agent into a person's brain. In an example, an implantable pump can deliver a pharmaceutical agent into a person's blood stream. For implanted medical devices for which drug delivery appears to be the secondary mode of action, we have included such art in separate categories which follow that are primarily identified by their primary (non-drug device) mode of action.

It is not clear from the prior art how such drug pumps can be selectively used to allow consumption of healthy food, but discourage consumption of unhealthy food. Also, the prior art does not disclose how such devices could be used to allow moderate consumption, but limit excess consumption, of certain foods. Prior art in this category is much less dependent on patient compliance than art in many of the previous categories, but still critically depends on the effectiveness of a drug in modifying food consumption and/or absorption without intolerable side effects.

Examples of prior art that appear to be best classified in this category include: U.S. Pat. No. 4,925,446 (May 15, 1990 Garay et al.) "Removable Inflatable Intragastrointestinal Device for Delivering Beneficial Agents", U.S. Pat. No. 5,011,472 (Apr. 30, 1991 Aebischer et al.) "Implantable Delivery System for Biological Factors", U.S. Pat. No. 5,318,519 (Jun. 7, 1994 Wilk) "Method and Apparatus for Supplying Nutrition", U.S. Pat. No. 5,643,207 (Jul. 1, 1997 Rise) "Implantable Techniques for Infusing a Therapeutic Agent with Endogenous Bodily Fluid", U.S. Pat. No. 5,730,722 (Mar. 24, 1998 Wilk) "Method and Apparatus for Supplying a Medical Treatment Composition to a Patient", U.S. Pat. No. 7,043,295 (May 9, 2006 Starkebaum) "Methods and Apparatus for Delivering a Drug Influencing Appetite for Treatment of Eating Disorders", U.S. Pat. No. 7,108,680 (Sep. 19, 2006 Rohr et al.) "Closed-Loop Drug Delivery System", U.S. Pat. No. 7,790,671 (Sep. 7, 2010 Stojanovic-Susulic et al.) "Implantable Pump for Protein Delivery for Obesity Control by Drug Infusion into the Brain", U.S. Pat. No. 8,066,689 (Nov. 29, 2011 Mitelberg et al.) "Methods and Systems for Submucosal Implantation of a Device for Diagnosis and Treatment with a Therapeutic Agent", and U.S. Pat. No. 8,252,744 (Aug. 28, 2012 Stojanovic-Susulic et al.) "Implantable Pump for Protein Delivery for Obesity Control by Drug Infusion into the Brain"; and U.S. patent applications 20030171711 (Sep. 11, 2003 Rohr et al.) "Closed-Loop Drug Delivery System", 20050038415 (Feb. 17, 2005 Rohr et al.) "Method and Apparatus for the Treatment of Obesity", 20050096514 (May 5, 2005 Starkebaum) "Gastric Activity Notification", 20070082843 (Apr. 12, 2007 Stojanovic-Susulic et al.) "Implantable Pump for Protein Delivery for Obesity Control by Drug Infusion into the Brain", 20100145301 (Jun. 10, 2010 Magal) "Spray Administration of Compositions Including Active Agents Such as Peptides to the Gastrointestinal Tract", and 20120071812 (Mar. 22, 2012 Mitelberg et al.) "Methods and Systems for Submucosal Implantation of a Device for Diagnosis and Treatment with a Therapeutic Agent".

Examples of prior art that appear to be best classified in this category also include EP 1504778 "Implantable Pump for the Treatment of Obesity", WO 2002085428 ("Implantable Osmotic Pump"), and WO 2003004034 ("Method for Inducing Analgesia Comprising Administration Alternatively of an Opioid Receptor Agonist and an Opioid Receptor Like Receptor 1 Agonist . . . ").

12. Food Purchasing Monitoring

Prior art in this category includes devices and methods that monitor what types of food a person purchases at the point of sale. Although there can be overlap, in some respects most art in this category is based on information technology, not biomedical technology. It is relatively easy to track food purchase transactions at a given store or with a given credit card. It can also be relatively easy to record the many items in a store that are marked with a bar code (or other type of product identifier).

However, this approach depends on two large assumptions. First, it assumes that a person buys everything that they eat at participating locations or with a selected card. This is violated if a person buys food at a non-participating location or eats food that someone else has bought. Second, it assumes that a person eats everything that they buy. This is violated if the person buys food for others (such as their family) and/or does not eat all the food that they buy. Also, timing differences between when a person buys food and when they eat that food can confound analysis of the relationship between food consumption and achievement of weight management objectives.

Examples of prior art that appear to be best classified in this category include: U.S. Pat. No. 5,412,564 (May 2, 1995 Ecer) "System and Method for Diet Control", U.S. Pat. No. 7,769,635 (Aug. 3, 2010 Simons-Nikolova) "Weight Management System with Simple Data Input", and U.S. Pat. No. 7,999,674 (Aug. 16, 2011 Kamen) "Device and Method for Food Management"; and U.S. patent applications 20080255955 (Oct. 16, 2008 Simons-Nikolova) "Weight Management System with Simple Data Input", 20100205209 (Aug. 12, 2010 Jokinen) "Method and System for Monitoring a Personal Intake", and 20130006807 (Jan. 3, 2013 Bai et al.) "Guideline-Based Food Purchase Management".

13. Food Scale

Prior art in this category includes automated food scales with a computer interface that records the weight of a specific portion of food before it is consumed. Sometimes such food scales are stand-alone devices. Sometimes such food scales are incorporated into place settings (such as a specialized food-weighing plate, glass, or utensil). The vast majority of prior art in this category depends on some type of specific action by the person to record the type of food that is on the scale. Once the type of food is manually entered, converting it into estimates of specific nutrients or calories can then be done in a relatively straight-forward manner using a computerized database.

Prior art in this category has the same compliance problems that plague other manual food logging methods. Will a person really weigh each bit of food on which they snack throughout the day? Will they bring a food scale to social eating situations and use it there? Will a person consistently identify each type of food that they eat and enter this information into the scale device? These questions highlight some of the potential disadvantages of this category of art for monitoring food consumption.

Examples of prior art that appear to be best classified in this category include: U.S. Pat. No. 4,387,777 (Jun. 14, 1983 Ash) "Calorie Counting Method and Apparatus", U.S. Pat. No. 4,875,533 (Oct. 24, 1989 Mihara et al.) "Automatic Weight Detecting Device", U.S. Pat. No. 4,911,256 (Mar. 27, 1990 Attikiouzel) "Dietetic Measurement Apparatus", U.S. Pat. No. 5,033,561 (Jul. 23, 1991 Hettinger) "Diet Control Device", U.S. Pat. No. 5,233,520 (Aug. 3, 1993 Kretsch et al.) "Method and System for Measurement of Intake of Foods, Nutrients and Other Food Components in the Diet", U.S. Pat. No. 5,388,043 (Feb. 7, 1995 Hettinger) "Diet and Behavioral Control Device", U.S. Pat. No. 5,817,006 (Oct. 6, 1998 Bergh et al.) "Method and Apparatus for Measurement of Eating Speed", and U.S. Pat. No. 6,425,862 (Jul. 30, 2002 Brown) "Interactive Furniture for Dieters"; and U.S. patent applications 20020124017 (Sep. 5, 2002 Mault) "Personal Digital Assistant with Food Scale Accessory", 20060263750 (Nov. 23, 2006 Gordon) "Personal Nutrition Control Devices", 20070028453 (Feb. 8, 2007 Crow) "Portion Control Serving Utensils", 20070050058 (Mar. 1, 2007 Zuziak et al.) "Placemat for Calculating and Monitoring Calorie Intake", 20070173703 (Jul. 26, 2007 Lee et al.) "Method, Apparatus, and Medium for Managing Weight by Using Calorie Consumption Information", and 20120055718 (Mar. 8, 2012 Chen) "Electronic Scale for Recording Health Administration Data".

14. Portion Size Control

Prior art in this category includes specific-size food containers, place settings, and/or serving utensils that standardize the portion sizes and/or bite sizes of food that a person consumes. Such prior art is heavily dependent on specific human actions (apart from the actual act of eating) to be successful. Food must be consistently stored, apportioned, served, and eaten using the specific containers, place settings, and/or serving utensils. Hand-held snacks consumed from a bag, for example, are not easily monitored by this approach. Also, a person can easily prepare food without using the specific containers. Further, such art by itself is not useful for food identification. Food identification requires further specific human action. For these reasons, this approach has significant limitations for consistent measurement and modification of food intake.

Examples of prior art that appear to be best classified in this category include: U.S. Pat. No. 4,075,769 (Feb. 28, 1978 Young) "Method and Article for Weight Reduction" and U.S. Pat. No. 7,044,739 (May 16, 2006 Matson) "System for Controlled Nutrition Consumption"; and U.S. patent applications 20050014111 (Jan. 20, 2005 Matson) "System for Controlled Nutrition Consumption", 20100125181 (May 20, 2010 Hyde et al.) "Food Content Detector", 20120031805 (Feb. 9, 2012 Stolarczyk) "Daily Meal Planning System", 20120077154 (Mar. 29, 2012 Highet et al.) "Incrementally-Sized Standard-Sized Eating-Ware System for Weight Management", and 20120144912 (Jun. 14, 2012 Kates et al.) "Portion Control System for Weight Loss and Maintenance".

15. Mouth Size or Function Modification

This category of prior art includes devices and methods that limit mouth capacity or function so that a person eats less. In an example, a bulky device can be attached within a person's oral cavity in order to reduce the size of the cavity so that a person eats less food with each mouthful. This assumes that the person will not simply eat more mouthfuls to compensate. In another example, a device can be attached within the person's mouth to create resistance to chewing motion so that eating takes more work. The intent is that the person will eat less if eating requires more effort. In an example, a device can block consumption of solid food. This assumes that blocking solid food is an effective way to modify a person's diet to manage their weight. In an example, a device can physically cover or shield a person's tongue and taste buds so that they eat less. This assumes that such a device will be tolerated and will not be removed.

It is not clear from the prior art how such devices could be selectively used to allow consumption of healthy food, but discourage consumption of unhealthy food. Also, the prior art does not disclose how such devices would allow moderate consumption of certain foods but limit excess consumption of those foods. Also, if such a device is removable, then it requires consistent voluntary compliance by the person in order to be effective.

Examples of prior art that appear to be best classified in this category include: U.S. Pat. No. 3,818,906 (Jun. 25, 1974 Stubbs) "Apparatus for Controlling Eating and Smoking Habits", U.S. Pat. No. 4,471,771 (Sep. 18, 1984 Brown) "Oral Weight Control Device", U.S. Pat. No. 4,738,259 (Apr. 19, 1988 Brown et al.) "Dental Appliance for Weight Control", U.S. Pat. No. 5,924,422 (Jul. 20, 1999 Gustafson) "Oral Device to Aid Weight Control", U.S. Pat. No. 5,979,449 (Nov. 9, 1999 Steer) "Oral Appliance Device and Method for use Thereof for Appetite Suppression", U.S. Pat. No. 6,422,243 (Jul. 23, 2002 Daram) "Taste Bud Shield and Method of Using Same", and U.S. Pat. No. 8,230,865 (Jul. 31, 2012 Shalon) "Palatal Implant"; and U.S. patent applications 20030059737 (Mar. 27, 2003 Hall) "Obesity Treatment Aid", 20050287495 (Dec. 29, 2005 Longley) "Dental Appliance for Weight Management", and 20120109051 (May 3, 2012 Harrell) "Devices, Methods, and Kits for Taste Modification and Controlling Food Intake".

16. Chewing and Swallowing Monitoring

Prior art in this category includes devices that monitor the chewing and/or swallowing actions that are associated with food consumption. In various examples, such devices can monitor chewing and/or swallowing by a method selected from the group consisting of: monitoring and analyzing sounds from a person's body to differentiate chewing and/or swallowing sounds from other sounds such as speaking; monitoring electromagnetic energy from a person's mouth muscles or internal gastrointestinal organs; and monitoring movement of a person's mouth or internal gastrointestinal organs.

Prior art in this category can be more automatic than art in many of the prior categories with respect to detecting when a person consumes food. Some art in this category can even generally differentiate between consumption of solid food vs. liquid food based on differences in sonic energy or electromagnetic energy. However, art in this category is generally very limited with respect to more-specific identification of what type of food a person is consuming. Also, a person can confuse or circumvent such a device by putting generally-solid food in a blender or by freezing generally-liquid food. Art in this category still relies on specific human actions to record food type apart from the actual action of eating. Also, since there can be different amounts of food per swallow, determination of food quantity based on the number of swallows can be problematic. Accordingly, prior art in this category has a number of limitations for measuring and modifying the types and quantities of food consumed.

Examples of prior art that appear to be best classified in this category include: U.S. Pat. No. 4,355,645 (Oct. 26, 1982 Mitani et al.) "Device for Displaying Masticatory Muscle Activities", U.S. Pat. No. 5,067,488 (Nov. 26, 1991 Fukada et al.) "Mastication Detector and Measurement Apparatus and Method of Measuring Mastication", U.S. Pat. No. 5,263,491 (Nov. 23, 1993 Thornton) "Ambulatory Metabolic Monitor", U.S. Pat. No. 6,135,950 (Oct. 24, 2000 Adams) "E-fit Monitor", U.S. Pat. No. 7,330,753 (Feb. 12, 2008 Policker et al.) "Analysis of Eating Habits", U.S. Pat. No. 7,840,269 (Nov. 23, 2010 Policker et al.) "Analysis of Eating Habits", U.S. Pat. No. 7,840,269 (Nov. 23, 2010 Policker et al.) "Analysis of Eating Habits", and U.S. Pat. No. 7,914,468 (Mar. 29, 2011 Shalon et al.) "Systems and Methods for Monitoring and Modifying Behavior"; and U.S. patent applications 20040147816 (Jul. 29, 2004 Policker et al.) "Analysis of Eating Habits", 20050283096 (Dec. 22, 2005 Chau et al.) "Apparatus and Method for Detecting Swallowing Activity", 20060064037 (Mar. 23, 2006 Shalon et al.) "Systems and Methods for Monitoring and Modifying Behavior", 20060064037 (Mar. 23, 2006 Shalon et al.) "Systems and Methods for Monitoring and Modifying Behavior", 20060064037 (Mar. 23, 2006 Shalon et al.) "Systems and Methods for Monitoring and Modifying Behavior", 20070299320 (Dec. 27, 2007 Policker et al.) "Analysis of Eating Habits", 20070299320 (Dec. 27, 2007 Policker et al.) "Analysis of Eating Habits", 20100076345 (Mar. 25, 2010 Soffer et al.) "Method, Device and System for Automatic Detection of Eating and Drinking", 20110125063 (May 26, 2011 Shalon et al.) "Systems and Methods for Monitoring and Modifying Behavior", 20110276312 (Nov. 10, 2011 Shalon et al.) "Device for Monitoring and Modifying Eating Behavior", 20120101874 (Apr. 26, 2012 Ben-Haim et al.) "Charger With Data Transfer Capabilities", and 20120203081 (Aug. 9, 2012 Leboeuf et al.) "Physiological and Environmental Monitoring Apparatus and Systems". Another example of prior art that appears to be best classified in this category is WO 2002082968 (Policker) "Analysis of Eating Habits."

17. Hand and/or Arm Motion Monitoring and Modification (Wrist)

This is the first of two categories of prior art wherein the intent is to detect and estimate food consumption by monitoring and analyzing hand and/or arm motion. This first category includes devices that are worn on a person's wrist or arm to directly monitor hand or arm motion. The second category (that follows this one) includes food utensils that indirectly monitor hand or arm motion when the utensil is held by a person and is used to bring food up to the person's mouth.

We have separated these devices into two categories because, even though they both monitor hand and arm motion, they have some different advantages and disadvantages. Devices worn on a person's wrist or arm have the advantage that they can be worn relatively continuously to monitor food consumption on a relatively continuous basis. Wrist-worn devices do not require that a person carry a specific motion-sensing food utensil everywhere that they go. However, a device that is worn on a person's wrist or arm can be subject to more false alarms (compared to a food utensil) due to non-food-consumption motions such as covering one's mouth when coughing, bringing a cigarette to one's mouth, or other hand-to-face gestures.

Many examples of devices in this category monitor hand and/or arm motion with an accelerometer. To the extent that there is a distinctive pattern of hand and/or arm movement associated with bringing food up to one's mouth, such a device can detect when food consumption is occurring. Such a device can also measure how rapidly or often the person brings their hand up to their mouth. A common use of such information is to encourage a person to eat at a slower pace. The idea that a person will eat less if they eat at a slower pace is based on the lag between food consumption and the feeling of satiety from internal gastric organs. If a person eats slower, then they will tend to not overeat past the point of internal identification of satiety. Detection of food consumption and approximate measurement of food consumption quantity that is based on hand or arm motion can also be useful for purposes other than slowing the pace of eating.

However, there are significant limitations to devices and methods in this category. First, such devices and methods do not provide good information concerning the types of food consumed. In this respect, they generally still rely on manual food identification methods. Second, although progress has been made to differentiate hand and/or arm motions that indicate food consumption from other types of hand and/or arm motions (such as covering one's mouth or brushing one's teeth), there remains imprecision with respect to quantification of food consumed based on analysis of hand-to-mouth movements. Third, it is tough to make such devices and methods tamper-resistant. A person can use non-conventional hand movements to eat, use a non-monitored hand to eat, eat larger bite sizes with each hand movement, remove the device from their wrist, or just ignore feedback from the device when they eat.

Examples of prior art that appear to be best classified in this category include: U.S. Pat. No. 3,885,576 (May 27, 1975 Symmes) "Wrist Band Including a Mercury Switch to Induce an Electric Shock", U.S. Pat. No. 4,965,553 (Oct. 23, 1990 DelBiondo et al.) "Hand-Near-Mouth Warning Device", U.S. Pat. No. 5,424,719 (Jun. 13, 1995 Ravid) "Consumption Control", U.S. Pat. No. 5,563,850 (Oct. 8, 1996 Hanapole) "Food Intake Timer", U.S. Pat. No. 8,112,281 (Feb. 7, 2012 Yeung et al.) "Accelerometer-Based Control of Wearable Audio Recorders", and U.S. Pat. No. 8,310,368 (Nov. 13, 2012 Hoover et al.) "Weight Control Device"; and U.S. patent applications 20060197670 (Sep. 7, 2006 Breibart) "Method and Associated Device for Personal Weight Control", 20080137486 (Jun. 12, 2008 Czarenk et al.) "Diet Watch", and 20100194573 (Aug. 5, 2010 Hoover et al.) "Weight Control Device".

18. Hand and/or Arm Motion Monitoring and Modification (Utensil)

Prior art in this category includes hand-held food serving utensils (such as forks or spoons) that indirectly monitor hand and/or arm motion to detect and estimate food consumption. Compared to the wrist-worn motion-detection devices that were discussed in the previous category, motion-detecting utensils can be less subject to false alarms because they are only used when the person consumes food. There are some recent examples of sophisticated food-analyzing utensils with sensors other than motion-sensors. Since they are qualitatively different than utensils with only motion sensors, we have put these more-sophisticated food-analyzing utensils in a separate category that follows in this categorization scheme.

Many examples of utensils in this category monitor motion with an accelerometer. Since the utensil is only used for food consumption, analysis of complex motion and differentiation of food consumption actions vs. other hand gestures is less important with a utensil than it is with a wrist-mounted device. Accordingly, some of the utensils in this category are quite simple. In the extreme, although crude, a single-axis accelerometer can be used. Other simple methods of measuring hand-to-mouth movement by a utensil are based on a simple holder or button on which the utensil is placed between mouthfuls. Another simple method is an internal fluid "horizontal level" or "lava lamp" feature attached to the utensil that is used to regulate the timing of hand-to-mouth motions.

The idea is that a person will eat less if they eat slower because there can be a lag between food consumption and identification of satiety by internal organs. If the person eats slower, then they will tend to not overeat past the point of internal identification of satiety. Detection of food consumption and approximate measurement of food consumption quantity based on hand or arm motion can also be useful for purposes other than slowing the pace of eating.

However, utensils with just a motion sensor do not provide good information concerning the type of food consumed. Also, compliance can be a huge issue for this approach. In order to be successful, a person has to bring the special utensil with them constantly and use it consistently whenever they eat. What happens when they are eating out in a social setting or eating a snack with their hands? For these reasons, special eating utensils with just a motion sensor are limited in their ability to consistently monitor and modify a person's food consumption.

Examples of prior art that appear to be best classified in this category include: U.S. Pat. No. 4,207,673 (Jun. 17, 1980 DiGirolamo et al.) "Cuttlery", U.S. Pat. No. 4,914,819 (Apr. 10, 1990 Ash) "Eating Utensil for Indicating When Food May be Eaten Therewith and a Method for Using the Utensil", U.S. Pat. No. 4,975,682 (Dec. 4, 1990 Kerr et al.) "Meal Minder Device", U.S. Pat. No. 5,299,356 (Apr. 5, 1994 Maxwell)

"Diet Eating Utensil", U.S. Pat. No. 5,421,089 (Jun. 6, 1995 Dubus et al.) "Fork with Timer", and U.S. Pat. No. 8,299,930 (Oct. 30, 2012 Schmid-Schonbein et al.) "Devices, Systems and Methods to Control Caloric Intake"; and U.S. patent applications 20070098856 (May 3, 2007 LePine) "Mealtime Eating Regulation Device", 20080276461 (Nov. 13, 2008 Gold) "Eating Utensil Capable of Automatic Bite Counting", 20090253105 (Oct. 8, 2009 Lepine) "Device for Regulating Eating by Measuring Potential", 20100109876 (May 6, 2010 Schmid-Schonbein et al.) "Devices, Systems and Methods to Control Caloric Intake", 20100240962 (Sep. 23, 2010 Contant) "Eating Utensil to Monitor and Regulate Dietary Intake", and 20120115111 (May 10, 2012 Lepine) "Mealtime Eating Regulation Device".

19. Utensil with Sensor Other than Motion Sensor

Prior art in this category includes food utensils with sensors other than motion sensors that are used to measure food consumption. Such art in this category is relatively innovative and there are relatively few examples to date. Prior art in this category represents an important step toward automated measurement of food consumption. In various examples, a utensil in this category can measure the volume, mass, density, or general composition of a bite-size portion of food that is transported by the utensil to a person's mouth.

However, a significant limitation of art in this category is that it relies on a person's compliance. The person must use the utensil each time that they eat anything in order for the system to successfully monitor food consumption. If a person eats food without using the utensil (e.g. when dining in a social setting or when eating a snack by hand), then the system is unaware of this food consumption. This can be problematic and the prior art does not offer a solution to this problem.

Examples of prior art that appear to be best classified in this category include: U.S. Pat. No. 8,229,676 (Jul. 24, 2012 Hyde et al.) "Food Content Detector", U.S. Pat. No. 8,285,488 (Oct. 9, 2012 Hyde et al.) ibid., U.S. Pat. No. 8,290,712 (Oct. 16, 2012 Hyde et al.) ibid., U.S. Pat. No. 8,321,141 (Nov. 27, 2012 Hyde et al.) ibid., and U.S. Pat. No. 8,355,875 (Jan. 15, 2013 Hyde et al.) ibid.; and U.S. patent applications 20100125176 (May 20, 2010 Hyde et al.) ibid., 20100125177 (May 20, 2010 Hyde et al.) ibid., 20100125178 (May 20, 2010 Hyde et al.) ibid., 20100125179 (May 20, 2010 Hyde et al.) ibid., 20100125180 (May 20, 2010 Hyde et al.) ibid., 20100125181 (May 20, 2010 Hyde et al.) ibid., 20100125417 (May 20, 2010 Hyde et al.) ibid., 20100125418 (May 20, 2010 Hyde et al.) ibid., 20100125419 (May 20, 2010 Hyde et al.) ibid., 20100125420 (May 20, 2010 Hyde et al.) ibid., and 20110184247 (Jul. 28, 2011 Contant et al.) "Comprehensive Management of Human Health".

20. Other Modification of Eating Speed

This category is a catch-all for other prior art that seeks to modify eating speed using methods that are not covered by prior categories. Examples of prior art in this category include "bite traffic light" devices and sound-activating timers that signal when a person can take another bite of food. Such devices differ from earlier devices because they are not incorporated into a utensil or a wrist-worn band.

Compliance issues are a major issue with this approach. Will a person consistently use and obey a "bite traffic light" in order to time the speed at which they take bites of food? Will a person consistently tap an application on a touch screen to time the speed at which they take bites of food? Such art might be helpful for some people with strong self-discipline, but these people might have enough self-discipline to achieve the same effect by just watching a clock or just eating slowly without any automated guidance. Better methods for measuring and monitoring food consumption are needed for people without such strong self-discipline.

Examples of prior art that appear to be best classified in this category include U.S. patents: U.S. Pat. No. 5,908,301 (Jun. 1, 1999 Lutz) "Method and Device for Modifying Behavior", U.S. Pat. No. 6,473,368 (Oct. 29, 2002 Stanfield) "Consumption Controller", and U.S. Pat. No. 6,765,488 (Jul. 20, 2004 Stanfield) "Enhanced Consumption Controller"; and patent application 20120021388 (Jan. 26, 2012 Arbuckle et al.) "System and Method for Weight Management".

21. Photo Identification of Food (Bar Code or Other Packaging-Based Code)

Prior art in this category includes devices and methods for identifying food consumption based on photo identification of food using bar codes or other packaging-based codes. If consumed food has a bar code (or other packaging-based code) then it is relatively easy for a system to associate specific nutrients and/or total calories with that food.

However, there are several limitations to this approach. First, a person may eat food that is not identified by bar codes or other packaging-based codes. Food served in restaurants or in other people's homes is unlikely to be identified by such codes. Also, even in a grocery store, not all food is identified by such codes. Second, a person may not eat all of the food that is identified by such codes. Other people may eat some of the food in a given package. Also, some of the food in a given package may be thrown out. Also, depending on the longevity of the food, some food in a given package may be eaten soon after purchase and the rest may be eaten long afterwards. Accordingly, it can be problematic using such codes to make associations between food eaten by a specific person in a specific time period and the person's success in achieving weight management goals during that time period.

Examples of prior art that appear to be best classified in this category include: U.S. Pat. No. 5,819,735 (Oct. 13, 1998 Mansfield et al.) "Device and Method for Monitoring Dietary Intake of Calories And Nutrients" and U.S. Pat. No. 6,283,914 (Sep. 4, 2001 Mansfield et al.) "Device and Method for Monitoring Dietary Intake of Calories and Nutrients"; and U.S. patent applications 20030163354 (Aug. 28, 2003 Shamoun) "Device for Collecting and Analyzing Nutritional Data and Method Therefor", 20030208110 (Nov. 6, 2003 Mault et al.) "Physiological Monitoring using Wrist-Mounted Device", 20060189853 (Aug. 24, 2006 Brown) "Method and System for Improving Adherence with a Diet Program or Other Medical Regimen", 20060229504 (Oct. 12, 2006 Johnson) "Methods and Systems for Lifestyle Management", 20070059672 (Mar. 15, 2007 Shaw) "Nutrition Tracking Systems and Methods", and 20090176526 (Jul. 9, 2009 Altman) "Longitudinal Personal Health Management System Using Mobile Data Capture".

22. Photo Identification of Food (Manual Picture Taking and Identification)

Prior art in this category includes image-based devices and methods that require specific voluntary human action associated with each food consumption event (apart from the actual act of eating) in order: to take pictures of food during food consumption; and to identify the types and quantities of food consumed based on those pictures. In this category, neither picture taking nor food identification is automated. In an example, such art can include having a person aim a camera-equipped mobile electronic device toward food each time that the person eats and requiring that the person identify the type and quantity of food consumed based on the resulting pictures.

In an example, food identification by a person can occur in real-time (before, during, or immediately after a meal) using voice recognition or a menu-driven user interface. In another example, food identification by a person can occur later, long after the meal. In an example, food identification can be done by the person whose food consumption is being monitored and measured. In an example, food identification can be done by someone else.

Such image-based food logging systems are an improvement over recording food consumed with a pencil and paper. However, these devices and systems still require manual intervention to aim an imaging device toward a food source and to take at least one picture each time that the person eats something. Accordingly, they depend heavily on the person's compliance. These devices and methods can be time-consuming (having to aim the field of vision toward food), easy to circumvent (a person may simply not take pictures of some food consumed), and embarrassing to use social dining situations. This can lead to low long-term compliance.

Any approach that depends on voluntary human action each time that a person eats anything is difficult to make tamper-resistant. It is very easy for someone to "cheat" by simply not taking pictures of some consumed food items. Also, even if the person does consistently takes pictures of every meal or snack that they eat, then they may be tempted to postpone the manual task of food identification for hours or days after a meal has occurred. This can cause inaccuracy. How many chips were left in that bag in the picture? Is that a "before" or "after" picture of that gallon of ice cream? Delays in food identification can lead to imprecision in identification of the types and quantities of food consumed.

Examples of prior art that appear to be best classified in this category include U.S. patent applications: 20020047867 (Apr. 25, 2002 Mault et al.) "Image Based Diet Logging", 20020109600 (Aug. 15, 2002 Mault et al.) "Body Supported Activity and Condition Monitor", 20070030339 (Feb. 8, 2007 Findlay et al.) "Method, System and Software for Monitoring Compliance", 20090112800 (Apr. 30, 2009 Athsani) "System and Method for Visual Contextual Search", and 20090219159 (Sep. 3, 2009 Morgenstern) "Method and System for an Electronic Personal Trainer".

23. Photo Identification of Food (Manual Picture Taking and Automatic Identification)

Prior art in this category includes image-based devices and methods that require specific voluntary human actions associated with each food consumption event (apart from the actual act of eating) in order to take pictures of food during consumption. However, these devices and methods automatically identify the types and quantities of food consumed based on these pictures. In various examples, automatic identification of food types and quantities can be based on: color and texture analysis; image segmentation; image pattern recognition; volumetric analysis based on a fiduciary market or other object of known size; and/or three-dimensional modeling based on pictures from multiple perspectives. In an example, food identification can occur before or during a meal. In an example, a mobile phone application can transmit images to a remote location where automatic food identification occurs.

In some examples, food identification is an interactive process that combines automatic and manual methods of food identification. In this category, picture taking is not automated. In an example, such art can include having a person aim a camera-equipped mobile electronic device toward food to take pictures every time that the person eats food.

Such image-based consumption monitoring systems are useful, but still require specific actions by the person to aim an imaging device toward a food source and to take at least one picture of food each time that the person eats something. Accordingly, such art depends on the person's compliance. Such devices and methods can be time-consuming, easy to circumvent, and embarrassing in social dining situations. Any approach that depends on voluntary human action each time that a person eats anything is difficult to make tamper-resistant. It is very easy for someone to eat something without first taking a picture of it.

Examples of prior art that appear to be best classified in this category include: U.S. Pat. No. 6,513,532 (Feb. 4, 2003 Mault et al.) "Diet and Activity Monitoring Device", U.S. Pat. No. 8,345,930 (Jan. 1, 2013 Tamrakar et al.) "Method for Computing Food Volume in a Method for Analyzing Food", and U.S. Pat. No. 8,363,913 (Jan. 29, 2013 Boushey et al.) "Dietary Assessment System and Method"; and U.S. patent applications 20010049470 (Dec. 6, 2001 Mault et al.) "Diet and Activity Monitoring Device", 20020027164 (Mar. 7, 2002 Mault et al.) "Portable Computing Apparatus Particularly Useful in a Weight Management Program", 20030065257 (Apr. 3, 2003 Mault et al.) "Diet and Activity Monitoring Device", 20030076983 (Apr. 24, 2003 Cox) "Personal Food Analyzer", 20080267444 (Oct. 30, 2008 Simons-Nikolova) "Modifying a Person's Eating and Activity Habits", 20100111383 (May 6, 2010 Boushey et al.) "Dietary Assessment System and Method", 20100173269 (Jul. 8, 2010 Puri et al.) "Food Recognition Using Visual Analysis and Speech Recognition", 20100191155 (Jul. 29, 2010 Kim et al.) "Apparatus for Calculating Calories Balance by Classifying User's Activity", 20100332571 (Dec. 30, 2010 Healey et al.) "Device Augmented Food Identification", 20110182477 (Jul. 28, 2011 Tamrakar et al.) "Method for Computing Food Volume in a Method for Analyzing Food", 20110318717 (Dec. 29, 2011 Adamowicz) "Personalized Food Identification and Nutrition Guidance System", 20120170801 (Jul. 5, 2012 De Oliveira et al.) "System for Food Recognition Method Using Portable Devices Having Digital Cameras", 20120179665 (Jul. 12, 2012 Baarman et al.) "Health Monitoring System", 20120313776 (Dec. 13, 2012 Utter) "General Health and Wellness Management Method and Apparatus for a Wellness Application Using Data from a Data-Capable Band", 20120326873 (Dec. 27, 2012 Utter) "Activity Attainment Method and Apparatus for a Wellness Application Using Data from a Data-Capable Band", and 20130004923 (Jan. 3, 2013 Utter) "Nutrition Management Method and Apparatus for a Wellness Application Using Data from a Data-Capable Band".

24. Photo Identification of Food (Automatic Picture Taking and Identification)

Prior art in this category includes image-based devices and methods that automatically take and analyze pictures of food in order to identify the types and quantities of food consumed without the need for specific human action associated with each food consumption event (apart from the actual act of eating). In an example, automatic picture taking can occur using a camera that the person wears continually. In an example, a wearable camera can take pictures continually. In various examples, automatic identification of food types and quantities can be based on: color and texture analysis; image segmentation; image pattern recognition; volumetric analysis based on a fiduciary market or other object of known size; and/or three-dimensional modeling based on pictures from multiple perspectives. As an advantage over freestanding mobile imaging devices, wearable imaging devices offer a higher degree of automation.

Although art in this category is an innovative advance in the field, it still has at least three significant limitations that have not been fully addressed by the prior art. First, there is a trade-off between the measurement advantages of a continually-imaging wearable camera and the potential intrusion into a person's privacy. How can one achieve the measurement advantages of the wearable-imaging approach to food consumption monitoring with minimal intrusion into a person's privacy? Second, how does one address the possibility that a person can tamper with, or circumvent, such a device? Prior art in this category does not offer a tamper-resistant device.

Third, there are limitations to how accurately an image-based system can identify the composition of food. For example, many types of food, especially liquids, look similar. For example, if a beverage is not consumed in its original container, how can an image-based system know whether the beverage is high sugar vs. low sugar, or unhealthy vs. healthy? What is that sandwiched between two buns in a burger? Is it beef or turkey or a "veggie burger"? For these reasons, even though image-based prior art in this category is innovative and useful, there remains a need for better methods for automatically measuring the types and quantities of food consumption.

Examples of prior art that appear to be best classified in this category include U.S. Pat. No. 6,508,762 (Jan. 21, 2003 Karnieli) "Method for Monitoring Food Intake" and patent applications 20020022774 (Feb. 21, 2002 Karnieli) "Method for Monitoring Food Intake", and 20090012433 (Jan. 8, 2009 Fernstrom et al.) "Method, Apparatus and System for Food Intake and Physical Activity Assessment".

25. Gastric Band

With this category, we now move from devices and methods that are primarily used externally to the human body to devices and methods that are primarily implanted within the human body. Prior art in this particular category includes implantable devices that externally constrain the cross-sectional size of a member of a person's gastrointestinal tract (such as their stomach) to constrain the volume or amount of food that a person consumes. In an example, art in this category includes gastric bands that externally encircle and constrain expansion of the upper portion of a person's stomach in order to limit the volume or amount of food that passes into the person's stomach. Many of the devices in this category are adjustable in size, allowing post-operative adjustment of the external circumference of the portion of the gastrointestinal organ which the device encircles. We have separated out such devices which include sensors (and can self-adjust) in a category following this one.

Although devices in this category are innovative and have benefited many people, such devices still have limitations. First, such devices in the prior art are relatively food blind. They blindly reduce intake of all types of food. The prior art does not specify how they could be used to selectively reduce intake of unhealthy food while allowing normal consumption of healthy food. Second, such devices can irritate or harm the tissue of the gastrointestinal organ which they encircle. Third, although such devices can limit the size and flow of food entering a person's stomach, such devices do not limit the overall quantity of food that enters a person's stomach over time. For example, if a person wishes to melt an entire gallon of ice cream and then ingest it, a gastric band will not prevent this. There remains a need for better approaches for selectively modifying a person's food consumption.

Examples of prior art that appear to be best classified in this category include: U.S. Pat. No. 6,547,801 (Apr. 15, 2003 Dargent et al.) "Gastric Constriction Device", U.S. Pat. No. 6,551,235 (Apr. 22, 2003 Forsell) "Implantable Pump", U.S. Pat. No. 6,966,875 (Nov. 22, 2005 Longobardi) "Adjustable Gastric Implant", U.S. Pat. No. 7,775,967 (Aug. 17, 2010 Gertner) "Closed Loop Gastric Restriction Devices and Methods", U.S. Pat. No. 7,798,954 (Sep. 21, 2010 Birk et al.) "Hydraulic Gastric Band with Collapsible Reservoir", U.S. Pat. No. 7,909,754 (Mar. 22, 2011 Hassler et al.) "Non-Invasive Measurement of Fluid Pressure in an Adjustable Gastric Band", U.S. Pat. No. 7,972,346 (Jul. 5, 2011 Bachmann et al.) "Telemetrically Controlled Band for Regulating Functioning of a Body Organ or Duct, and Methods of Making, Implantation And Use", U.S. Pat. No. 8,034,065 (Oct. 11, 2011 Coe et al.) "Controlling Pressure in Adjustable Restriction Devices", U.S. Pat. No. 8,043,206 (Oct. 25, 2011 Birk) "Self-Regulating Gastric Band with Pressure Data Processing", U.S. Pat. No. 8,100,870 (Jan. 24, 2012 Marcotte et al.) "Adjustable Height Gastric Restriction Devices and Methods", U.S. Pat. No. 8,137,261 (Mar. 20, 2012 Kierath et al.) "Device for the Treatment of Obesity", U.S. Pat. No. 8,292,800 (Oct. 23, 2012 Stone et al.) "Implantable Pump System", U.S. Pat. No. 8,317,677 (Nov. 27, 2012 Bertolote et al.) "Mechanical Gastric Band with Cushions", and U.S. Pat. No. 8,323,180 (Dec. 4, 2012 Birk et al.) "Hydraulic Gastric Band with Collapsible Reservoir"; and U.S. patent applications 20070156013 (Jul. 5, 2007 Birk) "Self-Regulating Gastric Band with Pressure Data Processing", 20070265645 (Nov. 15, 2007 Birk et al.) "Hydraulic Gastric Band Collapsible Reservoir", 20070265646 (Nov. 15, 2007 Mccoy et al.) "Dynamically Adjustable Gastric Implants", and 20080275484 (Nov. 6, 2008 Gertner) "Per Os Placement of Extragastric Devices".

Examples of prior art that appear to be best classified in this category also include U.S. patent applications: 20090157106 (Jun. 18, 2009 Marcotte et al.) "Adjustable Height Gastric Restriction Devices and Methods", 20090171375 (Jul. 2, 2009 Coe et al.) "Controlling Pressure in Adjustable Restriction Devices", 20090204131 (Aug. 13, 2009 Ortiz et al.) "Automatically Adjusting Band System with MEMS Pump", 20090204132 (Aug. 13, 2009 Ortiz et al.) "Automatically Adjusting Band System", 20090216255 (Aug. 27, 2009 Coe et al.) "Controlling Pressure in Adjustable Restriction Devices", 20090270904 (Oct. 29, 2009 Birk et al.) "Remotely Adjustable Gastric Banding System", 20090312785 (Dec. 17, 2009 Stone et al.) "Implantable Pump System", 20100228080 (Sep. 9, 2010 Tavori et al.) "Apparatus and Methods for Corrective Guidance of Eating Behavior after Weight Loss Surgery", 20100234682 (Sep. 16, 2010 Gertner) "Closed Loop Gastric Restriction Devices and Methods", 20100324358 (Dec. 23, 2010 Birk et al.) "Hydraulic Gastric Band with Collapsible Reservoir", 20110130626 (Jun. 2, 2011 Hassler et al.) "Non-Invasive Measurement of Fluid Pressure in an Adjustable Gastric Band", 20110184229 (Jul. 28, 2011 Raven et al.) "Laparoscopic Gastric Band with Active Agents", 20110201874 (Aug. 18, 2011 Birk et al.) "Remotely Adjustable Gastric Banding System", 20110207994 (Aug. 25, 2011 Burrell et al.) "Methods and Devices for Treating Morbid Obesity Using Hydrogel", 20110207995 (Aug. 25, 2011 Snow et al.) "Inductively Powered Remotely Adjustable Gastric Banding System", 20110208216 (Aug. 25, 2011 Fobi et al.) "Gastric Bypass Band and Surgical Method", and 20110270025 (Nov. 3, 2011 Fridez et al.) "Remotely Powered Remotely Adjustable Gastric Band System".

Examples of prior art that appear to be best classified in this category also include U.S. patent applications: 20110270030 (Nov. 3, 2011 Birk et al.) "Hydraulic Gastric Band with Collapsible Reservoir", 20110275887 (Nov. 10, 2011 Birk) "Self-Regulating Gastric Band with Pressure Data Processing", 20110306824 (Dec. 15, 2011 Perron et al.) "Remotely Adjustable Gastric Banding System", 20110313240 (Dec. 22, 2011 Phillips et al.) "Flow Restrictor and Method for Automatically Controlling Pressure for a Gastric Band", 20120046674 (Feb. 23, 2012 Augarten et al.) "Power Regulated Implant", 20120059216 (Mar. 8, 2012 Perron) "Remotely Adjustable Gastric Banding System", 20120067937 (Mar. 22, 2012 Menzel) "Internal Gastric Bander for Obesity", 20120083650 (Apr. 5, 2012 Raven) "Systems and Methods for Adjusting Gastric Band Pressure", 20120088962 (Apr. 12, 2012 Franklin et al.) "Self-Adjusting Gastric Band", 20120095288 (Apr. 19, 2012 Snow et al.) "Self-Adjusting Gastric Band", 20120130273 (May 24, 2012 Hassler et al.) "Non-Invasive Measurement of Fluid Pressure in an Adjustable Gastric Band", 20120190919 (Jul. 26, 2012 Phillips et al.) "Assembly and Method for Automatically Controlling Pressure for a Gastric Band", 20120197069 (Aug. 2, 2012 Lau et al.) "Assembly and Method for Automatically Controlling Pressure for a Gastric Band", 20120215061 (Aug. 23, 2012 Fridez et al.) "Hydraulic Gastric Band with Reversible Self-Opening Mechanism", 20120215062 (Aug. 23, 2012 Coe) "Remotely Adjustable Gastric Banding Device", 20120296157 (Nov. 22, 2012 Tozzi et al.) "Medical Device Comprising an Artificial Contractile Structure", and 20120302936 (Nov. 29, 2012 Belhe et al.) "External Anchoring Configurations for Modular Gastrointestinal Prostheses".

26. Gastric Band with Sensor

Prior art in this category is similar to that of the previous category except for the addition of a sensor and the possibility of self-adjusting operation. The vast majority of sensors in this category are pressure sensors. The addition of a pressure sensor to a gastric band enables remote or automatic adjustment of the size of the constraining band in response to pressure from the external circumference of the encircled gastrointestinal organ. This can help to reduce irritation or harm of organ tissue by a constraining band, can enable post-operative refinement of therapy, and can help to reduce undesirable regurgitation. However, the other limitations that were identified with respect to gastric bands in the above category are still generally applicable to gastric bands in this category.

Examples of prior art that appear to be best classified in this category include: U.S. Pat. No. 7,775,966 (Aug. 17, 2010 Dlugos et al.) "Non-Invasive Pressure Measurement in a Fluid Adjustable Restrictive Device", U.S. Pat. No. 7,879,068 (Feb. 1, 2011 Dlugos et al.) "Feedback Sensing for a Mechanical Restrictive Device", U.S. Pat. No. 8,251,888 (Aug. 28, 2012 Roslin et al.) "Artificial Gastric Valve", and U.S. Pat. No. 8,308,630 (Nov. 13, 2012 Birk et al.) "Hydraulic Gastric Band with Collapsible Reservoir"; and U.S. patent applications 20060173238 (Aug. 3, 2006 Starkebaum) "Dynamically Controlled Gastric Occlusion Device", 20060199997 (Sep. 7, 2006 Hassler et al.) "Monitoring of a Food Intake Restriction Device", 20060235448 (Oct. 19, 2006 Roslin et al.) "Artificial Gastric Valve", 20080172072 (Jul. 17, 2008 Pool et al.) "Internal Sensors for Use with Gastric Restriction Devices", 20090192534 (Jul. 30, 2009 Ortiz et al.) "Sensor Trigger", 20100152532 (Jun. 17, 2010 Marcotte) "Gastric Band System with Esophageal Sensor", 20100274274 (Oct. 28, 2010 Roslin et al.) "Artificial Gastric Valve", 20110034760 (Feb. 10, 2011 Brynelsen et al.) "Feedback Systems and Methods to Enhance Obstructive and Other Obesity Treatments", 20110245598 (Oct. 6, 2011 Gertner) "Closed Loop Gastric Restriction Devices and Methods", and 20120108921 (May 3, 2012 Raven et al.) "Gastric Banding System Adjustment Based on a Satiety Agent Concentration Level".

27. Gastrointestinal (GI) Bypass and Tissue Plication

A gastrointestinal bypass is the creation of a new route for food to travel through a person's gastrointestinal tract that is shorter and involves less absorption of nutrients than the normal route which food travels. In some examples, the creation of a gastrointestinal bypass is primarily a surgical procedure involving reconfiguration of gastrointestinal tissue that is not primarily dependent on an implantable medical device. In other examples, the creation of a gastrointestinal bypass depends on implantation of a specific medical device. In this category, we focus primarily the role of implantable medical devices in creating a gastric bypass.

Tissue plication involves the folding and/or compartmentalization of gastrointestinal tissue in order to change the flow and/or absorption of food in a person's gastrointestinal tract. In an example, stomach walls can be folded or compartmentalized by suturing or stapling tissue to reduce the surface area of the stomach to which food is exposed. Although one could argue that GI bypass and tissue plication should be in separate categories, we have grouped them together because they both involve altering natural tissue to change the pathway and absorption of food traveling through a person's gastrointestinal tract.

Gastrointestinal (GI) bypass and tissue plication can be very effective in reducing a person's food consumption and/or absorption of nutrients from food that is consumed. However, these approaches have some significant limitations. First, some of these operations are relatively invasive, including the health risks associated with the surgery and relatively-long recovery times. Second, most of these operations are non-reversible, even if they are unsuccessful or have adverse side effects. Third, prior art in this category blindly reduces absorption of nutrients from both healthy and unhealthy food. This can result in deficiencies of key nutrients. This is particularly problematic for procedures that are non-reversible.

Examples of prior art that appear to be best classified in this category include: U.S. Pat. No. 6,558,400 (May 6, 2003 Deem et al.) "Obesity Treatment Tools and Methods", U.S. Pat. No. 6,572,629 (Jun. 3, 2003 Kalloo et al.) "Gastric Reduction Endoscopy", U.S. Pat. No. 7,037,343 (May 2, 2006 Imran) "Stomach Prosthesis", U.S. Pat. No. 7,037,344 (May 2, 2006 Kagan et al.) "Apparatus and Methods for Treatment of Morbid Obesity", U.S. Pat. No. 7,141,071 (Nov. 28, 2006 Imran) "Implantable Digestive Tract Organ", U.S. Pat. No. 7,288,099 (Oct. 30, 2007 Deem et al.) "Obesity Treatment Tools and Methods", U.S. Pat. No. 7,288,101 (Oct. 30, 2007 Deem et al.) "Obesity Treatment Tools and Methods", U.S. Pat. No. 7,503,922 (Mar. 17, 2009 Deem et al.) "Obesity Treatment Tools and Methods", U.S. Pat. No. 7,510,559 (Mar. 31, 2009 Deem et al.) "Obesity Treatment Tools and Methods", U.S. Pat. No. 7,601,178 (Oct. 13, 2009 Imran) "Stomach Peristalsis Device and Method", U.S. Pat. No. 7,803,195 (Sep. 28, 2010 Levy et al.) "Obesity Treatment and Device", U.S. Pat. No. 7,862,574 (Jan. 4, 2011 Deem et al.) "Obesity Treatment Tools and Methods", U.S. Pat. No. 7,909,838 (Mar. 22, 2011 Deem et al.) "Obesity Treatment Tools and Methods", U.S. Pat. No. 7,909,839 (Mar. 22, 2011 Fields) "Gastric Bypass Band and Surgical Method", U.S. Pat. No. 7,931,694 (Apr. 26, 2011 Imran) "Stomach Peristalsis Device and Method", U.S. Pat. No. 7,938,769 (May 10, 2011 Gertner) "Compressive Device for Percutaneous Treatment of Obesity", U.S. Pat. No. 7,988,617 (Aug. 2, 2011 Gertner) "Extragastric Minimally Invasive Methods and Devices to Treat Obesity", and U.S. Pat. No. 8,034,118 (Oct. 11, 2011 Imran) "Implantable Digestive Tract Organ".

Examples of prior art that appear to be best classified in this category also include: U.S. Pat. No. 8,070,673 (Dec. 6, 2011 Gertner et al.) "Devices and Methods to Treat A Patient", U.S. Pat. No. 8,075,577 (Dec. 13, 2011 Deem et al.) "Obesity Treatment Tools and Methods", U.S. Pat. No. 8,080,022

(Dec. 20, 2011 Deem et al.) "Obesity Treatment Tools and Methods", U.S. Pat. No. 8,080,025 (Dec. 20, 2011 Deem et al.) "Obesity Treatment Tools and Methods", U.S. Pat. No. 8,123,765 (Feb. 28, 2012 Deem et al.) "Obesity Treatment Tools and Methods", U.S. Pat. No. 8,137,366 (Mar. 20, 2012 Deem et al.) "Obesity Treatment Tools and Methods", U.S. Pat. No. 8,137,367 (Mar. 20, 2012 Deem et al.) "Obesity Treatment Tools and Methods", U.S. Pat. No. 8,147,441 (Apr. 3, 2012 Gannoe et al.) "Method and Device for Use in Endoscopic Organ Procedures", U.S. Pat. No. 8,187,289 (May 29, 2012 Tacchino et al.) "Device and Method for the Therapy of Obesity", U.S. Pat. No. 8,197,498 (Jun. 12, 2012 Coleman et al.) "Gastric Bypass Devices and Procedures", U.S. Pat. No. 8,206,456 (Jun. 26, 2012 Stack et al.) "Restrictive and/or Obstructive Implant System for Inducing Weight Loss", U.S. Pat. No. 8,211,128 (Jul. 3, 2012 Facundus et al.) "Multifunction Gastric Bypass Apparatus and Method", U.S. Pat. No. 8,252,009 (Aug. 28, 2012 Weller et al.) "Devices and Methods for Placement of Partitions within a Hollow Body Organ", and U.S. Pat. No. 8,287,554 (Oct. 16, 2012 Cerier et al.) "Method and Devices for Tissue Reconfiguration".

Examples of prior art that appear to be best classified in this category also include U.S. patent applications: 20040122452 (Jun. 24, 2004 Deem et al.) "Obesity Treatment Tools and Methods", 20040122453 (Jun. 24, 2004 Deem et al.) "Obesity Treatment Tools and Methods", 20070093910 (Apr. 26, 2007 Imran) "Implantable Digestive Tract Organ", 20070250083 (Oct. 25, 2007 Deem et al.) "Obesity Treatment Tools and Methods", 20100004755 (Jan. 7, 2010 Imran) "Stomach Peristalsis Device and Method", 20100145378 (Jun. 10, 2010 Gertner) "Percutaneous Gastroplasty", 20100204723 (Aug. 12, 2010 Gertner) "Obesity Systems Placed Between the Abdominal Wall and Stomach", 20110009887 (Jan. 13, 2011 Harris et al.) "Methods for Reducing Gastric Volume", 20110009980 (Jan. 13, 2011 Levy et al.) "Obesity Treatment and Device", 20110098725 (Apr. 28, 2011 Cox et al.) "Devices and Methods for Endolumenal Weight Loss Treatments", 20110152899 (Jun. 23, 2011 Deem et al.) "Obesity Treatment Tools and Methods", 20110152899 (Jun. 23, 2011 Deem et al.) "Obesity Treatment Tools and Methods", 20110196504 (Aug. 11, 2011 Imran) "Stomach Peristalsis Device and Method", and 20110208209 (Aug. 25, 2011 Ewers et al.) "Devices and Methods for Laparoscopic Gastric Tissue Reconfiguration".

Examples of prior art that appear to be best classified in this category also include U.S. patent applications: 20110213385 (Sep. 1, 2011 Ewers et al.) "Delivery Systems and Methods for Gastric Reduction", 20110295055 (Dec. 1, 2011 Albrecht et al.) "Methods and Devices for the Rerouting of Chyme to Induct Intestinal Brake", 20120010459 (Jan. 12, 2012 Lau et al.) "Assembly and Method for Automatically Controlling Pressure for a Gastric Band", 20120016392 (Jan. 19, 2012 Silverman et al.) "Method for Treating Morbid Obesity", 20120022319 (Jan. 26, 2012 Muller) "Systems and Methods for Reducing Gastric Volume", 20120071900 (Mar. 22, 2012 Vahid et al.) "Methods for Reduction of Gastric Lumen", 20120101594 (Apr. 26, 2012 Fogel) "Endoscopic Implantable Device and Method for the Apposition of the Stomach Walls for Reducing the Stomach Internal Volume in a Weight Loss Surgery . . . ", 20120116536 (May 10, 2012 Imran) "Implantable Digestive Tract Organ", 20120160893 (Jun. 28, 2012 Harris et al.) "Methods and Devices for Reducing Gastric Volume", 20120165843 (Jun. 28, 2012 Gannoe et al.) "Method and Device for use in Endoscopic Organ Procedures", 20120165845 (Jun. 28, 2012 Harris et al.) "Methods and Devices for Reducing Gastric Volume", 20120209400 (Aug. 16, 2012 Schurr) "Medical Implant", 20120209400 (Aug. 16, 2012 Schurr) "Medical Implant", 20120265224 (Oct. 18, 2012 Coleman et al.) "Gastric Bypass Devices and Procedures", 20120296348 (Nov. 22, 2012 Saadat et al.) "Apparatus for Manipulating and Securing Tissue", and 20120296354 (Nov. 22, 2012 Hsu et al.) "Methods and Devices for Treating Obesity and GERD by Intussuscepting a Portion of Stomach Tissue".

28. Pumping Food Out of the Stomach Through an Intra-Abdominal Pathway

This novel and unusual category of prior art comprises an implantable intra-abdominal pathway and an accompanying pumping mechanism that allows a person to pump food out of their stomach. Using such a device, even if a person is unable to control what food they eat, the person can still avoid having the body absorb nutrients from the consumed food. This is a novel approach to the problem of excessive caloric intake, but there remain many unknowns with respect to its use. How will people view discharging partially-digested food through a permanent implantable intra-abdominal pathway as a method for losing weight? Will the connections between the intra-abdominal pathway, the person's actively-moving stomach, and the person's skin surface remain durable, secure, and sanitary?

Examples of prior art that appear to be best classified in this category include: U.S. Pat. No. 7,648,479 (Jan. 19, 2010 Solovay et al.) "Systems and Methods for Removing Ingested Material from a Stomach", U.S. Pat. No. 7,740,624 (Jun. 22, 2010 Klein et al.) "Method for Treating Obesity by Extracting Food", U.S. Pat. No. 7,815,629 (Oct. 19, 2010 Klein et al.) "Apparatus for Treating Obesity by Extracting Food", U.S. Pat. No. 8,002,758 (Aug. 23, 2011 Kamen et al.) "Systems and Methods for Removing Ingested Material from a Stomach", and U.S. Pat. No. 8,062,285 (Nov. 22, 2011 Langloss et al.) "Systems and Methods for Removing Ingested Material from a Stomach"; and U.S. Pat. No. 8,282,623 (Oct. 9, 2012 Klein et al.) "Method for Treating Obesity by Extracting Food", 20050277900 (Dec. 15, 2005 Klein et al.) "Apparatus for Treating Obesity by Extracting Food", 20080033345 (Feb. 7, 2008 Langloss et al.) "Systems and Methods for Removing Ingested Material from a Stomach", 20080033364 (Feb. 7, 2008 Kamen et al.) "Systems and Methods for Removing Ingested Material from a Stomach", 20080033365 (Feb. 7, 2008 Solovay et al.) "Systems and Methods for Removing Ingested Material from a Stomach", 20080039809 (Feb. 14, 2008 Kamen et al.) "Systems and Methods for Removing Ingested Material from a Stomach", 20080091146 (Apr. 17, 2008 Solovay et al.) "Shunt Apparatus for Treating Obesity by Extracting Food", 20100106130 (Apr. 29, 2010 Solovay et al.) "Method for Treating Obesity by Extracting Food", 20100106131 (Apr. 29, 2010 Klein et al.) "Method for Treating Obesity by Extracting Food", 20100241090 (Sep. 23, 2010 Klein et al.) "Apparatus for Treating Obesity by Extracting Food", 20110178480 (Jul. 21, 2011 Solovay et al.) "Shunt Apparatus for Treating Obesity by Extracting Food", and 20110190719 (Aug. 4, 2011 Kamen et al.) "Systems And Methods for Removing Ingested Material from a Stomach".

29. Gastric Tube

Prior art in this category includes insertion of a tube down into a person's gastrointestinal tract. Devices in this category, including gastric tubes, are generally used for feeding purposes rather than modification of food consumption or absorption. Nonetheless, we have included them here in this categorization scheme because tubes inserted into the gastrointestinal tract can be relevant to some approaches to modification of food consumption.

Examples of prior art that appear to be best classified in this category include: U.S. Pat. No. 7,794,425 (Sep. 14, 2010

Gobel) "Gastro-Esophageal Reflux Control System and Pump" and U.S. Pat. No. 7,967,780 (Jun. 28, 2011 Goebel) "Gastro-Esophageal Reflux Control System and Pump"; and U.S. patent applications 20080154191 (Jun. 26, 2008 Gobel) "Gastro-Esophageal Reflux Control System and Pump", 20090062725 (Mar. 5, 2009 Goebel) "Gastro-Esophageal Reflux Control System and Pump", 20100204669 (Aug. 12, 2010 Knight) "Enteral Feeding Safety Reservoir and System", 20100217194 (Aug. 26, 2010 Pang) "Device for Tube Feeding", 20100298812 (Nov. 25, 2010 Wolkenstorfer) "Catheter System", and 20110082442 (Apr. 7, 2011 Solovay et al.) "Externally Reinforced Percutaneous Gastrostomy Tube with Customizable Smooth Tube Length".

30. Enzyme Flow Modification

Prior art in this category includes diversion of enzymes that play a role in the digestion and absorption of food in the gastrointestinal tract. In various examples, the flow of enzymes into the gastrointestinal tract can be increased, decreased, or diverted. For example, enzymes can be diverted so that they are discharged into the gastrointestinal tract at a lower location, thereby reducing the digestion and absorption of food that passes through the gastrointestinal tract.

Examples of prior art that appear to be best classified in this category include: U.S. Pat. No. 7,833,279 (Nov. 16, 2010 Knudson et al.) "Pancreatic Exocrine Secretion Diversion Apparatus and Method"; and U.S. patent applications 20060106332 (May 18, 2006 Knudson et al.) "Pancreatic Exocrine Secretion Diversion Apparatus and Method", 20110021968 (Jan. 27, 2011 Knudson et al.) "Pancreatic Exocrine Secretion Diversion Apparatus and Method", 20120116285 (May 10, 2012 Duggirala) "Devices for Treating Obesity and Methods of Using Those Devices", and 20120172782 (Jul. 5, 2012 Thompson) "Methods for Biliary Diversion".

31. Gastrointestinal (GI) Volume or Pressure or Flow Modification

This relatively-broad category of prior art includes various devices that modify the interior volume of a gastrointestinal organ (such as the stomach), interior wall pressure of a gastrointestinal organ (such as the stomach), and/or food flow through a valve in a gastro-intestinal organ (such as the pyloric valve in the stomach). In various examples, art in this category can: occupy some of the interior volume of a gastrointestinal organ (such as an expandable gastric balloon in the stomach); apply pressure to the interior walls of a gastrointestinal organ (such as an expandable stomach stent); or mechanically modify the operation of a gastrointestinal valve (such as the operation of the pyloric valve within the stomach).

In an example, reducing the available space for food to occupy within the stomach can reduce the amount of food consumed and/or cause an earlier sensation of fullness. In an example, applying pressure to the interior walls of the stomach can cause an earlier sensation of fullness and reduce the amount of food consumed. In an example, reducing the outflow of food from the stomach by modifying the operation of the pyloric valve can lead to an earlier sensation of fullness and reduce food consumed.

However, there can be limitations to such devices. For example, the stomach can stretch even further when a balloon is implanted inside it or a stent is expanded within it, thwarting efforts to cause an earlier sensation of fullness or reduce food consumption. Also, even if a temporary balloon or stent is effective while implanted, that effect can be lost (or reversed) when the temporary balloon or stent is removed. In a worst case scenario, such a device can make the person worse off. After removal of a balloon or stent, a stretched stomach can accommodate even more food than normal, causing the person to eat more than ever in the long run.

Examples of prior art that appear to be best classified in this category include: U.S. Pat. No. 4,133,315 (Jan. 9, 1979 Berman et al.) "Method and Apparatus for Reducing Obesity", U.S. Pat. No. 4,416,267 (Nov. 22, 1983 Garren et al.) "Method and Apparatus for Treating Obesity", U.S. Pat. No. 4,592,339 (Jun. 3, 1986 Kuzmak et al.) "Gastric Banding Device", U.S. Pat. No. 4,694,827 (Sep. 22, 1987 Weiner et al.) "Inflatable Gastric Device for Treating Obesity and Method of Using the Same", U.S. Pat. No. 5,074,868 (Dec. 24, 1991 Kuzmak) "Reversible Stoma-Adjustable Gastric Band", U.S. Pat. No. 5,226,429 (Jul. 13, 1993 Kuzmak) "Laparoscopic Gastric Band and Method", U.S. Pat. No. 5,234,454 (Aug. 10, 1993 Bangs) "Percutaneous Intragastric Balloon Catheter and Method for Controlling Body Weight Therewith", U.S. Pat. No. 5,259,399 (Nov. 9, 1993 Brown) "Device and Method of Causing Weight Loss Using Removable Variable Volume Intragastric Bladder", U.S. Pat. No. 5,449,368 (Sep. 12, 1995 Kuzmak) "Laparoscopic Adjustable Gastric Banding Device and Method for Implantation and Removal Thereof", U.S. Pat. No. 5,601,604 (Feb. 11, 1997 Vincent) "Universal Gastric Band", U.S. Pat. No. 5,868,141 (Feb. 9, 1999 Ellias) "Endoscopic Stomach Insert for Treating Obesity and Method for Use", U.S. Pat. No. 5,993,473 (Nov. 30, 1999 Chan et al.) "Expandable Body Device for the Gastric Cavity and Method", U.S. Pat. No. 6,067,991 (May 30, 2000 Forsell) "Mechanical Food Intake Restriction Device", U.S. Pat. No. 6,454,785 (Sep. 24, 2002 De Hoyos Garza) "Percutaneous Intragastric Balloon Catheter for the Treatment Of Obesity", U.S. Pat. No. 6,579,301 (Jun. 17, 2003 Bales et al.) "Intragastric Balloon Device Adapted to be Repeatedly Varied in Volume Without External Assistance", U.S. Pat. No. 6,675,809 (Jan. 13, 2004 Stack et al.) "Satiation Devices and Methods", U.S. Pat. No. 6,733,512 (May 11, 2004 Mcghan) "Self-Deflating Intragastric Balloon", U.S. Pat. No. 6,981,980 (Jan. 3, 2006 Sampson et al.) "Self-Inflating Intragastric Volume-Occupying Device", U.S. Pat. No. 7,033,373 (Apr. 25, 2006 DeLaTorre et al.) "Method and Device for Use in Minimally Invasive Placement of Space-Occupying Intragastric Devices", U.S. Pat. No. 7,066,945 (Jun. 27, 2006 Hashiba et al.) "Intragastric Device for Treating Obesity", and U.S. Pat. No. 7,112,186 (Sep. 26, 2006 Shah) "Gastro-Occlusive Device".

Examples of prior art that appear to be best classified in this category also include: U.S. Pat. No. 7,354,454 (Apr. 8, 2008 Stack et al.) "Satiation Devices and Methods", U.S. Pat. No. 7,470,251 (Dec. 30, 2008 Shah) "Gastro-Occlusive Device", U.S. Pat. No. 7,682,306 (Mar. 23, 2010 Shah) "Therapeutic Intervention Systems Employing Implantable Balloon Devices", U.S. Pat. No. 7,699,863 (Apr. 20, 2010 Marco et al.) "Bioerodible Self-Deployable Intragastric Implants", U.S. Pat. No. 7,717,843 (May 18, 2010 Balbierz et al.) "Restrictive and/or Obstructive Implant for Inducing Weight Loss", U.S. Pat. No. 7,758,493 (Jul. 20, 2010 Gingras) "Gastric Constriction Device", U.S. Pat. No. 7,771,382 (Aug. 10, 2010 Levine et al.) "Resistive Anti-Obesity Devices", U.S. Pat. No. 7,785,291 (Aug. 31, 2010 Marco et al.) "Bioerodible Self-Deployable Intragastric Implants", U.S. Pat. No. 7,841,978 (Nov. 30, 2010 Gertner) "Methods and Devices for to Treatment of Obesity", U.S. Pat. No. 7,963,907 (Jun. 21, 2011 Gertner) "Closed Loop Gastric Restriction Devices and Methods", U.S. Pat. No. 8,001,974 (Aug. 23, 2011 Makower et al.) "Devices and Methods for Treatment of Obesity", U.S. Pat. No. 8,016,744 (Sep. 13, 2011 Dlugos et al.) "External Pressure-Based Gastric Band Adjustment System and Method", U.S. Pat. No. 8,016,745 (Sep. 13, 2011 Hassler et al.) "Monitoring of a Food Intake Restriction Device", U.S. Pat. No. 8,029,455 (Oct. 4, 2011 Stack et al.) "Satiation Pouches and Methods of Use", U.S. Pat. No. 8,048,169 (Nov. 1, 2011 Burnett et al.) "Pyloric Valve Obstructing Devices and Methods", U.S. Pat. No. 8,066,780 (Nov. 29, 2011 Chen et al.) "Methods for Gastric Volume Control", U.S. Pat. No. 8,083,756 (Dec. 27, 2011 Gannoe et al.) "Methods and Devices for Maintaining a Space Occupying Device in a Relatively Fixed Location Within a Stomach", U.S. Pat. No. 8,083,757 (Dec. 27, 2011 Gannoe et al.) "Methods and Devices for Maintaining a Space Occupying Device in a Relatively Fixed Location Within a Stomach", U.S. Pat. No. 8,142,469 (Mar. 27, 2012 Sosnowski et al.) "Gastric Space Filler Device, Delivery System, and Related Methods", U.S. Pat. No. 8,142,513 (Mar. 27, 2012 Shalon et al.) "Devices and Methods for Altering Eating Behavior", U.S. Pat. No. 8,187,297 (May 29, 2012 Makower et al.) "Devices and Methods for Treatment of Obesity", U.S. Pat. No. 8,192,455 (Jun. 5, 2012 Brazzini et al.) "Compressive Device for Percutaneous Treatment of Obesity", U.S. Pat. No. 8,202,291 (Jun. 19, 2012 Brister et al.) "Intragastric Device", U.S. Pat. No. 8,226,593 (Jul. 24, 2012 Graham et al.) "Pyloric Valve", U.S. Pat. No. 8,236,023 (Aug. 7, 2012 Birk et al.) "Apparatus and Method for Volume Adjustment of Intragastric Balloons", U.S. Pat. No. 8,241,202 (Aug. 14, 2012 Balbierz et al.) "Restrictive and/or Obstructive Implant for Inducing Weight Loss", U.S. Pat. No. 8,267,888 (Sep. 18, 2012 Marco et al.) "Bioerodible Self-Deployable Intragastric Implants", U.S. Pat. No. 8,282,666 (Oct. 9, 2012 Birk) "Pressure Sensing Intragastric Balloon", U.S. Pat. No. 8,292,911 (Oct. 23, 2012 Brister et al.) "Intragastric Device", U.S. Pat. No. 8,292,911 (Oct. 23, 2012 Brister et al.) "Intragastric Device", U.S. Pat. No. 8,295,932 (Oct. 23, 2012 Bitton et al.) "Ingestible Capsule for Appetite Regulation", and U.S. Pat. No. 8,337,566 (Dec. 25, 2012 Stack et al.) "Method and Apparatus for Modifying the Exit Orifice of a Satiation Pouch".

Examples of prior art that appear to be best classified in this category also include U.S. patent applications: 20010037127 (Nov. 1, 2001 De Hoyos Garza) "Percutaneous Intragastric Balloon Catheter for the Treatment of Obesity", 20060252983 (Nov. 9, 2006 Lembo et al.) "Dynamically Adjustable Gastric Implants and Methods of Treating Obesity Using Dynamically Adjustable Gastric Implants", 20060264699 (Nov. 23, 2006 Gertner) "Extragastric Minimally Invasive Methods and Devices to Treat Obesity", 20070149994 (Jun. 28, 2007 Sosnowski et al.) "Intragastric Space Filler and Methods of Manufacture", 20070207199 (Sep. 6, 2007 Sogin) "Appetite Suppression Device", 20070276293 (Nov. 29, 2007 Gertner) "Closed Loop Gastric Restriction Devices and Methods", 20070293885 (Dec. 20, 2007 Binmoeller) "Methods and Devices to Curb Appetite and/or to Reduce Food Intake", 20080051824 (Feb. 28, 2008 Gertner) "Methods and Devices for to Treatment of Obesity", 20080065168 (Mar. 13, 2008 Bitton et al.) "Ingestible Capsule for Appetite Regulation", 20080147002 (Jun. 19, 2008 Gertner) "Obesity Treatment Systems", 20080161717 (Jul. 3, 2008 Gertner) "Obesity Treatment Systems", 20080188766 (Aug. 7, 2008 Gertner) "Obesity Treatment Systems", 20080208240 (Aug. 28, 2008 Paz) "Implantable Device for Obesity Prevention", 20080319471 (Dec. 25, 2008 Sosnowski et al.) "Gastric Space Filler Device, Delivery System, and Related Methods", 20090131968 (May 21, 2009 Birk) "Pressure Sensing Intragastric Balloon", 20090192535 (Jul. 30, 2009 Kasic) "Swallowable Self-Expanding Gastric Space Occupying Device", 20090247992 (Oct. 1, 2009 Shalon et al.) "Devices and Methods for Altering Eating Behavior", 20090259246 (Oct. 15, 2009 Eskaros et al.) "Intragastric Volume-Occupying Device", 20090275973 (Nov. 5, 2009 Chen et al.) "Devices and Systems for Gastric Volume Control", 20090306462 (Dec. 10, 2009 Lechner) "System for Controlling a Controllable Stomach Band", 20100100117 (Apr. 22, 2010 Brister et al.) "Intragastric Device", 20100114125 (May 6, 2010 Albrecht et al.) "Method of Remotely Adjusting a Satiation and Satiety-Inducing Implanted Device", 20100114125 (May 6, 2010 Albrecht et al.) "Method of Remotely Adjusting a Satiation and Satiety-Inducing Implanted Device", 20100130998 (May 27, 2010 Alverdy) "Balloon System and Methods for Treating Obesity", 20100137897 (Jun. 3, 2010 Brister et al.) "Intragastric Device", 20100152764 (Jun. 17, 2010 Merkle) "Device for Treating Obesity", 20100286660 (Nov. 11, 2010 Gross) "Gastroretentive Duodenal Pill", and 20100298632 (Nov. 25, 2010 Levine et al.) "Resistive Anti-Obesity Devices".

Examples of prior art that appear to be best classified in this category also include U.S. patent applications: 20100312049 (Dec. 9, 2010 Forsell) "Apparatus for Treating Obesity", 20100312050 (Dec. 9, 2010 Forsell) "Method and Instrument for Treating Obesity", 20100312147 (Dec. 9, 2010 Gertner) "Obesity Treatment Systems", 20100324361 (Dec. 23, 2010 Forsell) "Apparatus for Treating Obesity", 20100331616 (Dec. 30, 2010 Forsell) "Method and Instrument for Treating Obesity", 20100331617 (Dec. 30, 2010 Forsell) "Device, System and Method for Treating Obesity", 20100332000 (Dec. 30, 2010 Forsell) "Device for Treating Obesity", 20110009895 (Jan. 13, 2011 Gertner) "Methods and Devices to Treat Obesity", 20110009896 (Jan. 13, 2011 Forsell) "Apparatus for Treating Obesity", 20110015665 (Jan. 20, 2011 Marco et al.) "Bioerodible Self-Deployable Intragastric Implants", 20110015666 (Jan. 20, 2011 Marco et al.) "Bioerodible Self-Deployable Intragastric Implants", 20110022072 (Jan. 27, 2011 Marco et al.) "Bioerodible Self-Deployable Intragastric Implants", 20110040318 (Feb. 17, 2011 Marco et al.) "Bioerodible Self-Deployable Intragastric Implants", 20110060308 (Mar. 10, 2011 Stokes et al.) "Methods and Implants for Inducing Satiety in the Treatment of Obesity", 20110060358 (Mar. 10, 2011 Stokes et al.) "Methods and Implants for Inducing Satiety in the Treatment of Obesity", 20110092998 (Apr. 21, 2011 Hirszowicz et al.) "Balloon Hydraulic and Gaseous Expansion System", 20110106129 (May 5, 2011 Gertner) "Methods and Devices to Treat Obesity", 20110172693 (Jul. 14, 2011 Forsell) "Apparatus and Method for Treating Obesity", 20110178544 (Jul. 21, 2011 Sosnowski et al.) "Gastric Space Filler Delivery System and Related Methods", 20110196411 (Aug. 11, 2011 Forsell) "Apparatus for Treating Obesity", 20110213448 (Sep. 1, 2011 Kim) "Apparatus and Methods for Minimally Invasive Obesity Treatment", 20110213469 (Sep. 1, 2011 Chin et al.) "Systems and Methods for Bariatric Therapy", 20110224714 (Sep. 15, 2011 Gertner) "Methods and Devices for the Surgical Creation of Satiety and Biofeedback Pathways", 20110269711 (Nov. 3, 2011 Adden et al.) "Methods and Compositions for Inducing Satiety", and 20110295056 (Dec. 1, 2011 Aldridge et al.) "Systems and Methods for Gastric Volume Regulation".

Examples of prior art that appear to be best classified in this category also include U.S. patent applications: 20110295057 (Dec. 1, 2011 Aldridge et al.) "Systems and Methods for Gastric Volume Regulation", 20110307075 (Dec. 15, 2011 Sharma) "Intragastric Device for Treating Obesity", 20110319924 (Dec. 29, 2011 Cole et al.) "Gastric Space Occupier Systems and Methods of Use", 20120004590 (Jan. 5, 2012 Stack et al.) "Satiation Pouches and Methods of Use", 20120022322 (Jan. 26, 2012 Pasricha) "Methods and Devices for Treating Obesity", 20120029550 (Feb. 2, 2012

Forsell) "Obesity Treatment", 20120041463 (Feb. 16, 2012 Forsell) "Obesity Treatment", 20120053613 (Mar. 1, 2012 Weitzner et al.) "Gastric Filler Devices for Obesity Therapy", 20120089168 (Apr. 12, 2012 Baker et al.) "Bariatric Device and Method", 20120089170 (Apr. 12, 2012 Dominguez) "Intragastric Balloon Geometries", 20120089172 (Apr. 12, 2012 Babkes et al.) "Re-Shaping Intragastric Implants", 20120095384 (Apr. 19, 2012 Babkes et al.) "Stomach-Spanning Gastric Implants", 20120095492 (Apr. 19, 2012 Babkes et al.) "Variable Size Intragastric Implant Devices", 20120095494 (Apr. 19, 2012 Dominguez et al.) "Intragastric Implants with Collapsible Frames", 20120095495 (Apr. 19, 2012 Babkes et al.) "Space-Filling Intragastric Implants with Fluid Flow", 20120095496 (Apr. 19, 2012 Dominguez et al.) "Reactive Intragastric Implant Devices", 20120095497 (Apr. 19, 2012 Babkes et al.) "Non-Inflatable Gastric Implants and Systems", 20120095499 (Apr. 19, 2012 Babkes et al.) "Upper Stomach Gastric Implants", 20120123465 (May 17, 2012 Nihalani) "Method and Apparatus for Treating Obesity and Controlling Weight Gain using Self-Expanding Intragastric Devices", 20120150316 (Jun. 14, 2012 Carvalho) "Esophageal Flow Controller", 20120165855 (Jun. 28, 2012 Shalon et al.) "Devices and Methods for Altering Eating Behavior", 20120165855 (Jun. 28, 2012 Shalon et al.) "Devices and Methods for Altering Eating Behavior", 20120191123 (Jul. 26, 2012 Brister et al.) "Intragastric Device", and 20120191124 (Jul. 26, 2012 Brister et al.) "Intragastric Device".

Examples of prior art that appear to be best classified in this category also include U.S. patent applications: 20120191125 (Jul. 26, 2012 Babkes et al.) "Intragastric Implants with Multiple Fluid Chambers", 20120191126 (Jul. 26, 2012 Pecor et al.) "Inflation and Deflation Mechanisms for Inflatable Medical Devices", 20120203061 (Aug. 9, 2012 Birk) "Bariatric Device and Method for Weight Loss", 20120215249 (Aug. 23, 2012 Brazzini et al.) "Compressive Device for Percutaneous Treatment of Obesity", 20120221037 (Aug. 30, 2012 Birk et al.) "Bariatric Device and Method for Weight Loss", 20120232576 (Sep. 13, 2012 Brister et al.) "Intragastric Device", 20120232577 (Sep. 13, 2012 Birk et al.) "Bariatric Device and Method for Weight Loss", 20120253378 (Oct. 4, 2012 Makower et al.) "Devices and Methods for Treatment of Obesity", 20120259427 (Oct. 11, 2012 Graham et al.) "Pyloric Valve", 20120265030 (Oct. 18, 2012 Li) "Devices Systems Kits and Methods for Treatment of Obesity", 20120265234 (Oct. 18, 2012 Brister et al.) "Intragastric Device", 20120283766 (Nov. 8, 2012 Makower et al.) "Devices and Methods for Treatment of Obesity", 20120289992 (Nov. 15, 2012 Quijano et al.) "Intragastric Balloon System and Therapeutic Processes and Products", and 20120316387 (Dec. 13, 2012 Volker) "Adjustable Gastric Wrap (AGW)".

32. Gastrointestinal (GI) Volume or Pressure or Flow Modification (with Drug)

Prior art in this category is similar to that in the previous category, except that it also includes delivery of a pharmaceutical agent. In various examples, this category can include drug-eluting gastric balloons, gastric balloons with an integral drug pump, and drug-eluting gastric stents. Although drug delivery can provide another therapeutic modality for these devices, the addition of drug delivery does not correct most of the potential limitations of devices that were discussed in the previous category. Accordingly, most of these limitations still apply to devices in this present category.

Examples of prior art that appear to be best classified in this category include: U.S. Pat. No. 6,627,206 (Sep. 30, 2003 Lloyd) "Method and Apparatus for Treating Obesity and for Delivering Time-Released Medicaments", U.S. Pat. No. 7,121,283 (Oct. 17, 2006 Stack et al.) "Satiation Devices and Methods", U.S. Pat. No. 7,152,607 (Dec. 26, 2006 Stack et al.) "Satiation Devices and Methods", U.S. Pat. No. 7,833, 280 (Nov. 16, 2010 Stack et al.) "Satiation Devices and Methods", U.S. Pat. No. 7,854,745 (Dec. 21, 2010 Brister et al.) "Intragastric Device", U.S. Pat. No. 8,070,768 (Dec. 6, 2011 Kim et al.) "Devices and Methods for Treatment of Obesity", U.S. Pat. No. 8,162,969 (Apr. 24, 2012 Brister et al.) "Intragastric Device", U.S. Pat. No. 8,177,853 (May 15, 2012 Stack et al.) "Satiation Devices and Methods", and U.S. Pat. No. 8,226,602 (Jul. 24, 2012 Quijana et al.) "Intragastric Balloon System and Therapeutic Processes and Products"; and U.S. patent applications 20030021822 (Jan. 30, 2003 Lloyd) "Method and Apparatus for Treating Obesity and for Delivering Time-Released Medicaments", 20040172142 (Sep. 2, 2004 Stack et al.) "Satiation Devices and Methods", 20070265598 (Nov. 15, 2007 Karasik) "Device and Method for Treating Weight Disorders", 20080243071 (Oct. 2, 2008 Quijano et al.) "Intragastric Balloon System and Therapeutic Processes and Products", 20100100116 (Apr. 22, 2010 Brister et al.) "Intragastric Volume-Occupying Device and Method for Fabricating Same", 20100114150 (May 6, 2010 Magal) "Duodenal Stimulation Devices and Methods for the Treatment of Conditions Relating to Eating Disorders", 20120016287 (Jan. 19, 2012 Stack et al.) "Satiation Devices and Methods", 20120022430 (Jan. 26, 2012 Stack et al.) "Satiation Devices and Methods", 20120245553 (Sep. 27, 2012 Raven et al.) "Intragastric Volume Occupying Device with Active Agents", and 20120271217 (Oct. 25, 2012 Stack et al.) "Satiation Devices and Methods".

33. Gastrointestinal (GI) Sleeve or Liner

Prior art in this category includes gastrointestinal sleeves, gastrointestinal liners, and other flexible tubular devices that are implanted within a person's gastrointestinal tract to reduce absorption of nutrients from food by reducing contact between food and the walls of the gastrointestinal tract. Gastric sleeves are common examples of devices in this category. As long as devices in this category can be securely and safely fastened to their proper location within the gastrointestinal tract so that they do not migrate or cause blockages, these devices have potential to be a useful addition to the available approaches to limiting absorption of nutrients from food. Most are less invasive than gastric bypass operations and can be removed if they do not work well.

However, gastrointestinal sleeves and liners in the prior art are food blind. They are not able to selectively reduce absorption of nutrients from unhealthy food and allow normal absorption of nutrients from healthy food. Also, they are implanted and thus do require an operation. In this respect, they are more invasive than purely-external approaches to monitoring and modifying food consumption.

Examples of prior art that appear to be best classified in this category include: U.S. Pat. No. 4,641,653 (Feb. 10, 1987 Rockey) "Medical Sleeve", U.S. Pat. No. 7,220,284 (May 22, 2007 Kagan et al.) "Gastrointestinal Sleeve Device and Methods for Treatment of Morbid Obesity", U.S. Pat. No. 7,695, 446 (Apr. 13, 2010 Levine et al.) "Methods of Treatment Using a Bariatric Sleeve", U.S. Pat. No. 7,753,870 (Jul. 13, 2010 Demarais et al.) "Systems and Methods for Treating Obesity", U.S. Pat. No. 7,794,447 (Sep. 14, 2010 Dann et al.) "Gastrointestinal Sleeve Device and Methods for Treatment of Morbid Obesity", U.S. Pat. No. 7,837,643 (Nov. 23, 2010 Levine et al.) "Methods and Devices for Placing a Gastrointestinal Sleeve", U.S. Pat. No. 7,837,669 (Nov. 23, 2010 Dann et al.) "Devices and Methods for Endolumenal Gastrointestinal Bypass", U.S. Pat. No. 7,846,138 (Dec. 7, 2010

Dann et al.) "Cuff and Sleeve System for Gastrointestinal Bypass", U.S. Pat. No. 7,935,073 (May 3, 2011 Levine et al.) "Methods of Treatment Using a Bariatric Sleeve", U.S. Pat. No. 7,981,162 (Jul. 19, 2011 Stack et al.) "Satiation Devices and Methods", U.S. Pat. No. 8,012,140 (Sep. 6, 2011 Kagan et al.) "Methods of Transmural Attachment in the Gastrointestinal System", U.S. Pat. No. 8,057,420 (Nov. 15, 2011 Meade et al.) "Gastrointestinal Implant with Drawstring", U.S. Pat. No. 8,070,743 (Dec. 6, 2011 Kagan et al.) "Devices and Methods for Attaching an Endolumenal Gastrointestinal Implant", U.S. Pat. No. 8,109,895 (Feb. 7, 2012 Williams et al.) "Intestinal Sleeves and Associated Deployment Systems and Methods", U.S. Pat. No. 8,137,301 (Mar. 20, 2012 Levine et al.) "Bariatric Sleeve", U.S. Pat. No. 8,162,871 (Apr. 24, 2012 Levine et al.) "Bariatric Sleeve", U.S. Pat. No. 8,182,459 (May 22, 2012 Dann et al.) "Devices and Methods for Endolumenal Gastrointestinal Bypass", U.S. Pat. No. 8,211,186 (Jul. 3, 2012 Belhe et al.) "Modular Gastrointestinal Prostheses", U.S. Pat. No. 8,216,158 (Jul. 10, 2012 Johnson) "Implantation of a Medical Device Within a Lumen", U.S. Pat. No. 8,282,598 (Oct. 9, 2012 Belhe et al.) "External Anchoring Configurations for Modular Gastrointestinal Prostheses", and U.S. Pat. No. 8,303,669 (Nov. 6, 2012 Meade et al.) "Methods and Apparatus for Anchoring within the Gastrointestinal Tract".

Examples of prior art that appear to be best classified in this category also include U.S. patent applications: 20090093767 (Apr. 9, 2009 Kelleher) "Devices and Methods for Endolumenal Therapy", 20090240340 (Sep. 24, 2009 Levine et al.) "Bariatric Sleeve", 20090248171 (Oct. 1, 2009 Levine et al.) "Bariatric Sleeve", 20100256775 (Oct. 7, 2010 Belhe et al.) "Modular Gastrointestinal Prostheses", 20100298631 (Nov. 25, 2010 Stack et al.) "Satiation Devices and Methods", 20110009690 (Jan. 13, 2011 Belhe et al.) "External Anchoring Configurations for Modular Gastrointestinal Prostheses", 20110087146 (Apr. 14, 2011 Ryan et al.) "Stomach Bypass for the Treatment of Obesity", 20110106273 (May 5, 2011 Belhe et al.) "Gastrointestinal Prostheses Having Partial Bypass Configurations", 20110245752 (Oct. 6, 2011 Levine et al.) "Methods of Treatment Using a Bariatric Sleeve", 20110270410 (Nov. 3, 2011 Stack et al.) "Satiation Devices and Methods", 20120004676 (Jan. 5, 2012 Vargas) "Intragastric Implant Devices", 20120041465 (Feb. 16, 2012 Shalon) "Devices and Methods for Treating Gastrointestinal and Metabolic Disorders", 20120053504 (Mar. 1, 2012 Kagan et al.) "Methods for Attachment of a Gastrointestinal Sleeve", 20120065571 (Mar. 15, 2012 Thompson et al.) "Expandable Pyloric Anchors and Methods for Securing Intestinal Bypass Sleeves", 20120116286 (May 10, 2012 Williams et al.) "Intestinal Sleeves and Associated Deployment Systems and Methods", 20120184893 (Jul. 19, 2012 Thompson et al.) "Anchors and Methods for Intestinal Bypass Sleeves", 20120215152 (Aug. 23, 2012 Levine et al.) "Bariatric Sleeve", 20120232459 (Sep. 13, 2012 Dann et al.) "Devices and Methods for Endolumenal Gastrointestinal Bypass", 20120253259 (Oct. 4, 2012 Belhe et al.) "Modular Gastrointestinal Prostheses", and 20120253260 (Oct. 4, 2012 Belhe et al.) "Gastrointestinal Prostheses".

34. Gastrointestinal (GI) Sleeve or Liner (with Drug)

Prior art in this category is similar to that in the previous category, except that it also includes delivery of a pharmaceutical agent. In various examples, this category includes drug-eluting gastric sleeves and liners. Although drug delivery can provide a secondary therapeutic modality for these devices, the addition of drug delivery does not help differentiate between healthy and unhealthy food. Accordingly, these devices remain food blind. They are not able to selectively reduce absorption of nutrients from unhealthy food and allow normal absorption of nutrients from healthy food.

Examples of prior art that appear to be best classified in this category include U.S. patent applications 20110040232 (Feb. 17, 2011 Magal) "Duodenal Liner Device" and 20120232460 (Sep. 13, 2012 Raven et al.) "Intraluminal Sleeve with Active Agents".

35. Electrical Stimulation (General)

Prior art in this category includes implantable devices that deliver electromagnetic energy to a portion of a person's gastrointestinal tract or to a nerve that innervates a portion of the person's gastrointestinal tract. In an example, electrical stimulation can be applied directly to a person's stomach in order to induce a sense of satiety and/or modify gastric motility. The intent of such gastric stimulation is to reduce a person's food consumption. In another example, electrical energy can be applied to block normal neural transmissions in a nerve that innervates a person's stomach in order to reduce gastric functioning and thereby reduce food consumption. This category of art has considerable potential (no pun intended) to modify food consumption. It is relatively non-invasive with respect to other internal procedures, is adjustable, and is reversible.

In order for devices in this category to be successful in modifying food consumption, the gastrointestinal organ or nerve to which electrical energy is applied must not accommodate (ie: become inured to) the application of electrical energy. If an organ or nerve does accommodate the application of electrical energy, then the organ or nerve stops responding to the applied energy in a therapeutic manner. For this reason, devices in this category generally apply electrical energy in a non-continuous manner.

The ability to differentiate between consumption of healthy vs. unhealthy food could enable such devices to selectively deliver electrical energy only when a person eats unhealthy food. This differentiating ability would allow use of higher power levels without the problem of accommodation and make such devices more effective for modifying food consumption. Such ability could also encourage the person to have a healthier diet and extend a device's battery life. However, prior art devices in this category do not appear to offer the ability to differentiate between consumption of healthy vs. unhealthy food.

Examples of prior art that appear to be best classified in this category include: U.S. Pat. No. 3,411,507 (Nov. 19, 1968 Wingrove) "Method of Gastrointestinal Stimulation with Electrical Pulses", U.S. Pat. No. 5,188,104 (Feb. 23, 1993 Wernicke et al.) "Treatment of Eating Disorders by Nerve Stimulation", U.S. Pat. No. 5,423,872 (Jun. 13, 1995 Cigaina) "Process and Device for Treating Obesity and Syndromes Related to Motor Disorders of the Stomach of a Patient", U.S. Pat. No. 5,690,691 (Nov. 25, 1997 Chen et al.) "Gastro-Intestinal Pacemaker Having Phased Multi-Point Stimulation", U.S. Pat. No. 5,716,385 (Feb. 10, 1998 Mittal et al.) "Crural Diaphragm Pacemaker and Method for Treating Esophageal Reflux Disease (Mittal)", U.S. Pat. No. 5,891,185 (Apr. 6, 1999 Freed et al.) "Method and Apparatus for Treating Oropharyngeal Disorders with Electrical Stimulation", U.S. Pat. No. 6,091,992 (Jul. 18, 2000 Bourgeois et al.) "Method and Apparatus for Electrical Stimulation of the Gastrointestinal Tract", U.S. Pat. No. 6,243,607 (Jun. 5, 2001 Mintchev et al.) "Gastro-Intestinal Electrical Pacemaker", U.S. Pat. No. 6,564,101 (May 13, 2003 Zikria) "Electrical System for Weight Loss and Laparoscopic Implanation Thereof", U.S. Pat. No. 6,587,719 (Jul. 1, 2003 Barrett et al.) "Treatment of Obesity by Bilateral Vagus Nerve Stimulation", U.S. Pat. No. 6,609,025 (Aug. 19, 2003 Barrett et al.)

"Treatment of Obesity by Bilateral Sub-Diaphragmatic Nerve Stimulation", U.S. Pat. No. 6,684,104 (Jan. 27, 2004 Gordon et al.) "Gastric Stimulator Apparatus and Method for Installing", U.S. Pat. No. 6,760,626 (Jul. 6, 2004 Boveja) "Apparatus and Method for Treatment of Neurological and Neuropsychiatric Disorders Using Programmerless Implantable Pulse Generator System", U.S. Pat. No. 6,879,859 (Apr. 12, 2005 Boveja) "External Pulse Generator for Adjunct (Add-On) Treatment of Obesity Eating Disorders Neurological Neuropsychiatric and Urological Disorders", U.S. Pat. No. 7,072,720 (Jul. 4, 2006 Puskas) "Devices and Methods for Vagus Nerve Stimulation", U.S. Pat. No. 7,167,750 (Jan. 23, 2007 Knudson et al.) "Obesity Treatment with Electrically Induced Vagal Down Regulation", U.S. Pat. No. 7,177, 693 (Feb. 13, 2007 Starkebaum) "Gastric Stimulation for Altered Perception to Treat Obesity", and U.S. Pat. No. 7,236, 822 (Jun. 26, 2007 Dobak) "Wireless Electric Modulation of Sympathetic Nervous System".

Examples of prior art that appear to be best classified in this category also include: U.S. Pat. No. 7,239,912 (Jul. 3, 2007 Dobak) "Electric Modulation of Sympathetic Nervous System", U.S. Pat. No. 7,299,091 (Nov. 20, 2007 Barrett et al.) "Treatment of Obesity by Bilateral Vagus Nerve Stimulation", U.S. Pat. No. 7,529,582 (May 5, 2009 Dilorenzo) "Method and Apparatus for Neuromodulation and Physiologic Modulation for the Treatment of Metabolic and Neuropsychiatric Disease", U.S. Pat. No. 7,551,964 (Jun. 23, 2009 Dobak) "Splanchnic Nerve Stimulation for Treatment of Obesity", U.S. Pat. No. 7,580,751 (Aug. 25, 2009 Starkebaum) "Intra-Luminal Device for Gastrointestinal Stimulation", U.S. Pat. No. 7,599,736 (Oct. 6, 2009 Dilorenzo) "Method and Apparatus for Neuromodulation and Physiologic Modulation for the Treatment of Metabolic and Neuropsychiatric Disease", U.S. Pat. No. 7,657,310 (Feb. 2, 2010 Buras) "Treatment of Reproductive Endocrine Disorders by Vagus Nerve Stimulation", U.S. Pat. No. 7,664,551 (Feb. 16, 2010 Cigaina) "Treatment of the Autonomic Nervous System", U.S. Pat. No. 7,689,276 (Mar. 30, 2010 Dobak) "Dynamic Nerve Stimulation for Treatment of Disorders", U.S. Pat. No. 7,689,277 (Mar. 30, 2010 Dobak) "Neural Stimulation for Treatment of Metabolic Syndrome and Type 2 Diabetes", U.S. Pat. No. 7,702,386 (Apr. 20, 2010 Dobak et al.) "Nerve Stimulation for Treatment of Obesity Metabolic Syndrome and Type 2 Diabetes", U.S. Pat. No. 7,729,771 (Jun. 1, 2010 Knudson et al.) "Nerve Stimulation and Blocking for Treatment of Gastrointestinal Disorders", U.S. Pat. No. 7,756,582 (Jul. 13, 2010 Imran et al.) "Gastric Stimulation Anchor and Method", U.S. Pat. No. 7,840,278 (Nov. 23, 2010 Puskas) "Devices and Methods for Vagus Nerve Stimulation", U.S. Pat. No. 7,945,323 (May 17, 2011 Jaax et al.) "Treatment of Obesity and/or Type II Diabetes by Stimulation of the Pituitary Gland", U.S. Pat. No. 7,979,127 (Jul. 12, 2011 Imran) "Digestive Organ Retention Device", U.S. Pat. No. 7,986,995 (Jul. 26, 2011 Knudson et al.) "Bulimia Treatment", U.S. Pat. No. 8,082,039 (Dec. 20, 2011 Kim et al.) "Stimulation Systems", U.S. Pat. No. 8,145,299 (Mar. 27, 2012 Dobak) "Neural Stimulation for Treatment of Metabolic Syndrome and Type 2 Diabetes", U.S. Pat. No. 8,150,508 (Apr. 3, 2012 Craig) "Vagus Nerve Stimulation Method", U.S. Pat. No. 8,280,505 (Oct. 2, 2012 Craig) "Vagus Nerve Stimulation Method", U.S. Pat. No. 8,301,256 (Oct. 30, 2012 Policker et al.) "GI Lead Implantation", and U.S. Pat. No. 8,340,772 (Dec. 25, 2012 Vase et al.) "Brown Adipose Tissue Utilization Through Neuromodulation".

Examples of prior art that appear to be best classified in this category also include U.S. patent applications: 20040167583 (Aug. 26, 2004 Knudson et al.) "Electrode Band Apparatus and Method", 20070027498 (Feb. 1, 2007 Maschino et al.) "Selective Nerve Stimulation for the Treatment of Eating Disorders", 20070135846 (Jun. 14, 2007 Knudson et al.) "Vagal Obesity Treatment", 20070150021 (Jun. 28, 2007 Chen et al.) "Gastrointestinal Electrical Stimulation", 20070203521 (Aug. 30, 2007 Dobak et al.) "Nerve Stimulation for Treatment of Obesity Metabolic Syndrome and Type 2 Diabetes", 20080046013 (Feb. 21, 2008 Lozano) "Method for Treating Eating Disorders", 20080183238 (Jul. 31, 2008 Chen) "Process for Electrostimulation Treatment of Morbid Obesity", 20080195171 (Aug. 14, 2008 Sharma) "Method and Apparatus for Electrical Stimulation of the Pancreatico-Biliary System", 20090018606 (Jan. 15, 2009 Sparks et al.) "Methods and Devices for Stimulation of an Organ with the Use of a Transectionally Placed Guide Wire", 20090259274 (Oct. 15, 2009 Simon et al.) "Methods and Apparatus for Electrical Treatment Using Balloon and Electrode", 20090259279 (Oct. 15, 2009 Dobak) "Splanchnic Nerve Stimulation for Treatment of Obesity", 20100087706 (Apr. 8, 2010 Syed et al.) "Lead Access", 20100094375 (Apr. 15, 2010 Donders et al.) "Neural Electrode Treatment", 20100168815 (Jul. 1, 2010 Knudson et al.) "Nerve Stimulation and Blocking for Treatment of Gastrointestinal Disorders", 20100183700 (Jul. 22, 2010 Stojanovic-Susulic et al.) "Implantable Pump for Protein Delivery for Obesity Control by Drug Infusion into the Brain", 20100234917 (Sep. 16, 2010 Imran) "Digestive Organ Retention Device", and 20100286745 (Nov. 11, 2010 Imran) "Radially Expandable Gastrointestinal Stimulation Device".

Examples of prior art that appear to be best classified in this category also include U.S. patent applications: 20110034967 (Feb. 10, 2011 Chen et al.) "Gastrointestinal Electrical Stimulation", 20110034968 (Feb. 10, 2011 Knudson et al.) "Controlled Vagal Blockage Therapy", 20110166582 (Jul. 7, 2011 Syed et al.) "Endoscopic Device Delivery System", 20110230938 (Sep. 22, 2011 Simon et al.) "Device and Methods for Non-Invasive Electrical Stimulation and Their Use for Vagal Nerve Stimulation", 20110238035 (Sep. 29, 2011 Jaax et al.) "Treatment of Obesity and/or Type II Diabetes by Stimulation of the Pituitary Gland", 20110270344 (Nov. 3, 2011 Knudson et al.) "Bulimia Treatment", 20110307023 (Dec. 15, 2011 Tweden et al.) "Neural Modulation Devices and Methods", 20110319969 (Dec. 29, 2011 Dobak) "Electric Modulation of Sympathetic Nervous System", 20120041509 (Feb. 16, 2012 Knudson et al.) "Controlled Vagal Blockage Therapy", 20120053653 (Mar. 1, 2012 Hiernaux et al.) "Gastrointestinal Device", 20120053660 (Mar. 1, 2012 Dobak) "Splanchnic Nerve Stimulation for Treatment of Obesity", 20120071947 (Mar. 22, 2012 Gupta et al.) "Method and Apparatus for Event-Triggered Reinforcement of a Favorable Brain State", 20120143279 (Jun. 7, 2012 Ekchian et al.) "Methods and Kits for Treating Appetite Suppressing Disorders and Disorders with an Increased Metabolic Rate", 20120209354 (Aug. 16, 2012 Raykhman) "System and Methods for Producing and Delivering Electrical Impulses", and 20120310295 (Dec. 6, 2012 Libbus et al.) "Systems and Methods for Avoiding Neural Stimulation Habituation".

36. Electrical Stimulation (with Glucose Sensor)

Devices in this category are similar to devices in the previous category of general electrical stimulation except that they also include a glucose sensor. They deliver electromagnetic energy to person's gastrointestinal tract or to a nerve that innervates their gastrointestinal tract. In an example, a person's blood glucose level can be monitored and gastrointestinal electrical stimulation can be triggered when the person's glucose level indicates that such stimulation is most needed. Selective electrical stimulation can help to target therapeutic benefit.

Examples of prior art that appear to be best classified in this category include: U.S. Pat. No. 6,093,167 (Jul. 25, 2000 Houben et al.) "System for Pancreatic Stimulation and Glucose Measurement", U.S. Pat. No. 6,185,452 (Feb. 6, 2001 Schulman et al.) "Battery-Powered Patient Implantable Device", U.S. Pat. No. 6,571,127 (May 27, 2003 Ben-Haim et al.) "Method of Increasing the Motility of a GI Tract", U.S. Pat. No. 6,600,953 (Jul. 29, 2003 Flesler et al.) "Acute and Chronic Electrical Signal Therapy for Obesity", U.S. Pat. No. 6,832,114 (Dec. 14, 2004 Whitehurst et al.) "Systems and Methods for Modulation of Pancreatic Endocrine Secretion and Treatment of Diabetes", U.S. Pat. No. 6,922,590 (Jul. 26, 2005 Whitehurst) "Systems and Methods for Treatment of Diabetes by Electrical Brain Stimulation and/or Drug Infusion", U.S. Pat. No. 6,993,391 (Jan. 31, 2006 Flesler et al.) "Acute and Chronic Electrical Signal Therapy for Obesity", U.S. Pat. No. 7,020,531 (Mar. 28, 2006 Colliou et al.) "Gastric Device and Suction Assisted Method for Implanting a Device on a Stomach Wall", U.S. Pat. No. 7,440,806 (Oct. 21, 2008 Whitehurst et al.) "Systems and Methods for Treatment of Diabetes by Electrical Brain Stimulation and/or Drug Infusion", U.S. Pat. No. 7,477,944 (Jan. 13, 2009 Whitehurst et al.) "Systems and Methods for Modulation of Pancreatic Endocrine Secretion and Treatment of Diabetes", U.S. Pat. No. 7,502,649 (Mar. 10, 2009 Ben-Haim et al.) "Gastrointestinal Methods and Apparatus for Use in Treating Disorders", U.S. Pat. No. 7,512,442 (Mar. 31, 2009 Flesler et al.) "Acute and Chronic Electrical Signal Therapy for Obesity", U.S. Pat. No. 7,558,629 (Jul. 7, 2009 Keimel et al.) "Energy Balance Therapy for Obesity Management", U.S. Pat. No. 7,937,145 (May 3, 2011 Dobak) "Dynamic Nerve Stimulation Employing Frequency Modulation", U.S. Pat. No. 8,019,421 (Sep. 13, 2011 Darvish et al.) "Blood Glucose Level Control", U.S. Pat. No. 8,095,218 (Jan. 10, 2012 Gross et al.) "GI and Pancreatic Device for Treating Obesity and Diabetes", U.S. Pat. No. 8,135,470 (Mar. 13, 2012 Keimel et al.) "Energy Balance Therapy for Obesity Management", U.S. Pat. No. 8,209,037 (Jun. 26, 2012 Laufer et al.) "Methods and Devices for Medical Treatment", U.S. Pat. No. 8,321,030 (Nov. 27, 2012 Maniak et al.) "Esophageal Activity Modulated Obesity Therapy", U.S. Pat. No. 8,321,030 (Nov. 27, 2012 Maniak et al.) "Esophageal Activity Modulated Obesity Therapy", and U.S. Pat. No. 8,346,363 (Jan. 1, 2013 Darvish et al.) "Blood Glucose Level Control".

Examples of prior art that appear to be best classified in this category also include U.S. patent applications: 20040044376 (Mar. 4, 2004 Flesler et al.) "Acute and Chronic Electrical Signal Therapy for Obesity", 20050149142 (Jul. 7, 2005 Starkebaum) "Gastric Stimulation Responsive to Sensing Feedback", 20050222638 (Oct. 6, 2005 Foley et al.) "Sensor Based Gastrointestinal Electrical Stimulation for the Treatment of Obesity or Motility Disorders", 20060074459 (Apr. 6, 2006 Flesler et al.) "Acute and Chronic Electrical Signal Therapy for Obesity", 20070016262 (Jan. 18, 2007 Gross et al.) "GI and Pancreatic Device for Treating Obesity and Diabetes", 20070027493 (Feb. 1, 2007 Ben-Haim et al.) "Gastrointestinal Methods and Apparatus for Use in Treating Disorders and Controlling Blood Sugar", 20070179556 (Aug. 2, 2007 Ben-Haim et al.) "Gastrointestinal Methods and Apparatus for Use in Treating Disorders", 20070255334 (Nov. 1, 2007 Keimel et al.) "Energy Balance Therapy for Obesity Management", 20090018594 (Jan. 15, 2009 Laufer et al.) "Methods and Devices for Medical Treatment", 20090030474 (Jan. 29, 2009 Brynelsen et al.) "Sensor Driven Gastric Stimulation for Patient Management", 20090062881 (Mar. 5, 2009 Gross et al.) "GI and Pancreatic Device for Treating Obesity and Diabetes", 20090088816 (Apr. 2, 2009 Harel et al.) "Gastrointestinal Methods and Apparatus for Use in Treating Disorders and Controlling Blood Sugar", 20090240194 (Sep. 24, 2009 Keimel et al.) "Energy Balance Therapy for Obesity Management", 20100268306 (Oct. 21, 2010 Maniak et al.) "Esophageal Activity Modulated Obesity Therapy", 20110087076 (Apr. 14, 2011 Brynelsen et al.) "Feedback Systems and Methods for Communicating Diagnostic and/or Treatment Signals to Enhance Obesity Treatments", 20120083855 (Apr. 5, 2012 Gross et al.) "GI and Pancreatic Device for Treating Obesity and Diabetes", 20120214140 (Aug. 23, 2012 Brynelsen et al.) "Feedback Systems and Methods for Communicating Diagnostic and/or Treatment Signals to Enhance Obesity Treatments", 20120259389 (Oct. 11, 2012 Starkebaum et al.) "Treatment of Postprandial Hyperglycemia by Gastric Electrical Stimulation", and 20120323099 (Dec. 20, 2012 Mothilal et al.) "Implantable Medical Device Electrode Assembly".

37. Electrical Stimulation (with General Sensor)

Devices in this category are similar to devices in the prior category of general electrical stimulation except that they also include one or more sensors other than a glucose sensor. Like devices in prior categories, they deliver electromagnetic energy to person's gastrointestinal tract or to a nerve that innervates their gastrointestinal tract. In an example, the electromagnetic properties of a person's esophagus or stomach can be monitored by an electromagnetic sensor and gastrointestinal electrical stimulation can be triggered when the sensor indicates that a person is consuming food. Selective electrical stimulation can help to target therapeutic benefit.

Examples of prior art that appear to be best classified in this category include: U.S. Pat. No. 5,263,480 (Nov. 23, 1993 Wernicke et al.) "Treatment of Eating Disorders by Nerve Stimulation", U.S. Pat. No. 5,292,344 (Mar. 8, 1994 Douglas) "Percutaneously Placed Electrical Gastrointestinal Pacemaker Stimulatory System, Sensing System, and PH Monitoring System, with Optional Delivery Port", U.S. Pat. No. 5,540,730 (Jul. 30, 1996 Terry et al.) "Treatment of Motility Disorders by Nerve Stimulation", U.S. Pat. No. 5,836,994 (Nov. 17, 1998 Bourgeois) "Method and Apparatus for Electrical Stimulation of the Gastrointestinal Tract", U.S. Pat. No. 5,861,014 (Jan. 19, 1999 Familoni) "Method and Apparatus for Sensing a Stimulating Gastrointestinal Tract On-Demand", U.S. Pat. No. 5,995,872 (Nov. 30, 1999 Bourgeois) "Method and Apparatus for Electrical Stimulation of the Gastrointestinal Tract", U.S. Pat. No. 6,083,249 (Jul. 4, 2000 Familoni) "Apparatus for Sensing and Stimulating Gastrointestinal Tract On-Demand", U.S. Pat. No. 6,104,955 (Aug. 15, 2000 Bourgeois) "Method and Apparatus for Electrical Stimulation of the Gastrointestinal Tract", U.S. Pat. No. 6,115,635 (Sep. 5, 2000 Bourgeois) "Method and Apparatus for Electrical Stimulation of the Gastrointestinal Tract", U.S. Pat. No. 6,216,039 (Apr. 10, 2001 Bourgeois) "Method and Apparatus for Treating Irregular Gastric Rhythms", U.S. Pat. No. 6,327,503 (Dec. 4, 2001 Familoni) "Method and Apparatus for Sensing and Stimulating Gastrointestinal Tract On-Demand", U.S. Pat. No. 6,535,764 (Mar. 18, 2003 Imran et al.) "Gastric Treatment and Diagnosis Device and Method (Intrapace: Imran)", U.S. Pat. No. 6,591,137 (Jul. 8, 2003 Fischell et al.) "Implantable Neuromuscular Stimulator for the Treatment of Gastrointestinal Disorders", and U.S. Pat. No. 6,735,477 (May 11, 2004 Levine) "Internal Monitoring System with Detection of Food Intake".

Examples of prior art that appear to be best classified in this category also include: U.S. Pat. No. 6,826,428 (Nov. 30, 2004

Chen et al.) "Gastrointestinal Electrical Stimulation", U.S. Pat. No. 6,993,391 (Jan. 31, 2006 Flesler et al.) "Acute and Chronic Electrical Signal Therapy for Obesity", U.S. Pat. No. 7,054,690 (May 30, 2006 Imran) "Gastrointestinal Stimulation Device", U.S. Pat. No. 7,120,498 (Oct. 10, 2006 Imran et al.) "Method and Device for Securing a Functional Device to a Stomach", U.S. Pat. No. 7,430,450 (Sep. 30, 2008 Imran) "Device and Method for Treating Obesity", U.S. Pat. No. 7,437,195 (Oct. 14, 2008 Policker et al.) "Regulation of Eating Habits", U.S. Pat. No. 7,509,174 (Mar. 24, 2009 Imran et al.) "Gastric Treatment/Diagnosis Device and Attachment Device and Method", U.S. Pat. No. 7,620,454 (Nov. 17, 2009 Dinsmoor et al.) "Gastro-Electric Stimulation for Reducing the Acidity of Gastric Secretions or Reducing the Amounts Thereof", U.S. Pat. No. 7,643,887 (Jan. 5, 2010 Imran) "Abdominally Implanted Stimulator and Method", U.S. Pat. No. 7,702,394 (Apr. 20, 2010 Imran) "Responsive Gastric Stimulator", U.S. Pat. No. 7,738,961 (Jun. 15, 2010 Sharma) "Method and Apparatus for Treatment of the Gastrointestinal Tract", U.S. Pat. No. 7,742,818 (Jun. 22, 2010 Dinsmoor et al.) "Gastro-Electric Stimulation for Increasing the Acidity of Gastric Secretions or Increasing the Amounts Thereof", 7881797 (Feb. 1, 2011 Griffin et al.) "Methods and Devices for Gastrointestinal Stimulation", U.S. Pat. No. 7,941,221 (May 10, 2011 Foley) "Method and Apparatus for Intentional Impairment of Gastric Motility and/or Efficiency by Triggered Electrical Stimulation of the Gastrointestinal . . .", U.S. Pat. No. 8,214,049 (Jul. 3, 2012 Brynelsen et al.) "Gastric Stimulation Systems and Methods Utilizing a Transgastric Probe", and U.S. Pat. No. 8,239,027 (Aug. 7, 2012 Imran) "Responsive Gastric Stimulator".

Examples of prior art that appear to be best classified in this category also include U.S. patent applications: 20020072780 (Jun. 13, 2002 Foley) "Method and Apparatus for Intentional Impairment of Gastric Motility and/or Efficiency by Triggered Electrical Stimulation of the Gastrointestinal Tract . . . ", 20030009202 (Jan. 9, 2003 Levine) "Internal Monitoring System with Detection of Food Intake", 20040059393 (Mar. 25, 2004 Policker et al.) "Regulation of Eating Habits", 20040088023 (May 6, 2004 Imran et al.) "Gastric Treatment and Diagnosis Device and Method", 20040162595 (Aug. 19, 2004 Foley) "Method and Apparatus for Intentional Impairment of Gastric Motility and/or Efficiency by Triggered Electrical Stimulation of the Gastrointestinal Tract . . . ", 20050065571 (Mar. 24, 2005 Imran) "Responsive Gastric Stimulator", 20050090873 (Apr. 28, 2005 Imran) "Gastrointestinal Stimulation Device", 20060079944 (Apr. 13, 2006 Imran) "Device and Method for Treating Obesity", 20060089699 (Apr. 27, 2006 Imran) "Abdominally Implanted Stimulator and Method", 20070060812 (Mar. 15, 2007 Harel et al.) "Sensing of Pancreatic Electrical Activity", 20070162085 (Jul. 12, 2007 Dilorenzo) "Method Apparatus Surgical Technique and Stimulation Parameters for Autonomic Neuromodulation for the Treatment of Obesity", 20080058887 (Mar. 6, 2008 Griffin et al.) "Methods and Devices for Gastrointestinal Stimulation", 20080086179 (Apr. 10, 2008 Sharma) "Method and Apparatus for Treatment of the Gastrointestinal Tract", 20090018605 (Jan. 15, 2009 Imran et al.) "Gastric Treatment/Diagnosis Device and Attachment Device and Method", 20090018605 (Jan. 15, 2009 Imran et al.) "Gastric Treatment/Diagnosis Device and Attachment Device and Method", 20090030475 (Jan. 29, 2009 Brynelsen et al.) "Gastric Stimulation Systems and Methods Utilizing a Transgastric Probe", and 20090149910 (Jun. 11, 2009 Imran et al.) "Gastric Treatment/Diagnosis Device and Attachment Device and Method".

Examples of prior art that appear to be best classified in this category also include U.S. patent applications: 20090264951 (Oct. 22, 2009 Sharma) "Device and Implantation System for Electrical Stimulation of Biological Systems", 20100049274 (Feb. 25, 2010 Cholette) "Detection of Feeding Intent for Use in Treatment of Eating Disorders", 20100049274 (Feb. 25, 2010 Cholette) "Detection of Feeding Intent for Use in Treatment of Eating Disorders", 20100094374 (Apr. 15, 2010 Imran) "Responsive Gastric Stimulator", 20100305656 (Dec. 2, 2010 Imran et al.) "Gastric Stimulation Anchor and Method", 20100324432 (Dec. 23, 2010 Bjorling et al.) "Method and Device to Detect Eating to Control Artificial Gastric Stimulation", 20110004266 (Jan. 6, 2011 Sharma) "Method and Apparatus for Treatment of the Gastrointestinal Tract", 20110066207 (Mar. 17, 2011 Imran) "Responsive Gastric Stimulator", 20110125211 (May 26, 2011 Griffin et al.) "Methods and Devices for Gastrointestinal Stimulation", 20110251495 (Oct. 13, 2011 Province et al.) "Diagnostic Sensors and/or Treatments for Gastrointestinal Stimulation or Monitoring Devices", 20110295335 (Dec. 1, 2011 Sharma et al.) "Device and Implantation System for Electrical Stimulation of Biological Systems", 20110295336 (Dec. 1, 2011 Sharma et al.) "Device and Implantation System for Electrical Stimulation of Biological Systems", 20110307027 (Dec. 15, 2011 Sharma et al.) "Device and Implantation System for Electrical Stimulation of Biological Systems", 20110307028 (Dec. 15, 2011 Sharma et al.) "Device and Implantation System for Electrical Stimulation of Biological Systems", 20120277619 (Nov. 1, 2012 Starkebaum et al.) "Detecting Food Intake Based on Impedance", and 20120316451 (Dec. 13, 2012 Province et al.) "Event Evaluation Using Heart Rate Variation for Ingestion Monitoring and Therapy".

38. Electrical Stimulation (with Taste Modification)

Devices in this category are similar to devices in the prior category of general electrical stimulation except that they specifically modify a person's sense of taste. In an example, nerves that innervate a person's taste buds can be stimulated to modify a person's sense of taste and thereby modify their food consumption.

Examples of prior art that appear to be best classified in this category include U.S. patent applications: 20060173508 (Aug. 3, 2006 Stone et al.) "Method and System for Treatment of Eating Disorders by Means of Neuro-Electrical Coded Signals", 20060206169 (Sep. 14, 2006 Schuler) "Method and System for Modulating Eating Behavior by Means of Neuro-Electrical Coded Signals", 20060235487 (Oct. 19, 2006 Meyer et al.) "Method and System for Treatment of Eating Disorders by Means of Neuro-Electrical Coded Signals", 20110276112 (Nov. 10, 2011 Simon et al.) "Devices and Methods for Non-Invasive Capacitive Electrical Stimulation and Their Use for Vagus Nerve Stimulation on the Neck of a Patient", 20120029591 (Feb. 2, 2012 Simon et al.) "Devices and Methods for Non-Invasive Capacitive Electrical Stimulation and Their Use for Vagus Nerve Stimulation on the Neck of a Patient", 20120029601 (Feb. 2, 2012 Simon et al.) "Devices and Methods for Non-Invasive Capacitive Electrical Stimulation and Their Use for Vagus Nerve Stimulation on the Neck of a Patient", 20120277814 (Nov. 1, 2012 Schuler) "Method and System for Modulating Eating Behavior by Means of Neuro-Electrical Coded Signals", and 20120277837 (Nov. 1, 2012 Schuler) "Method and System for Modulating Eating Behavior by Means of Neuro-Electrical Coded Signals".

39. Electrical Stimulation (with Drug)

Devices in this category are similar to devices in the prior category of general electrical stimulation except that they also include a drug delivery mechanism. In addition to delivering electromagnetic energy to person's gastrointestinal tract or to a nerve that innervates their gastrointestinal tract, devices in this category can also include an implantable drug pump. In an example, electrical stimulation can be used in conjunction with drug delivery to create combined therapeutic effects.

Examples of prior art that appear to be best classified in this category include: U.S. Pat. No. 5,782,798 (Jul. 21, 1998 Rise) "Techniques for Treating Eating Disorders by Brain Stimulation and Drug Infusion", U.S. Pat. No. 7,493,171 (Feb. 17, 2009 Whitehurst et al.) "Treatment of Pathologic Craving and Aversion Syndromes and Eating Disorders by Electrical Brain Stimulation and/or Drug Infusion", U.S. Pat. No. 7,835,796 (Nov. 16, 2010 Maschino et al.) "Weight Loss Method and Device", U.S. Pat. No. 8,010,204 (Aug. 30, 2011 Knudson et al.) "Nerve Blocking for Treatment of Gastrointestinal Disorders", U.S. Pat. No. 8,185,206 (May 22, 2012 Starkebaum et al.) "Electrical Stimulation Therapy to Promote Gastric Distention for Obesity Management", and U.S. Pat. No. 8,295,926 (Oct. 23, 2012 Dobak) "Dynamic Nerve Stimulation in Combination with Other Eating Disorder Treatment Modalities"; and U.S. patent applications 20080021512 (Jan. 24, 2008 Knudson et al.) "Nerve Stimulation and Blocking for Treatment of Gastrointestinal Disorders", 20080262411 (Oct. 23, 2008 Dobak) "Dynamic Nerve Stimulation in Combination with Other Eating Disorder Treatment Modalities", 20110282411 (Nov. 17, 2011 Knudson et al.) "Nerve Stimulation and Blocking for Treatment of Gastrointestinal Disorders", 20110282411 (Nov. 17, 2011 Knudson et al.) "Nerve Stimulation and Blocking for Treatment of Gastrointestinal Disorders", and 20120277661 (Nov. 1, 2012 Bernard et al.) "Method and Apparatus for Delivery of Therapeutic Agents".

40. Electrical Stimulation (with Drug and Sensor)

Devices in this category are similar to devices in a prior category of general electrical stimulation except that they also include a drug delivery mechanism and at least one sensor. In an example, electrical stimulation can be used in conjunction with drug delivery to create combined therapeutic effects. Further, the sensor can be used to create a self-adjusting, closed-loop stimulation and/or drug delivery system for modification of food consumption.

Examples of prior art that appear to be best classified in this category include: U.S. Pat. No. 6,950,707 (Sep. 27, 2005 Whitehurst) "Systems and Methods for Treatment of Obesity and Eating Disorders by Electrical Brain Stimulation and/or Drug Infusion", U.S. Pat. No. 7,076,305 (Jul. 11, 2006 Imran et al.) "Gastric Device and Instrument System and Method", U.S. Pat. No. 7,483,746 (Jan. 27, 2009 Lee et al.) "Stimulation of the Stomach in Response to Sensed Parameters to Treat Obesity", U.S. Pat. No. 7,590,452 (Sep. 15, 2009 Imran et al.) "Endoscopic System for Attaching a Device to a Stomach", and U.S. Pat. No. 8,095,219 (Jan. 10, 2012 Lee et al.) "Stimulation of the Stomach in Response to Sensed Parameters to Treat Obesity"; and U.S. patent applications 20030167024 (Sep. 4, 2003 Imran et al.) "Gastric Device and Instrument System and Method", 20040243195 (Dec. 2, 2004 Imran et al.) "Endoscopic System for Attaching a Device to a Stomach", 20060129201 (Jun. 15, 2006 Lee et al.) "Stimulation of the Stomach in Response to Sensed Parameters to Treat Obesity", and 20090299434 (Dec. 3, 2009 Imran et al.) "Endoscopic System for Attaching a Device to a Stomach".

41. Salivation Stimulation

This category of prior art includes devices and methods for stimulating salivation in a person's mouth. In some respects, this is quite different than devices and methods that are intended to reduce food consumption. Most devices and methods in this category are focused on increasing, not decreasing, food consumption. However, this category is included for completeness because some of these devices are intended to modify the early stages of food digestion within a person's mouth, which can be relevant. In an example, devices in this category can apply electrical stimulation to the mouth to increase salivation. In an example, devices in this category can release a salivation-stimulating substance.

Examples of prior art that appear to be best classified in this category include: U.S. Pat. No. 4,519,400 (May 28, 1985 Brenman et al.) "Method for Stimulating Salivation (Biosonics)", U.S. Pat. No. 4,637,405 (Jan. 20, 1987 Brenman et al.) "Apparatus for Stimulating Salivation", U.S. Pat. No. 6,230,052 (May 8, 2001 Wolff et al.) "Device and Method for Stimulating Salivation", U.S. Pat. No. 7,041,311 (May 9, 2006 Grainger et al.) "Preparation for Saliva Flow", and U.S. Pat. No. 7,477,947 (Jan. 13, 2009 Pines et al.) "System and Method for Electrical Stimulation of Salivation"; and U.S. patent application 20070077300 (Apr. 5, 2007 Wynn et al.) "Oral Compositions Containing a Salivation Inducing Agent".

42. General Sensor (Glucose)

This category of prior art includes sensors and monitors which detect and analyze glucose levels (such as blood glucose levels). These sensors and monitors can be used for a variety of applications other than modification of food consumption or food absorption. For example, they can be used to determine when a diabetic person needs insulin. Nonetheless, overall, they are sufficiently relevant to be included in this review.

Examples of prior art that appear to be best classified in this category include: U.S. Pat. No. 5,497,772 (Mar. 12, 1996 Schulman et al.) "Glucose Monitoring System", U.S. Pat. No. 7,727,147 (Jun. 1, 2010 Osorio et al.) "Method and System for Implantable Glucose Monitoring and Control of a Glycemic State of a Subject", U.S. Pat. No. 7,974,672 (Jul. 5, 2011 Shults et al.) "Device and Method for Determining Analyte Levels", U.S. Pat. No. 7,988,630 (Aug. 2, 2011 Osorio et al.) "Method and System for Implantable Glucose Monitoring and Control of a Glycemic State of a Subject", U.S. Pat. No. 8,158,082 (Apr. 17, 2012 Imran) "Micro-Fluidic Device", U.S. Pat. No. 8,236,242 (Aug. 7, 2012 Drucker et al.) "Blood Glucose Tracking Apparatus and Methods", U.S. Pat. No. 8,275,438 (Sep. 25, 2012 Simpson et al.) "Analyte Sensor", U.S. Pat. No. 8,287,453 (Oct. 16, 2012 Li et al.) "Analyte Sensor", and U.S. Pat. No. 8,298,142 (Oct. 30, 2012 Simpson et al.) "Analyte Sensor"; and U.S. patent applications 20050096637 (May 5, 2005 Heruth) "Sensing Food Intake", 20120078071 (Mar. 29, 2012 Bohm et al.) "Advanced Continuous Analyte Monitoring System", 20120149996 (Jun. 14, 2012 Stivoric et al.) "Method and Apparatus for Providing Derived Glucose Information Utilizing Physiological and/or Contextual Parameters", and 20120201725 (Aug. 9, 2012 Imran) "Micro-Fluidic Device".

43. General Sensor (Electromagnetic)

This category of prior art includes sensors and monitors which detect selected patterns of electromagnetic energy that are emitted from a member of a person's body. Such sensors and monitors can be used for a variety of applications other than modification of food consumption or food absorption. Nonetheless, overall, they are sufficiently relevant to be included in this review.

Examples of prior art that appear to be best classified in this category include: U.S. Pat. No. 5,795,304 (Aug. 18, 1998 Sun et al.) "System and Method for Analyzing Electrogastrophic Signal", U.S. Pat. No. 6,285,897 (Sep. 4, 2001 Kilcoyne et al.) "Remote Physiological Monitoring System", U.S. Pat. No. 8,192,350 (Jun. 5, 2012 Ortiz et al.) "Methods and Devices for Measuring Impedance in a Gastric Restriction System", U.S. Pat. No. 8,265,758 (Sep. 11, 2012 Policker et al.) "Wireless Leads for Gastrointestinal Tract Applications", and U.S. Pat. No. 8,328,420 (Dec. 11, 2012 Abreu) "Apparatus and Method for Measuring Biologic Parameters"; and U.S. patent applications 20080262557 (Oct. 23, 2008 Brown) "Obesity Management System", 20090281449 (Nov. 12, 2009 Thrower et al.) "Optimization of Thresholds for Eating Detection", 20100305468 (Dec. 2, 2010 Policker et al.) "Analysis and Regulation of Food Intake", and 20120316459 (Dec. 13, 2012 Abreu) "Apparatus and Method for Measuring Biologic Parameters".

44. General Sensor (Chemical)

This category of prior art includes sensors which can detect specific types of chemicals. Such sensors can be used for a variety of applications other than modification of food consumption or food absorption. Some are not even directed toward biomedical applications. Nonetheless, overall, they are sufficiently relevant to be included in this review.

Examples of prior art that appear to be best classified in this category include: U.S. Pat. No. 6,218,358 (Apr. 17, 2001 Firestein et al.) "Functional Expression of, and Assay for, Functional Cellular Receptors In Vivo", U.S. Pat. No. 6,387,329 (May 14, 2002 Lewis et al.) "Use of an Array of Polymeric Sensors of Varying Thickness for Detecting Analytes in Fluids", U.S. Pat. No. 6,610,367 (Aug. 26, 2003 Lewis et al.) "Use of an Array of Polymeric Sensors of Varying Thickness for Detecting Analytes in Fluids", U.S. Pat. No. 7,122,152 (Oct. 17, 2006 Lewis et al.) "Spatiotemporal and Geometric Optimization of Sensor Arrays for Detecting Analytes Fluids", U.S. Pat. No. 7,241,880 (Jul. 10, 2007 Adler et al.) "T1R Taste Receptors and Genes Encoding Same", U.S. Pat. No. 7,595,023 (Sep. 29, 2009 Lewis et al.) "Spatiotemporal and Geometric Optimization of Sensor Arrays for Detecting Analytes in Fluids", U.S. Pat. No. 7,651,868 (Jan. 26, 2010 Mcdevitt et al.) "Method and System for the Analysis of Saliva using a Sensor Array", U.S. Pat. No. 8,067,185 (Nov. 29, 2011 Zoller et al.) "Methods of Quantifying Taste of Compounds for Food or Beverages", U.S. Pat. No. 8,314,224 (Nov. 20, 2012 Adler et al.) "T1R Taste Receptors and Genes Encoding Same", and U.S. Pat. No. 8,334,367 (Dec. 18, 2012 Adler) "T2R Taste Receptors and Genes Encoding Same"; and U.S. patent applications 20090261987 (Oct. 22, 2009 Sun) "Sensor Instrument System Including Method for Detecting Analytes in Fluids", and 20120015432 (Jan. 19, 2012 Adler) "Isolated Bitter Taste Receptor Polypeptides".

45. General Sensor (Microwave)

This category of prior art includes sensors which can detect selected patterns of microwave energy. Such sensors can be used for a variety of applications other than modification of food consumption or food absorption. Nonetheless, overall, they are sufficiently relevant to be included in this review. Examples of prior art that appear to be best classified in this category include U.S. patent applications 20120053426 (Mar. 1, 2012 Webster et al.) "System and Method for Measuring Calorie Content of a Food Sample" and 20130027060 (Jan. 31, 2013 Tralshawala et al.) "Systems and Methods for Non-Destructively Measuring Calorie Contents of Food Items".

46. Sensor (Intraoral)

This category of prior art includes sensors and monitors which are specifically attached or implanted within a person's oral cavity. Examples of prior art that appear to be best classified in this category include: U.S. Pat. No. 8,233,954 (Jul. 31, 2012 Kling et al.) "Mucosal Sensor for the Assessment of Tissue and Blood Constituents and Technique for Using the Same"; and U.S. patent applications 20050263160 (Dec. 1, 2005 Utley et al.) "Intraoral Aversion Devices and Methods", 20060020298 (Jan. 26, 2006 Camilleri et al.) "Systems and Methods for Curbing Appetite", 20070106138 (May 10, 2007 Beiski et al.) "Intraoral Apparatus for Non-Invasive Blood and Saliva Monitoring & Sensing", and 20100209897 (Aug. 19, 2010 Utley et al.) "Intraoral Behavior Monitoring and Aversion Devices and Methods".

47. Sensor (General)

This category of prior art includes general sensors which can be used for a variety of applications other than modification of food consumption or food absorption. Nonetheless, overall, they are sufficiently relevant to merit inclusion in this review.

Examples of prior art that appear to be best classified in this category include: U.S. Pat. No. 4,823,808 (Apr. 25, 1989 Clegg et al.) "Method for Control of Obesity Overweight and Eating Disorders", U.S. Pat. No. 5,301,679 (Apr. 12, 1994 Taylor) "Method and System for Analysis of Body Sounds", U.S. Pat. No. 6,365,128 (Apr. 2, 2002 Bennett-Guerrero et al.) "Monitoring Gastrointestinal Function to Guide Care of High Risk Patients", and U.S. Pat. No. 7,832,407 (Nov. 16, 2010 Gertner) "Obesity Treatment Systems"; and U.S. patent applications 20060089571 (Apr. 27, 2006 Gertner) "Obesity Treatment Systems", 20090118797 (May 7, 2009 Kliger et al.) "Monitoring, Analysis, and Regulation of Eating Habits", 20100160745 (Jun. 24, 2010 Hills et al.) "Detection of Food or Drink Consumption in Order to Control Therapy or Provide Diagnostics", 20120116182 (May 10, 2012 Wong et al.) "Feedback Systems and Methods to Enhance Obstructive and Other Obesity Treatments, Optionally Using Multiple Sensors", and 20120232361 (Sep. 13, 2012 Birk) "Bariatric Instrument or Accessory with Sensors".

48. Blood Analysis and Monitoring

Prior art in this category includes devices and methods that analyze the flow and/or composition of a person's blood. In an example, a sensor can infer whether a person is consuming food by monitoring blood flow through tissue that is related to food consumption and digestion.

Examples of prior art that appear to be best classified in this category include: U.S. Pat. No. 5,398,688 (Mar. 21, 1995 Laniado) "Method, System and Instrument for Monitoring Food Intake", U.S. Pat. No. 6,893,406 (May 17, 2005 Takeuchi et al.) "Mastication Monitoring Device", and U.S. Pat. No. 7,006,871 (Feb. 28, 2006 Darvish et al.) "Blood Glucose Level Control"; and U.S. patent applications 20040073142 (Apr. 15, 2004 Takeuchi et al.) "Mastication Monitoring Device", and 20110218407 (Sep. 8, 2011 Haberman et al.) "Method and Apparatus to Monitor, Analyze and Optimize Physiological State of Nutrition".

49. General Energy Balance Feedback

This category of prior art includes a wide variety of relatively-general systems, devices, and methods that are intended to provide a person with support and feedback concerning their energy balance and weight management. In various examples, systems, devices, and methods in this category can involve: general feedback and behavior modification concerning diet and exercise patterns; broadly-defined use of general types of sensors for energy balance and weight management; interactive communication between people and healthcare providers, or between people and social support networks; internet websites that provide online support for energy balance and weight management; and general meal planning systems and methods. Much of the prior art in this category can be very useful, but is very general compared to the specificity of this present invention. Nonetheless, this general category is included in this review in order to be thorough.

Examples of prior art that appear to be best classified in this category include: U.S. Pat. No. 4,951,197 (Aug. 21, 1990 Mellinger) "Weight Loss Management System", U.S. Pat. No. 5,720,771 (Feb. 24, 1998 Snell) "Method and Apparatus for Monitoring Physiological Data from an Implantable Medical Device", U.S. Pat. No. 6,154,676 (Nov. 28, 2000 Levine) "Internal Monitoring and Behavior Control System (Robert Levine)", U.S. Pat. No. 6,334,073 (Dec. 25, 2001 Levine) "Internal Monitoring and Behavior Control System", U.S. Pat. No. 6,735,479 (May 11, 2004 Fabian et al.) "Lifestyle Management System", U.S. Pat. No. 7,247,023 (Jul. 24, 2007 Peplinski et al.) "System and method for monitoring weight and nutrition (Daniel Peplinski)", and U.S. Pat. No. 7,882,150 (Feb. 1, 2011 Badyal) "Health Advisor"; and U.S. patent applications 20050113649 (May 26, 2005 Bergantino) "Method and Apparatus for Managing a User's Health", 20060015016 (Jan. 19, 2006 Thornton) "Caloric Balance Weight Control System and Methods of Making and Using Same", 20060122468 (Jun. 8, 2006 Tavor) "Nutritional Counseling Method and Server", 20070021979 (Jan. 25, 2007 Cosentino et al.) "Multiuser Wellness Parameter Monitoring System", 20080221644 (Sep. 11, 2008 Vallapureddy et al.) "Remote Monitoring and Control of Implantable Devices", and 20120065706 (Mar. 15, 2012 Vallapureddy et al.) "Remote Monitoring and Control of Implantable Devices".

50. Miscellaneous Energy Balance Related Devices and Methods

Lastly, this category of prior art includes a variety of devices and methods that may be generally relevant to the measurement and modification of food consumption, but which resist neat categorization. Examples of prior art in this miscellaneous category include: altering food perception through the use of special tableware; devices that a person activates to emit a bad smell to reduce their appetite; devices that a person uses to shock their tongue when they have a craving; devices to increase airflow through the nose; methods for identifying olfactory cells; time-restricted food containers to control access to food; and using tongue stimulation as a sensory substitute for vision.

Examples of prior art that appear to be best classified in this category include: U.S. Pat. No. 4,582,492 (Apr. 15, 1986 Etter et al.) "Method for Behavior Modification Using Olfactory Stimuli", U.S. Pat. No. 5,792,210 (Aug. 11, 1998 Wamubu et al.) "Electrical Tongue Stimulator and Method for Addiction Treatment", U.S. Pat. No. 6,145,503 (Nov. 14, 2000 Smith) "Olfactory Activator", U.S. Pat. No. 6,159,145 (Dec. 12, 2000 Satoh) "Appetite Adjusting Tool", U.S. Pat. No. 7,409,647 (Aug. 5, 2008 Elber et al.) "Control of Interactions Within Virtual Environments", and U.S. Pat. No. 8,060,220 (Nov. 15, 2011 Liebergesell et al.) "Promotion of Oral Hygiene and Treatment of Gingivitis Other Periodontal Problems and Oral Mal Odor".

Examples of prior art that appear to be best classified in this category also include U.S. patent applications: 20020049482 (Apr. 25, 2002 Fabian et al.) "Lifestyle Management System", 20040186528 (Sep. 23, 2004 Ries et al.) "Subcutaneous Implantable Medical Devices with Anti-Microbial Agents for Chronic Release", 20050146419 (Jul. 7, 2005 Porter) "Programmable Restricted Access Food Storage Container and Behavior Modification Assistant", 20050240253 (Oct. 27, 2005 Tyler et al.) "Systems and Methods for Altering Vestibular Biology", 20080141282 (Jun. 12, 2008 Elber et al.) "Control of Interactions Within Virtual Environments", 20080270947 (Oct. 30, 2008 Elber et al.) "Control of Interactions Within Virtual Environments", 20090197963 (Aug. 6, 2009 Llewellyn) "Method and Compositions for Suppressing Appetite or Treating Obesity", 20090312817 (Dec. 17, 2009 Hogle et al.) "Systems and Methods for Altering Brain and Body Functions and for Treating Conditions and Diseases of the Same", 20100055245 (Mar. 4, 2010 Havekotte et al.) "Modifying Flavor Experience Via Aroma Delivery", 20100291515 (Nov. 18, 2010 Pinnisi et al.) "Regulating Food and Beverage Intake", 20110314849 (Dec. 29, 2011 Park et al.) "Storage Container with Sensor Device and Refrigerator Having the Same", 20120009551 (Jan. 12, 2012 Pinnisi) "Cues to Positively Influence Eating Habits", 20120036875 (Feb. 16, 2012 Yun et al.) "Storage Container with Sensor Device and Refrigerator Having the Same", and 20120299723 (Nov. 29, 2012 Hafezi et al.) "Communication System Incorporated in a Container".

SUMMARY OF THIS INVENTION

This invention is a device and method for adjustably and reversibly reducing nutrient absorption from food passing through a person's gastrointestinal tract using an Adjustable Gastrointestinal Bifurcation (AGB) and a flow-control member. The Adjustable Gastrointestinal Bifurcation (AGB) includes: a first food-flow route (comprising a first branch of the AGB) through the person's gastrointestinal tract wherein there is normal absorption of nutrients from food; and a second food-flow route (comprising a second branch of the AGB) through the person's gastrointestinal tract wherein there is reduced absorption of nutrients from food.

The flow-control member adjusts the types and/or amounts of food which are diverted through the second food-flow route versus the first food-flow route. In an example, a flow-control member can be used to manually adjust the types and/or amounts of food going through the first versus second routes in a minimally-invasive or non-invasive manner. In an example, a flow-control member can automatically direct healthy types and/or amounts of food through the first food-flow route for normal nutrient absorption and automatically direct unhealthy types and/or amounts of food through the second food-flow route for reduced nutrient absorption.

This invention can encourage a person to eat healthy types and/or amounts of food. This invention can also help a person to lose weight without the nutritional deficiencies that can accompany food-blind bariatric procedures and devices in the prior art that blindly reduce absorption of nutrients from both healthy and unhealthy food. This novel invention addresses several limitations of the prior art in this field and provides a number of advantages over the prior art for energy balance, weight management, and proper nutrition. Further, its novel features are not anticipated by the prior art.

INTRODUCTION TO THE FIGURES

FIGS. 1 and 2 show two sequential views of an example of this invention that can adjustably and reversibly reduce nutrient absorption from food passing through a person's gastrointestinal tract using an Adjustable Gastrointestinal Bifurcation (AGB).

FIG. 1 shows an example of how this device can channel healthy food through a normal-absorption route through a person's stomach.

FIG. 2 shows an example of how this device can selectively and automatically channel unhealthy food through a reduced-absorption route through the person's stomach.

FIGS. 3 and 4 show two sequential views of another example of this invention that can adjustably and reversibly reduce nutrient absorption from food passing through a person's gastrointestinal tract using an Adjustable Gastrointestinal Bifurcation (AGB).

FIG. 3 shows an example of how this device can channel healthy food through a normal-absorption route through a person's stomach and duodenum.

FIG. 4 shows an example of how this device can selectively and automatically channel unhealthy food through a reduced-absorption route through the person's stomach and duodenum.

FIGS. 5 and 6 show two sequential views of another example of this invention that can adjustably and reversibly reduce nutrient absorption from food passing through a person's gastrointestinal tract using an Adjustable Gastrointestinal Bifurcation (AGB).

FIG. 5 shows an example of how this device can channel healthy food through a normal-absorption route through a person's stomach and duodenum.

FIG. 6 shows an example of how this device can selectively and automatically channel unhealthy food through a gastric bypass.

FIGS. 7 and 8 show an example of how this invention can include a flow-control member that can be adjusted in a non-invasive manner by wireless communication with an external control device.

FIGS. 9 and 10 show an example of how this invention can include an intraoral sensor.

FIG. 11 shows a close-up view of an example of a flow-control member with an adjustable flap valve.

FIGS. 12 and 13 show close-up views of an example of a flow-control member with a bent-disk flap.

DETAILED DESCRIPTION OF THE FIGURES

Figure 1:
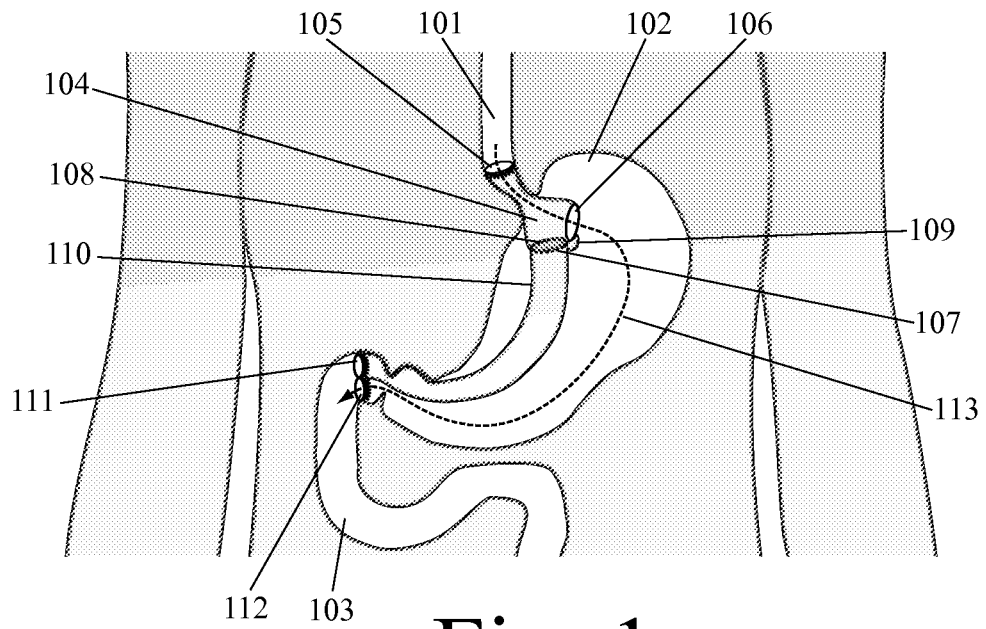
FIGS. 1 through 13 show some examples of how this invention can be embodied, but they do not limit the full generalizability of the claims.
Figure 2:
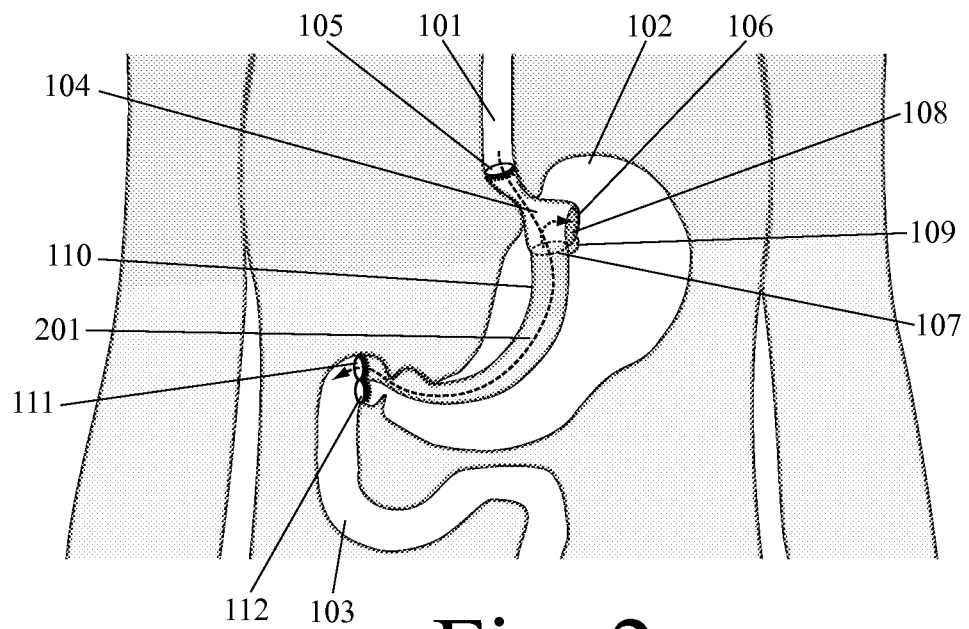

Before we discuss the specific components of FIGS. 1 and 2, it is helpful to first give an overall conceptual introduction to the embodiment of this invention that is shown in these figures. FIGS. 1 and 2 show two sequential views (at two different times) of this embodiment comprising a device that can adjustably and reversibly reduce nutrient absorption from food passing through a person's gastrointestinal tract using an Adjustable Gastrointestinal Bifurcation (AGB). This Adjustable Gastrointestinal Bifurcation (AGB) includes: a first food-flow route (comprising a first branch of the AGB) through the person's gastrointestinal tract wherein there is normal absorption of nutrients from food; and a second food-flow route (comprising a second branch of the AGB) through the person's gastrointestinal tract wherein there is reduced absorption of nutrients from food. In this example, the second food-flow route is a gastric sleeve with relatively-impermeable walls.

The example of this invention that is shown in FIGS. 1 and 2 also includes a flow-control member that controls food flow through the branches of the Adjustable Gastrointestinal Bifurcation (AGB). This flow-control member adjusts the types and/or amounts of food which are diverted through the second food-flow route versus the first food-flow route. In this example, the flow-control member can be used to manually adjust the types and/or amounts of food going through the first versus second routes in a minimally-invasive or non-invasive manner. As we will discuss, manual flow adjustment can be done in non-invasive manner using wireless communication between the flow-control member and an external device. As we will also discuss, automatic flow adjustment can occur through interaction between the flow-control member and a food-consumption sensor. A food-consumption sensor can be part of the flow-control member or can be located elsewhere.

We now discuss in greater detail the specific components that are shown in FIG. 1. FIG. 1 shows a longitudinal cross-sectional view of a person's torso, including the person's esophagus 101, stomach 102, and intestine 103. FIG. 1 also shows a flow-control member 104 which has been implanted into the person's gastrointestinal tract at the intersection of the esophagus 101 and stomach 102. Flow-control member 104 can adjustably divert food flow through a first normal-absorption food-flow route versus a second reduced-absorption food-flow route. In this example, there is a proximal ring 105 at the upstream end of flow-control member 104 that engages the walls of esophagus 101. Food descending through esophagus 101 enters flow control member 104 through proximal ring 105.

FIG. 1 also shows a first opening 106 and a second opening 107 at the bifurcated downstream end of flow-control member 104. Food that enters first opening 106 flows through a first food-flow route with normal nutrient absorption. Food that enters second opening 107 flows through a second food-flow route with reduced nutrient absorption. In this example, the first food-flow route is the greater interior space (greater curve) of stomach 102 which generally comprises the path that food would normally travel through this portion of the person's gastrointestinal tract. In this example, the second food-flow route is a gastric sleeve 110 with fluid-impermeable walls that generally bypasses the greater interior space of the person's stomach 102. Unlike common surgical procedures and bariatric devices in the prior art, both of these food-flow routes are optionally available post-operatively for receiving food flow (thereby forming an Adjustable Gastrointestinal Bifurcation) and the relative types and/or amounts of food that flow through these two alternative routes can be post-operatively and reversibly adjusted in a minimally-invasive or automatic manner.

FIG. 1 also shows an adjustable flap valve 108 (which, in this example, is located within flow-control member 104). Adjustable flap valve 108 can be adjusted to selectively block first opening 106 or second opening 107. In FIG. 1, adjustable flap valve 108 is shown as blocking second opening 107, thereby causing food to enter first opening 106 and to flow through the first food-flow route. In this example, the first food-flow route is through the greater interior space of the person's stomach 102. In FIG. 1, the flow of food through this first food-flow route is represented by dotted-line arrow 113. In FIG. 1, food descending through esophagus 101 is channeled through flow-control member 104 into first opening 106, then through the greater interior space of stomach 102, then through downstream ring 112, and then onward into intestine 103.

In the embodiment of this invention that is shown in FIGS. 1 and 2, adjustable flap valve 108 is moved by valve actuator 109. In this example, the flow-control member 104 comprises separately-identifiable components including: proximal ring 105; first opening 106; second opening 107; adjustable flap valve 108; and valve actuator 109. As we will discuss in more detail in subsequent figures, a flow-control member can also comprise other components including: a food-consumption sensor, a Central Processing Unit (CPU), a power source, and a wireless signal transmitter/receiver.

FIG. 2 shows the same embodiment of this invention that is shown in FIG. 1, but at a different time wherein the flow-control member 104 has diverted the flow of food. In FIG. 2, flow-control member 104 is now directing food flow through the second reduced-absorption food-flow route. Specifically, FIG. 2 shows that adjustable flap valve 108 has been rotated by valve actuator 109 to block first opening 106 instead of second opening 107. This causes food to flow through the second food-flow route instead of the first food-flow route. In FIG. 2, food descending through esophagus 101 enters flow-control member 104 and is directed to flow through second food-flow route 110 until it exits downstream ring 111. In FIG. 2, food flowing through the second food-flow route is represented by dotted-line arrow 201.

In the example shown in FIG. 2, the second food-flow route is a gastric sleeve 110 with fluid-impermeable walls. Food that travels through the second food-flow route (gastric sleeve 110) has less fluid communication with gastric fluids and thus lower nutrient-absorption than food that travels through the first food-flow route (the greater portion of the interior of stomach 102).

Figure 3:
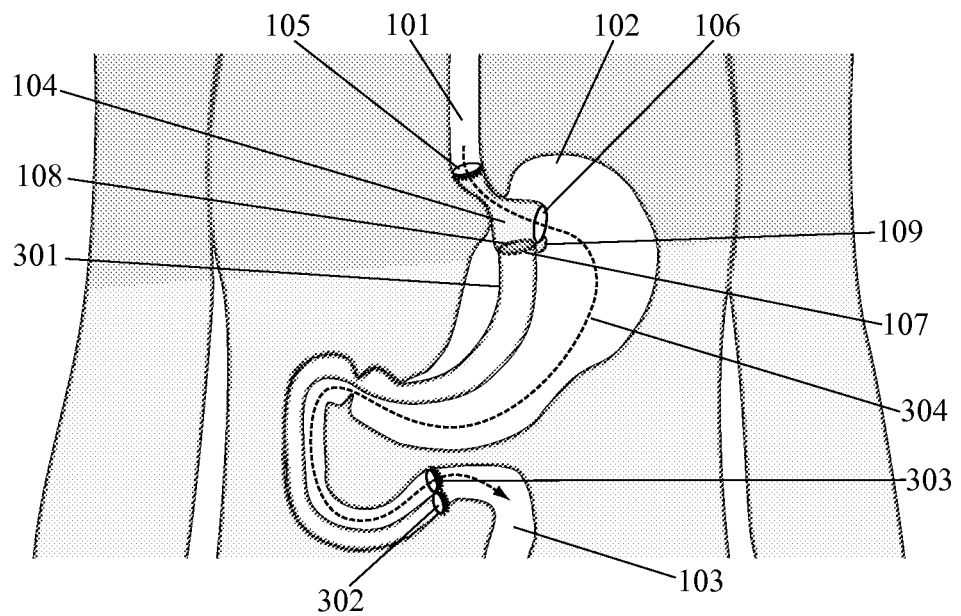
Figure 4:
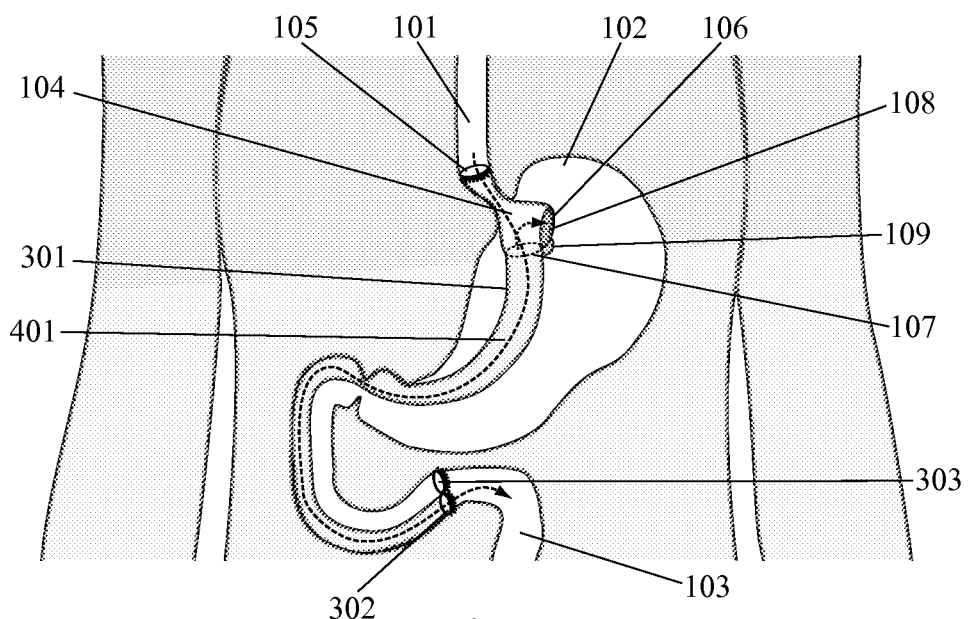

FIGS. 3 and 4 show two sequential views (at two different times) of another embodiment of this invention. This embodiment is similar to the embodiment that was shown in FIGS. 1 and 2, except that in FIGS. 3 and 4 the second food-flow route is now a gastrointestinal sleeve 301 that extends through a portion of the person's intestine 103 in addition to the interior of the person's stomach 102. There is less absorption of nutrients from food that travels through a longer gastrointestinal sleeve 301 (that extends through a portion of a person's intestine as well as their stomach) as compared to a shorter gastric sleeve 110 (that only extends through their stomach). Accordingly, absorption of nutrients from food traveling through the second food-flow route in FIG. 4 is even less than that of food traveling through the second food-flow route in FIG. 2.

The components in FIGS. 3 and 4 that are different from the components already discussed in the context of FIGS. 1 and 2 including the following. In FIGS. 3 and 4, the second food-flow route 301 is a gastrointestinal sleeve with an upstream end at the top of stomach 102 and a downstream end (downstream ring 302) located some distance into the person's intestine 103. In an example, second food-flow route 301 can be a sleeve that extends through the person's stomach and duodenum.

In FIG. 3, adjustable flap valve 108 covers second opening 107 so that the flow of food is directed through a first food-flow route comprising the greater interior of the person's stomach and duodenum. The flow of food through the first food-flow route is shown in FIG. 3 by dotted-line arrow 304. In FIG. 4, adjustable flap valve 108 has been rotated by valve actuator 109 to cover first opening 106 so that the flow of food is directed through a second food-flow route comprising a gastrointestinal sleeve that spans the person's stomach and duodenum. This sleeve reduces absorption of nutrients from food that travels through the sleeve because the walls of the sleeve reduce fluid communication between food and the gastrointestinal tract walls. The flow of food through the second food-flow route is shown in FIG. 4 by dotted-line arrow 401.

Figure 5:
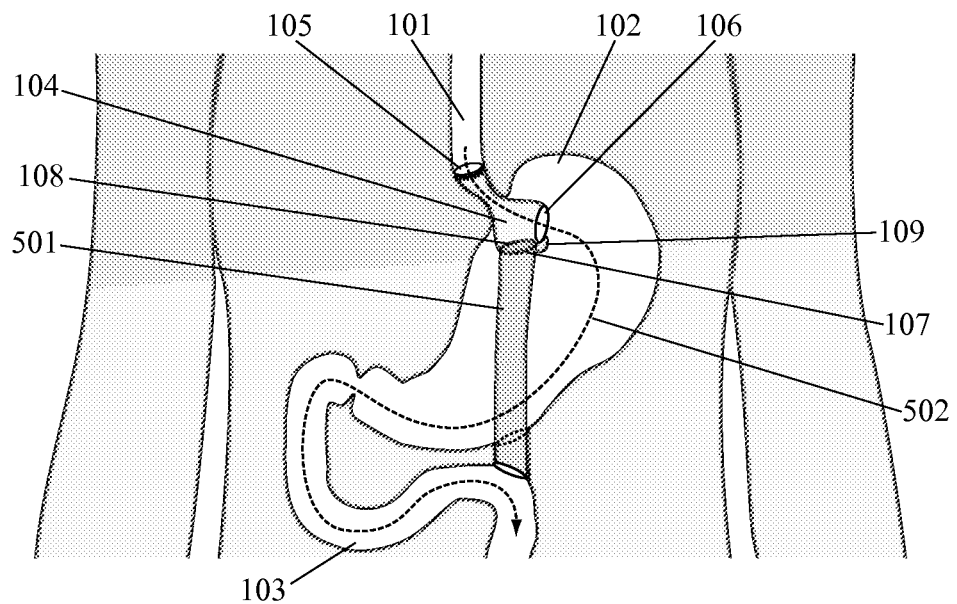
Figure 6:
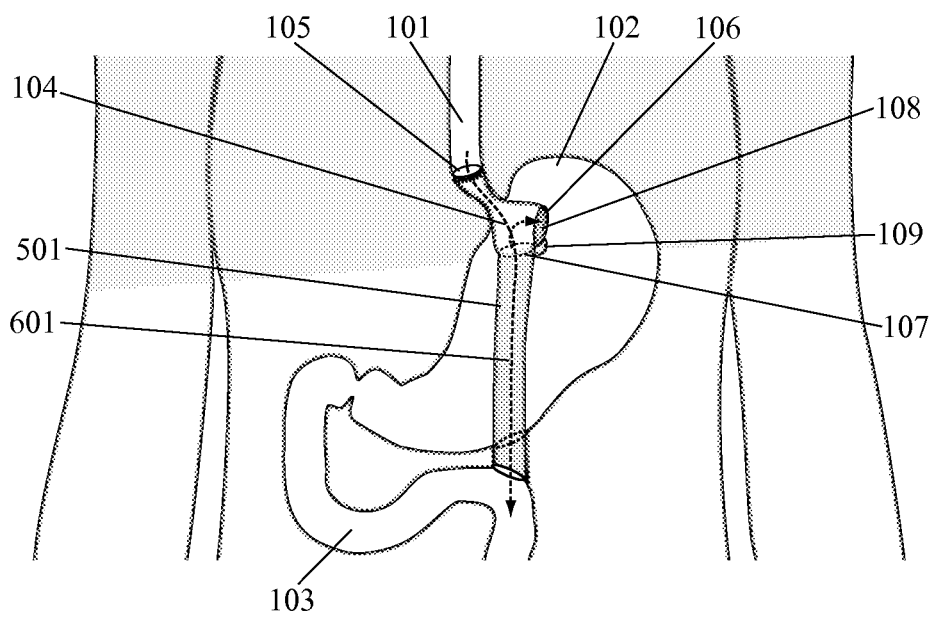

FIGS. 5 and 6 show two sequential views (at two different times) of another embodiment of this invention. The flow-control member of this embodiment is similar to the flow-control member shown in previous figures, but in FIGS. 5 and 6 the second food-flow route is a gastrointestinal bypass 501 that connects the flow-control member (at top of the person's stomach) directly to the end of the person's duodenum. In an example, gastrointestinal bypass 501 can be a lumen that is made from artificial materials. In an example, gastrointestinal bypass 501 can be a lumen that is made from biological tissue or other natural materials. In an example, gastrointestinal bypass 501 can be autologous tissue from a portion of the person's own gastrointestinal tract.

A potential disadvantage of using a direct gastrointestinal bypass as the second food-flow route (instead of a gastrointestinal sleeve as in prior examples) is that a bypass can be more invasive. However, a potential advantage of using a direct gastrointestinal bypass as the second food-flow route is that it can reduce nutritional absorption even further. Also, having a direct gastrointestinal bypass can avoid having first and second food-flow routes overlap within the duodenum. This can avoid having one flow traveling outside a gastrointestinal sleeve and one flow traveling inside a gastrointestinal sleeve.

In FIG. 5, adjustable flap valve 108 covers second opening 107 so that the flow of food is directed through a first food-flow route comprising the greater interior of the person's stomach and duodenum. The flow of food through the first food-flow route is shown in FIG. 5 by dotted-line arrow 502. In FIG. 6, adjustable flap valve 108 has been rotated by valve actuator 109 to cover first opening 106 so that the flow of food is directed through a gastrointestinal bypass 501, bypassing the greater interior of person's stomach and duodenum. The flow of food through the second food-flow route is shown in FIG. 6 by dotted-line arrow 601.

Figure 7:
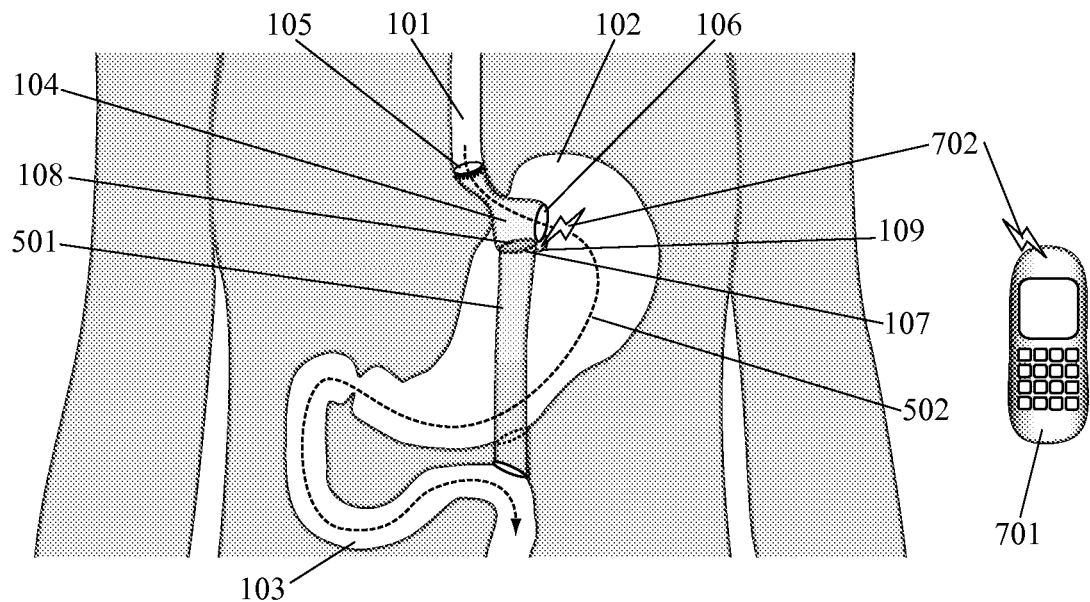
Figure 8:
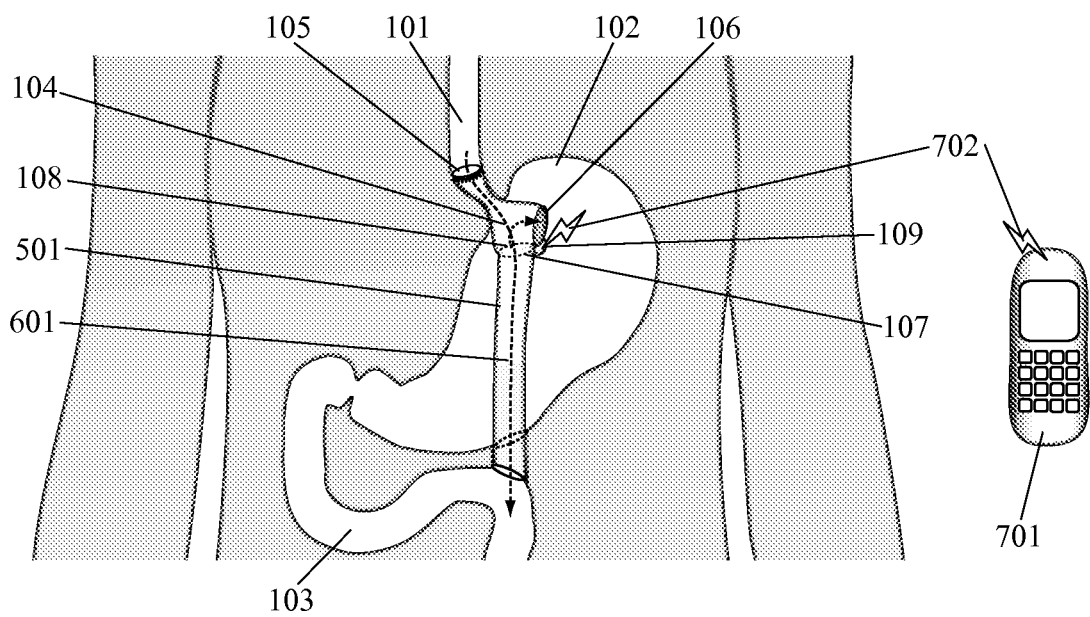

FIGS. 7 and 8 show an example of how this invention can include a flow-control member that can be adjusted in a non-invasive manner by wireless communication with an external control device. In FIG. 7, an external control device 701 is shown communicating wirelessly with valve actuator 109 to position flap valve 108 over second opening 107. This directs the flow of food 502 through first opening 106 for normal absorption of nutrients from food. In FIG. 7, the wireless signal transmission from external control device 701 to valve actuator 109 is symbolically represented by "lightning bolt" symbols 702.

In FIG. 8, external control device 701 is again shown communicating wirelessly with valve actuator 109, but this time to move flap valve 108 over first opening 106. This directs the flow of food 601 through second opening 106 for reduced absorption of nutrients from food. In FIG. 8, the wireless signal transmission from external control device 701 to valve actuator 109 is again symbolically represented by "lightning bolt" symbols 702.

Figure 9:
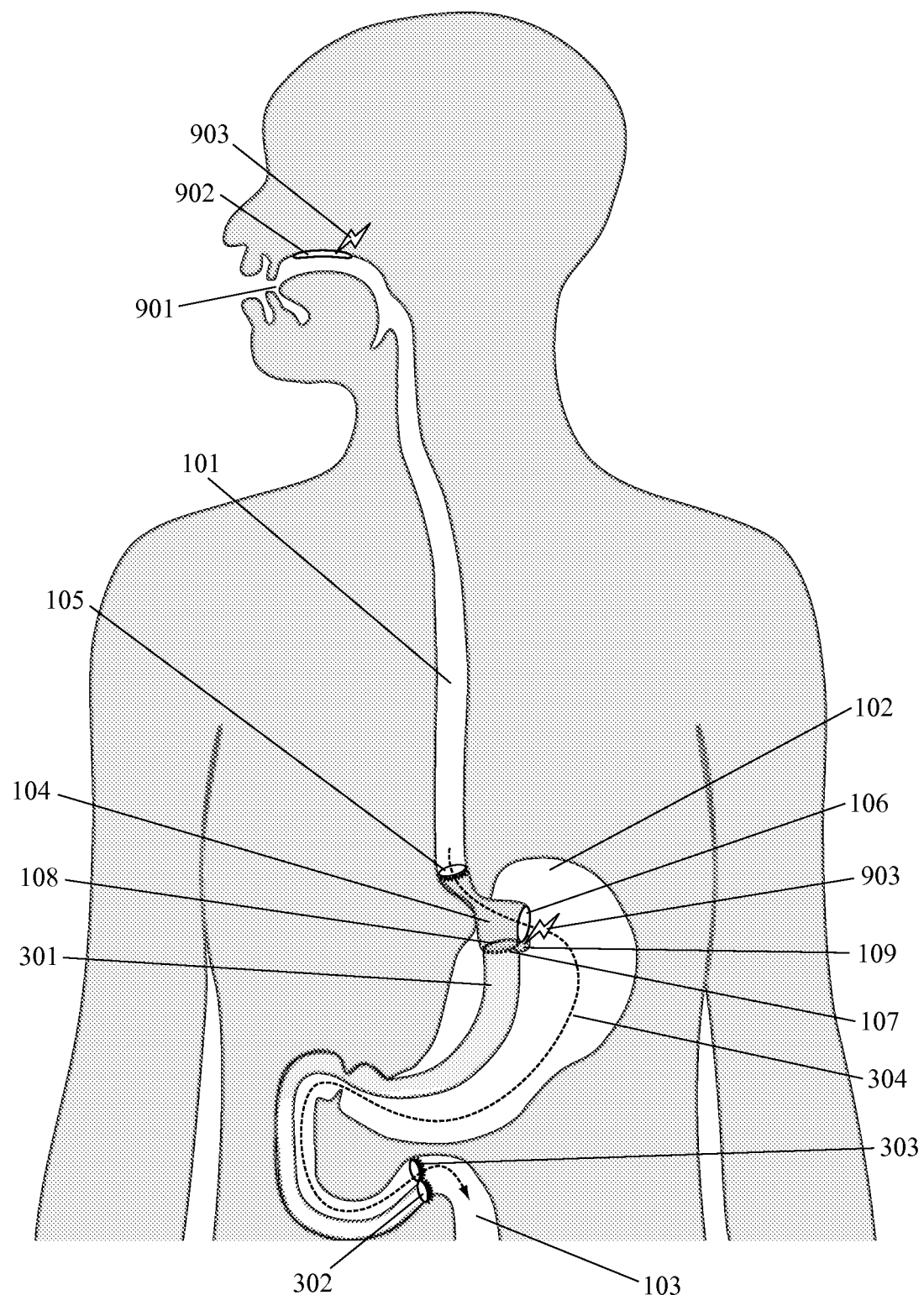
Figure 10:
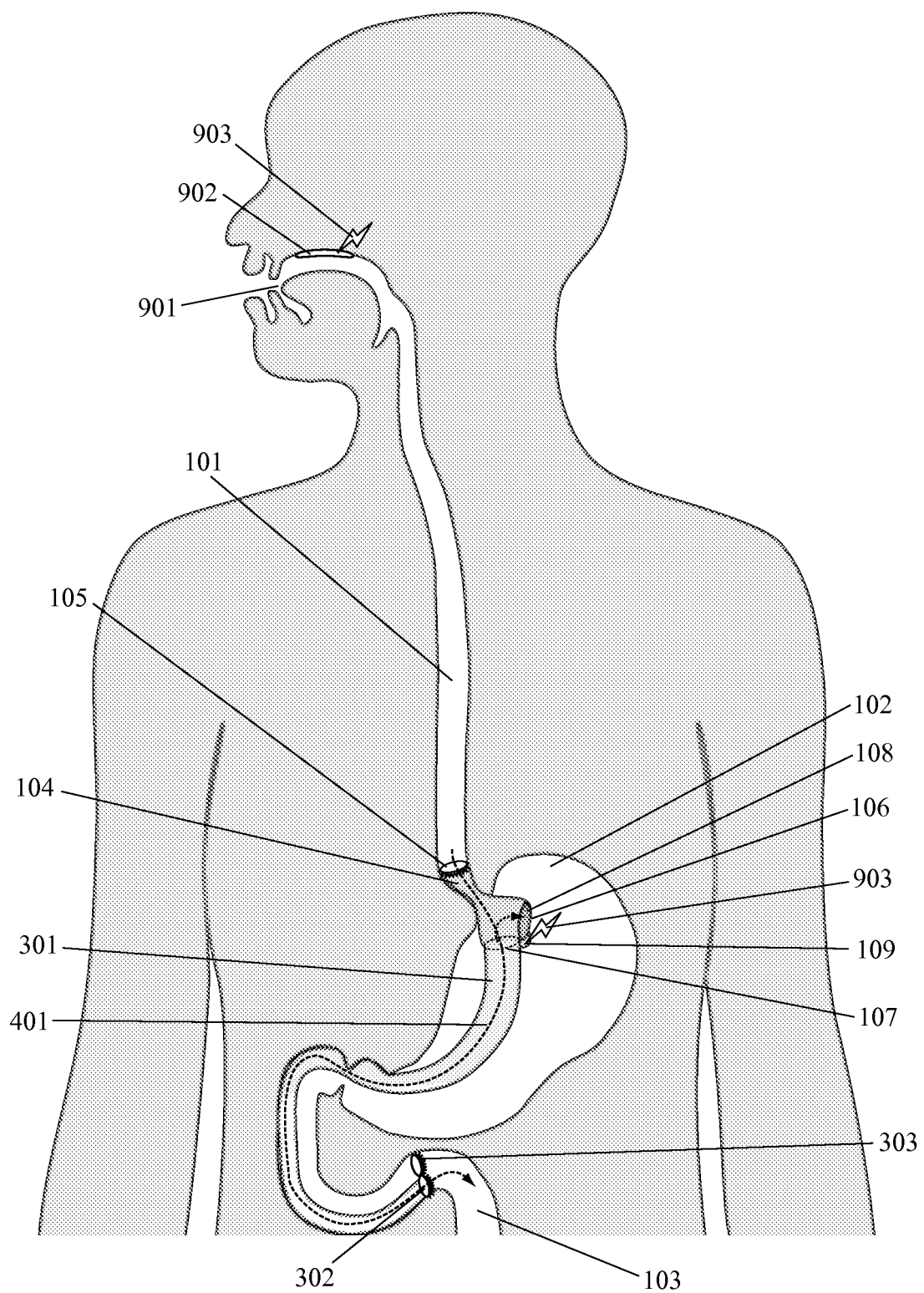

FIGS. 9 and 10 show two sequential views of an embodiment of this invention in which a flow-control member automatically adjusts the types and/or amounts of food that pass through a first normal-absorption food-flow route vs. a second reduced-absorption food-flow route. In this embodiment, flow-control member 104 automatically adjusts the types and/or amounts of food that pass through the first vs. second routes based on information from a food-consumption sensor 902 that is in fluid communication with the person's oral cavity 901.

In an example, food-consumption sensor 902 can selectively detect consumption of unhealthy types and/or amounts of food as food is starting to be digested in the person's mouth. In an example, flow-control member 104 can use information from food-consumption sensor 902 in order to selectively divert unhealthy food through the second food-flow route for lower nutrient absorption, but still allow normal absorption of nutrients from healthy food. This can encourage the person to consume healthy food. This can also enable the person to lose weight in a healthy manner, without the nutritional deficiencies that can accompany food-blind bariatric procedures and devices in the prior art that blindly reduce absorption of nutrients from both healthy and unhealthy food.

FIGS. 9 and 10 show a longitudinal cross-sectional view of the entire upper portion of a person's body. In addition to a flow-control member and Adjustable Gastrointestinal Bifurcation (AGB) similar to that shown in FIG. 3, FIG. 9 also shows a mouth-based food-consumption sensor 902 within the person's oral cavity 901. In this example, mouth-based food-consumption sensor 902 is attached to the upper palatal vault of the person's oral cavity. In this example, food-consumption sensor 902 is in wireless communication with valve actuator 109. This wireless communication is symbolically represented by "lightning bolt" symbols 903.

In an example, mouth-based food-consumption sensor 902 can detect consumption of unhealthy food by chemical analysis of the person's saliva. In an example, food-consumption sensor 902 can selectively detect consumption of unhealthy types of foods by identifying that such foods have a high concentration and/or amount of selected nutrients that are classified as unhealthy.

In an example, food-consumption sensor 902 can selectively detect consumption of unhealthy food based on their having a high concentration, or large amount, of nutrients selected from the group consisting of: sugars, simple sugars, simple carbohydrates, fats, saturated fats, fat cholesterol, and sodium. In various examples, food-consumption sensor 902 can selectively detect consumption and/or digestion of one or more selected types of foods selected from the group consisting of: fried food, high-cholesterol food, high-fat food, high-sugar food, and high-sodium food.

In FIG. 9, food-consumption sensor 902 has not detected consumption of unhealthy food. The information that unhealthy food is not being consumed is wirelessly transmitted from food-consumption sensor 902 to valve actuator 109. As a result, adjustable flap valve 108 covers second opening 107 and food flows through the first food-flow route (the normal gastrointestinal route) for normal nutrient absorption. In FIG. 9, this normal flow for healthy food is shown by dotted-line arrow 304.

In FIG. 10, food-consumption sensor 902 has detected consumption of unhealthy food. The information that unhealthy food is being consumed is wirelessly transmitted from food-consumption sensor 902 to valve actuator 109. As a result, adjustable flap valve 108 covers first opening 106 and food flows through the second food-flow route (a gastrointestinal route with reduced nutrient absorption) for lower nutrient absorption. In FIG. 10, this second food-flow route for unhealthy food is shown by dotted-line arrow 401.

Figure 11:
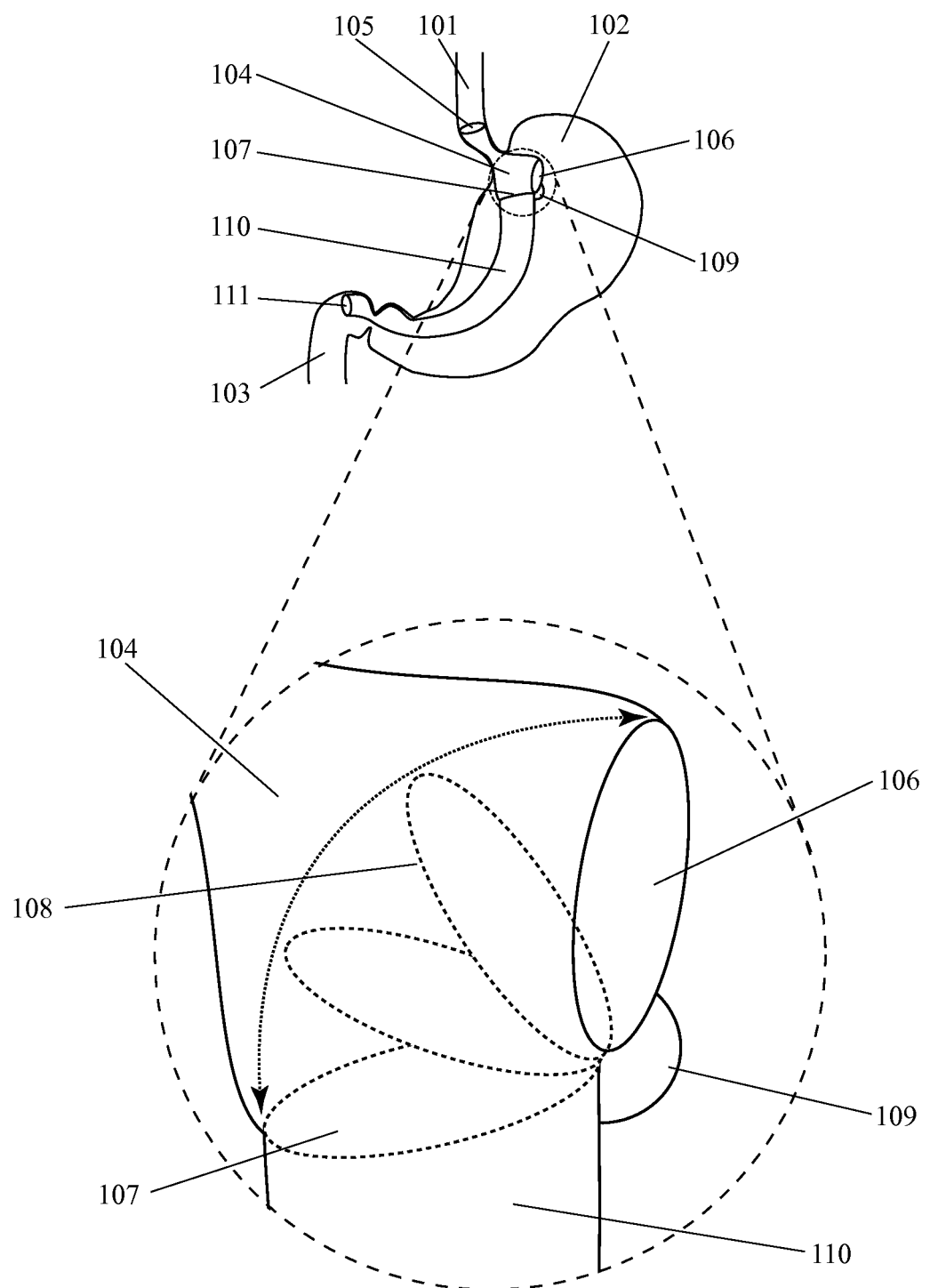

FIG. 11 shows a close-up (enlarged dotted-line circle) view of one example of how flow-control member 104 can be embodied. The top portion of FIG. 11 shows a regular-size view of flow-control member 104 at the intersection of the person's esophagus and stomach, as this flow-control member was introduced in previous figures. The bottom portion of FIG. 11 shows a close-up (enlarged) view of this flow-control member 104 within a dotted-line circle. The bottom portion of FIG. 11 shows flow-control member 104 comprising: first opening 106; second opening 107; adjustable flap valve 108; valve actuator 109; and gastric sleeve 110. The dotted-line ovals in FIG. 11 show, with greater detail, how the flap of the adjustable flap valve 108 can be moved back and forth from a position covering opening 106 to a position covering opening 107 by valve actuator 109.

Figure 12:
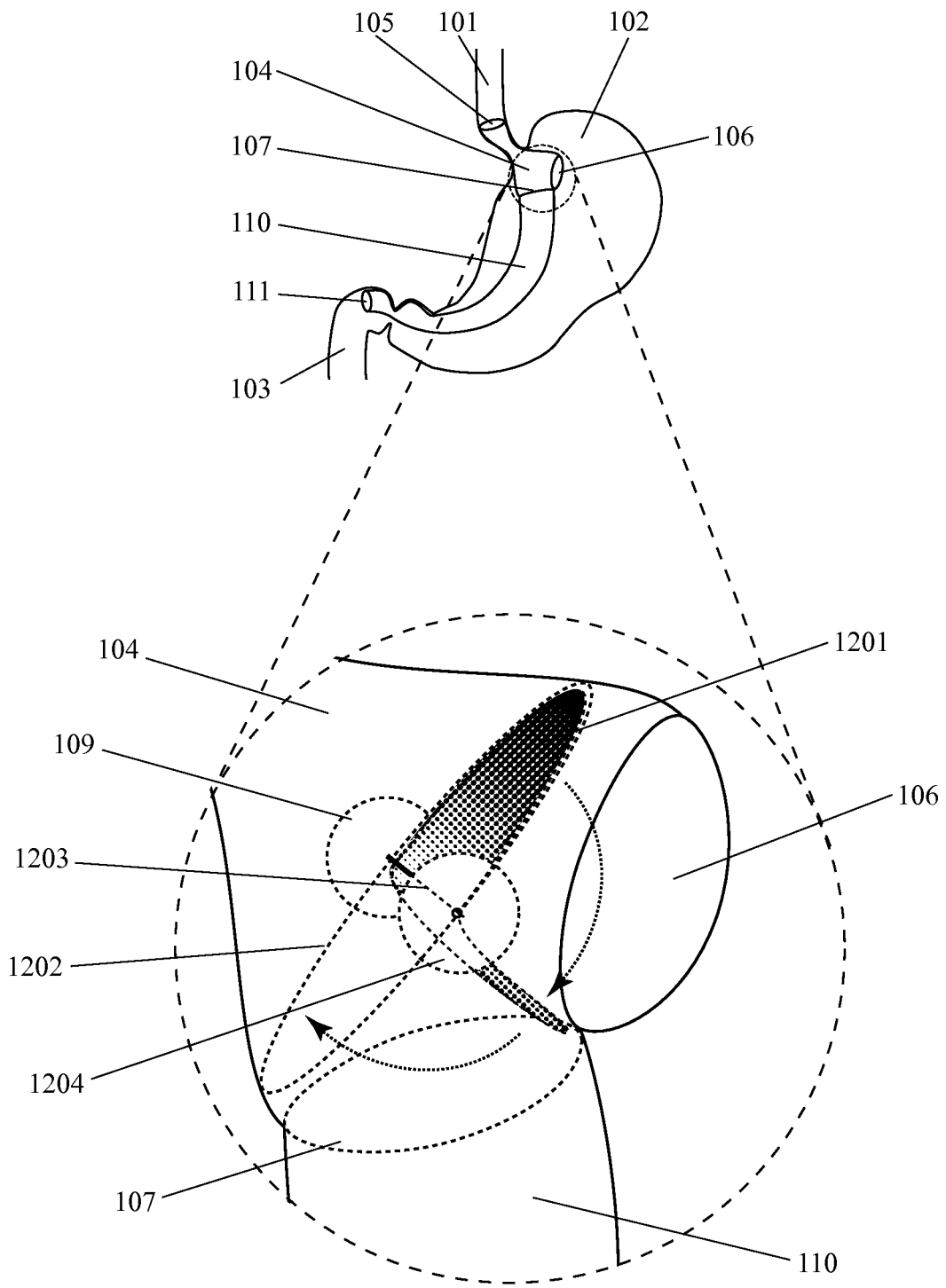

FIG. 12 shows a close-up (enlarged dotted-line circle) view of another example of how flow-control member 104 can be embodied. The top portion of FIG. 12 shows a regular-size view of a flow-control member 104 at the intersection of the person's esophagus and stomach. The bottom portion of FIG. 12 shows a close-up (enlarged) view of this flow-control member 104 within a dotted-line circle.

The bottom portion of FIG. 12 shows this example of flow-control member 104 as comprising: first opening 106; second opening 107; gastric sleeve 110; 90-degree angle bent-disk flap 1201; pre-bifurcation opening 1202; bent-disk flap axle 1203; axle washer 1204; and flap-moving actuator 109. In FIG. 12, 90-degree angle bent-disk flap 1201 is shown in a position that blocks food from entering opening 106 and directs food through opening 107. The dotted-line arrows in FIG. 12 show how 90-degree angle bent-disk flap 1201 can be rotated around axle 1203 by flap-moving actuator 109 in order to alternatively block food from entering opening 107 and direct food through opening 106.

Figure 13:
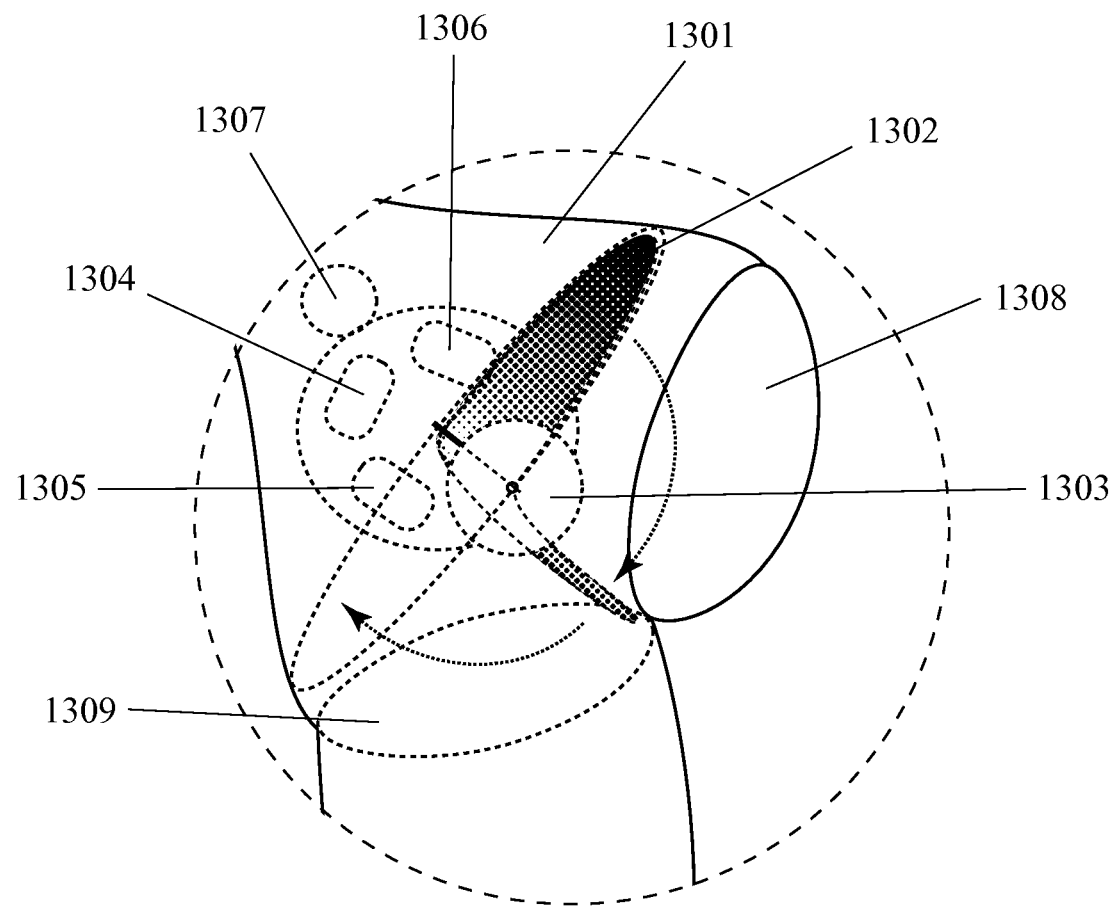

FIG. 13 provides even more details concerning how a flow-control member 104, such as that shown in FIG. 12, can be comprised. In the example shown in FIG. 13, a flow-control member 104 comprises: a bifurcating housing 1301 for the flow-control member; a 90-degree angle bent disk flap valve 1302; a flap-moving actuator 1303; a Central Processing Unit (CPU) 1304; a wireless signal transmitter/receiver 1305; a power source 1306; a food-consumption sensor 1307; first opening 1308; and second opening 1309. In an example, power source 1306, CPU 1304, flap-moving actuator 1303, and wireless signal transmitter/receiver 1305 can all be electrically connected by wires or electronic circuits. Since there are many types of wires and electronic circuitry in the prior art and since the precise pathways for such connections are not central to this invention, these connections are not shown in order to avoid cluttering up the figure.

The detailed embodiments of flow-control members that are shown in FIGS. 11 through 13 are only some of the many ways in which such flow-control members can be embodied. In an example, a flow-control member can comprise a different type of valve to selectively direct food flow between the two alternative food-flow routes. In various examples, a valve in a flow-control member can be selected from the group consisting of: ball valve, balloon valve, biological valve, butterfly valve, check valve, chemical valve, cylinder valve, diaphragm valve, electromechanical valve, flap valve, fluid control valve, helical valve, hydraulic valve, micro valve, Micro Electrical Mechanical System (MEMS) valve, microfluidic valve, organic tissue valve, peristaltic valve, piezoelectric valve, pneumatic valve, pressure regulator valve, and solenoid valve. In various examples, a flow-control member can include one or more components selected from the group consisting of: electronic mechanism, MEMS mechanism, microfluidic mechanism, biochemical mechanism, and biological mechanism.

As shown by the examples in FIGS. 1 through 13, this invention can be embodied in a device which includes a first opening into which food passing through a person's gastrointestinal tract can enter, wherein food that enters this first opening passes through a first food-flow route. In an example, a first food-flow route can be the route which food would naturally travel when passing through a portion of an unmodified gastrointestinal tract and absorption of food passing through the first food-flow route is not reduced. In an example, the first opening and/or the upstream end of a first food-flow route can be located within the person's esophagus or stomach. In an example, a first food-flow route can be an unmodified natural gastrointestinal route comprised of natural tissue. In an example, a first food-flow route can be a modified natural gastrointestinal route comprised of natural tissue.

In an example, this invention can be embodied in a device which also includes a second opening into which food passing through a person's gastrointestinal tract can enter, wherein food that enters this second opening passes through a second food-flow route. In an example, there can be less absorption of nutrients from a bolus of food that passes through this second food-flow route than if the same bolus of food were to pass through the first food-flow route. In an example, there can be less absorption of nutrients from food that passes through the second food-flow route than if the same food were to pass through the first food-flow route.

In an example, a second food-flow route can be generally along the same route which food would naturally travel when passing through a portion of an unmodified gastrointestinal tract, but absorption of food passing through the second food-flow route is reduced because this food flows through a gastrointestinal sleeve or other absorption-reducing device. In an example, food passing through a second food-flow route can pass through a gastrointestinal sleeve, or some other artificial gastrointestinal lumen, with fluid-impermeable walls that reduce absorption of food. In an example, there is less absorption of nutrients from food flowing through the second food-flow route than there would be from that food if that food were to flow through the first food-flow route because food passing through the second food-flow route passes through a gastrointestinal sleeve or other artificial gastrointestinal lumen with walls that reduce absorption of food.

In an example, a second food-flow route can be shorter than a first food-flow route. In an example, a second food-flow route can be a gastric bypass or other gastrointestinal bypass. In an example, food passing through a second food-flow route can bypass a portion of the person's stomach, duodenum, and/or other portion of the intestine. In an example, the second food-flow route can be a gastrointestinal bypass that can bypass a portion of the route which food would naturally travel through an unmodified gastrointestinal tract. In an example, food passing through the second food-flow route can bypass the person's duodenum. In an example, there can be less absorption of nutrients from food flowing through the second food-flow route than there would be from that food if that food were to flow through the first food-flow route because food passing through the second food-flow route bypasses the person's duodenum or some other portion of the person's gastrointestinal tract.

In an example, food passing through a second food-flow route can bypass one or more locations along the person's gastrointestinal tract where digestive enzymes are secreted into the gastrointestinal tract. In an example, there can be less absorption of nutrients from food flowing through a second food-flow route than there would be from that food if that food were to flow through the first food-flow route because the second food-flow route bypasses one or more locations along the person's gastrointestinal tract where digestive enzymes are secreted into the gastrointestinal tract.

In an example, there can be less absorption of nutrients from food flowing through the second food-flow route than there would be from that food if that food were to flow through the first food-flow route because the second food-flow route delivers an absorption-reducing substance into food that passes through it. In an example, this absorption-reducing substance can comprise one or more ingredients that are Generally Recognized As Safe (GRAS) under Sections 201(s) and 409 of the Federal Food, Drug, and Cosmetic Act.

In an example, an absorption-reducing substance can comprise a composition with insoluble fiber. In an example, an absorption-reducing substance can comprise a composition with soluble fiber. In various examples, an absorption-reducing substance can comprise one or more ingredients that are selected from the group consisting of: psyllium, cellulose, avocado oil, castor oil, chitin, chitosan, beta-glucan, coconut oil, corn oil, flaxseed oil, olive oil, palm oil, safflower oil, soy oil, sunflower oil, gelatin, pectin, agar, guar gum, gum acacia, lignin, xantham gum, other insoluble fiber, other soluble fiber, other gum, and other vegetable oil. In an example, the flow of food passing through the second food-flow route is accelerated so that there is less time for nutrient absorption.

In an example, a second opening and/or an upstream end of a second food-flow route can be located within a person's esophagus or stomach. In an example, the downstream end of a second food-flow route can be located within the person's stomach or intestine. In an example, a second food-flow route can be comprised of natural tissue. In an example, a second food-flow route can be an artificial lumen.

In an example, this invention can be embodied in a device and method comprising a first food-flow route and a second food-flow route that comprise two branches of an Adjustable Gastrointestinal Bifurcation (AGB). In an example, when an Adjustable Gastrointestinal Bifurcation (AGB) is created, the first food-flow route forms a first branch from this bifurcation and the second food-flow route forms a second branch from this bifurcation. In an example, the first food-flow route and the second food-flow route can reconverge at a downstream location in the person's gastrointestinal tract. In an example, the upstream ends of a first food-flow route and a second food-flow route can form a bifurcation of the person's gastrointestinal tract and the downstream ends of the first food-flow route and the second food-flow route can reconverge at a downstream location in the person's gastrointestinal tract.

In an example, this invention can be embodied in a device which also includes an implanted flow-control member that can be used to post-operatively and reversibly adjust the types and/or amounts of food that are sent into the first opening (to pass through the first food-flow route) versus the types and/or amounts of food that are sent into the second opening (to pass through the second food-flow route). In an example, this device and method can include a flow-control member that controls types and/or amounts of food passing through the person's gastrointestinal tract that are directed into a first opening (to pass through a first food-flow route) versus the types and/or amounts of food passing through the person's gastrointestinal tract that are directed into a second opening (in order to pass through a second food-flow route).

In a preferred example, a flow-control member can be implanted within a person's gastrointestinal tract. In an example, this flow-control member can be in fluid communication with first and second food-flow routes. In an example, this flow-control member can enable minimally-invasive or non-invasive adjustment of the types and/or amounts of food which go through each of these food-flow routes. In an example, this flow-control member enables wireless adjustment, using an external control unit, of the types and/or amounts of food which go through each of these food-flow routes. In an example, a flow-control member can be used in a minimally-invasive or non-invasive manner in order to selectively and reversibly adjust the types and/or amounts of food that flow into the first food-flow route versus the second food-flow route.

In an inclusive example, a flow-control member can include: (a) an adjustable valve that directs how much food flows through a first food-flow route versus a second food-flow route; (b) an actuator that moves the adjustable valve; (c) a central processing unit that controls the actuator and can communicate wirelessly with external computing devices; (d) a wireless signal receiver/transmitter; (e) a power source; and (f) a food-consumption sensor to monitor and measure the types and/or amounts of food consumed. In an example, a food-consumption sensor can be separate from the flow-control member and in wireless communication with the flow-control member.

In an example, a flow-control member can include a valve to selectively direct food flow between the two alternative food-flow routes. In various examples, a valve in a flow-control member can be selected from the group consisting of: ball valve, balloon valve, biological valve, butterfly valve, check valve, chemical valve, cylinder valve, diaphragm valve, electromechanical valve, flap valve, fluid control valve, helical valve, hydraulic valve, micro valve, Micro Electrical Mechanical System (MEMS) valve, microfluidic valve, organic tissue valve, peristaltic valve, piezoelectric valve, pneumatic valve, pressure regulator valve, and solenoid valve. In various examples, a flow-control member can include one or more components selected from the group consisting of: electronic mechanism, MEMS mechanism, microfluidic mechanism, biochemical mechanism, and biological mechanism.

In an example, a flow-control member can include electronic components. In an example, a flow-control member can have one or more microchips or CPUs. In an example, a flow-control member can include a memory that tracks the cumulative amounts of selected nutrients that a person consumes during an episode of eating or during a selected period of time. For example, a flow-control member may count how many units of sugar, fat, or sodium are consumed by a person during the course of a meal or a day.

In an example, a flow-control member can include a wireless signal transmitter and receiver. In an example, a flow-control member can communicate wirelessly with a food-consumption sensor that is implanted in a different part of a person's body. In an example, a flow-control member can communicate wirelessly with a source that is external to the person's body. In an example, a flow-control member can communicate wirelessly with one or more external computers that are linked by a network.

In an example, a flow-control member can communicate wirelessly with a remote control unit that is external to the person's body. In an example, a flow-control member can be programmed, or otherwise adjusted, by an external remote control unit. In an example, a flow-control member can be wirelessly programmed, or otherwise adjusted, by the person in whom the device is implanted. In an example, a flow-control member can be wirelessly programmed, or otherwise adjusted, by an informal care giver or a health care professional.

In various examples, a flow-control member can have wireless communication with one or more of the following members: a food-consumption sensor that is implanted within, or attached to, a different area of the person's body; a remote computer, network, or control unit that is external to the person's body; and an external mobile, cellular, or tabular electronic communication device. In an example, a flow-control member can be adjusted and/or programmed to change the types and/or amounts of selected foods or nutrients to which it responds by diverting food flow through a lower-absorption second food-flow route. In an example, a flow-control member can include electronics that can be wirelessly programmed in order to change the types and/or quantities of selected foods or nutrients for which food flow is directed into the second food-flow route.

In an example, a flow-control member (or sub-components within such a member) can be adjusted and/or programmed to change one or more of the following aspects of its operation: the amounts of food which are sent through the first versus second food-flow routes; the types of food which are sent through the first versus second food-flow routes; the time of day, day of the week, or other timing parameter wherein food is sent through the first versus second food-flow routes (such as to reduce nutrient consumption from night-time binging or between-meal snacking); the effect of the person's caloric expenditure on how food is sent through the first versus second food-flow routes (to reward exercise and achieve energy balance); the effect of the person's past food consumption on how food is sent through the first versus second food-flow routes; the effect of the person's physical location as measured by GPS (to discourage eating in locations that are associated with unhealthy food consumption); the effect of special social events and holidays (to allow temporary relaxation of dietary restrictions); the effect of a personalized diet plan (created by a health care professional) on how food is sent through the first versus second food-flow routes; and the effect of social networking connections and support groups (to provide peer support for willpower enhancement).

In an example, there can be a list in the device's memory of selected foods or nutrients which will trigger the diversion of food into a second food-flow route. In an example, a flow-control member can be programmed to change this list. In an example, the types of foods can be changed by programming. In an example, the quantities of foods can be changed by programming. In an example, the types and/or quantities of foods on the list can be automatically changed by a device with automatic learning capability.

In various examples, a flow-control member can be powered by an internal power source, by external power source, or by a combination of internal and external power sources. In an example, a power source can be a rechargeable battery or microchip. In an example, a flow-control member (or a power source within such a member) can transduce kinetic, thermal, or biochemical energy from within the person's body. In an example, a flow-control member may be powered by transducing the kinetic energy of stomach movement.

In various examples, a flow-control member can be powered from one or more energy sources selected from the group consisting of: a battery, an energy-storing chip, energy harvested or transduced from a bioelectrical cell, energy harvested or transduced from an electromagnetic field, energy harvested or transduced from an implanted biological source, energy harvested or transduced from blood flow or other internal fluid flow, energy harvested or transduced from body kinetic energy, energy harvested or transduced from glucose metabolism, energy harvested or transduced from muscle activity, energy harvested or transduced from organ motion, and energy harvested or transduced from thermal energy.

In various examples, a flow-control member (or sub-components within a flow-control member) can be can be made from one or more materials selected from the group consisting of: cobalt-chromium alloy, fluoropolymer, latex, liquid-crystal polymer, nylon, perfluoroethylene, platinum, polycarbonate, polyester, polyethylene, polyolefin, polypropylene, polystyrene, polytetrafluoroethylene (PTFE), polyurethane, polyvinyl chloride, pyrolytic carbon, silicon, silicone rubber, silicone, stainless steel, tantalum, titanium, and urethane.

In an example, a flow-control member can use information received from a food-consumption sensor to adjust the types and/or amounts of food that it directs through a first normal-absorption, food-flow route versus the types and/or amounts of food that it directs through a second reduced-absorption, food-flow route. In an example, a food-consumption sensor can provide information about the types and/or amounts of food that the person is consuming and/or digesting. In an example, such a food-consumption sensor can be a sub-component of a flow-control member. In another example, such a food-consumption sensor can be located elsewhere and in wireless communication with the flow-control member.

In various examples, a food-consumption sensor can be selected from the group consisting of: accelerometer, amino acid sensor, biochemical sensor, biological sensor, camera, chemical sensor, chemoreceptor, cholesterol sensor, chromatography sensor, EGG sensor, electrogastrogram sensor, electrolyte sensor, electromagnetic sensor, electronic nose, EMG sensor, enzymatic sensor, enzyme-based sensor, fat sensor, flow sensor, genetic sensor, genetic sensor, glucose sensor, imaging sensor, impedance sensor, infrared sensor, interferometer, medichip, membrane-based sensor, Micro Electrical Mechanical System (MEMS) sensor, microfluidic sensor, micronutrient sensor, molecular sensor, motion sensor, muscle activity sensor, nanoparticle sensor, neural impulse sensor, nutrient sensor, optical sensor, osmolality sensor, particle size sensor, pattern recognition sensor, peristalsis sensor, pH level sensor, pressure sensor, protein-based sensor, reagent-based sensor, smell sensor, sound sensor, strain gauge, taste sensor, and temperature sensor.

In an example, a food-consumption sensor can selectively detect consumption and/or digestion of selected types of food or nutrients. In an example, a food-consumption sensor that can discriminate between consumption of unhealthy types of food versus consumption of healthy types of food. In an example, a food-consumption sensor can selectively discriminate between digestion of unhealthy food and digestion of healthy food. In an example, a food-consumption sensor can selectively discriminate between consumption of unhealthy quantities of food versus healthy quantities of food.

In an example, a food-consumption sensor can selectively detect consumption and/or digestion of unhealthy types of foods by identifying that such foods have a high concentration and/or amount of selected nutrients that are classified as unhealthy. In an example, a food-consumption sensor can selectively detect consumption of unhealthy food based on their having a high concentration, or large amount, of nutrients selected from the group consisting of: sugars, simple sugars, simple carbohydrates, fats, saturated fats, fat cholesterol, and sodium. In various examples, a food-consumption sensor can selectively detect consumption and/or digestion of one or more selected types of foods selected from the group consisting of: fried food, high-cholesterol food, high-fat food, high-sugar food, and high-sodium food.

In an example, unhealthy types of food can be identified by a food-consumption sensor based on food having one or more nutritional quantities selected from the group consisting of: at least a selected number of grams of fats per suggested serving, at least a selected number of grams of saturated fats per suggested serving, at least a selected number of milligrams of fat cholesterol per suggested serving, at least a selected number of grams of carbohydrates per suggested serving, and/or at least a selected number of milligrams of sodium per suggested serving.

In an example, unhealthy types of food can be identified by a food-consumption sensor based on food exceeding one or more nutritional percentages selected from the group consisting of: a selected percentage of the recommended daily intake of fat per suggested serving, a selected percentage of the recommended daily intake of saturated fat per suggested serving, a selected percentage of the recommended daily intake of fat cholesterol per suggested serving, a selected percentage of the recommended daily intake of carbohydrate per suggested serving, and/or a selected percentage of the recommended daily intake of sodium per suggested serving.

In an example, a food-consumption sensor can enable selective detection of cumulative consumption of food during a period of time that totals: at least a selected number of grams of fats, at least a selected number of grams of saturated fats, at least a selected number of milligrams of fat cholesterol, at least a selected number of grams of carbohydrates, and/or at least a selected number of milligrams of sodium. In an example, a food-consumption sensor can enable selective detection of cumulative consumption of food during a period of time that totals: at least a predetermined amount of fat, at least a predetermined amount of saturated fat, at least a predetermined amount of fat cholesterol, at least a predetermined amount of carbohydrates, and/or at least a predetermined amount of sodium. In an example, quantities of food exceeding one or more of these amounts can be automatically classified as unhealthy.

In an example, there can be a predefined list of types of food which are classified as unhealthy. In an example, there can be predefined quantities of selected types of food which are classified as unhealthy. In an example, there can be a predefined list of types of food which are classified as healthy. In an example, there can be predefined quantities of selected types of food which are classified as healthy. In an example, lists of the types and quantities of food which are classified as unhealthy or healthy can be compiled and adjusted by experts and professionals who provide the person with nutritional and dietary counseling.

In an example, healthy types of food can be identified in a negative manner, as any type of food that is not identified as being unhealthy. In an alternative example, healthy food can be identified in a positive manner, as food with a large concentration or amount of one or more nutrients selected from the group consisting of: food with a lot of soluble fiber, food with a lot of insoluble fiber, food with a lot of essential vitamins, and food with a high concentration of essential nutrients that the person's diet generally lacks.

In an example, a food-consumption sensor can selectively detect and measure cumulative consumption and/or digestion of selected amounts of food or nutrients. In an example, a food-consumption sensor, either alone or in combination with a remotely-located central processing unit with which the sensor is in wireless communication, can discriminate between cumulative consumption of an unhealthy amount of food versus a healthy amount of food.

In an example, a flow-control member can direct a healthy amount of food to flow through a normal-absorption first food-flow route and can direct excess consumed food (over the healthy amount) to flow through a reduced-absorption second food-flow route. In an example, a flow-control member can track and record cumulative food consumption during a period of time or during an eating episode based on information received from a food-consumption sensor. In an example, an eating episode can be defined as a period of time with continuous eating. In an example, an eating episode can be defined as a period of time with less than a selected amount of time between mouthfuls and/or swallows.

In an example, a flow-control member can receive information from a food-consumption sensor that is implanted within a person's body. In various examples, a food-consumption sensor can be attached to, or implanted within, the person's body by one or more means selected from the group consisting of: suture, staple, adhesive, glue, clamp, clip, pin, snap, elastic member, tissue pouch, fibrotic tissue, screw, and tissue anchor. In an example, a food-consumption sensor can be configured to be implanted within, or attached to, one of the following locations within a person's body: the person's mouth, soft palate, tongue, teeth, and/or oral cavity; the person's nose or nasal cavity; and the person's esophagus, stomach, or intestine. In various examples, a food-consumption sensor can be located in any location from which it is in fluid and/or gaseous communication with food that the person is consuming or digesting.

In an example, a food-consumption sensor can be configured to be attached to, or implanted within, a person's stomach. In an example, a food-consumption sensor can detect digestion of selected types of food within a person's stomach. In another example, a food-consumption sensor can be configured to be attached to, or implanted within, a person's intestine. In an example, a food-consumption sensor can detect digestion of selected types of food within a person's intestine. In various examples, an implanted food-consumption sensor can be configured to be attached to, or implanted within, a person's stomach, duodenum, jejunum, ileum, caecum, colon, or esophagus. In various examples, a food-consumption sensor can be configured to be implanted within a person's abdominal cavity with a means of fluid, neural, or other communication with the person's stomach, duodenum, jejunum, ileum, caecum, colon, or esophagus.

In an example, a food-consumption sensor can be configured to be implanted or attached within a person's mouth. In an example, a food-consumption sensor can be implanted within a person's mouth and in wireless communication with a flow-control member. In an example, food identification by such a sensor can occur as food is entering, or being consumed within, a person's mouth. In an example, a food-consumption sensor can be configured to be attached to, or implanted within, a person's oral cavity, nasal cavity, or tissue surrounding one of these cavities.

In an example, a flow-control member can receive information from a food-consumption sensor that is configured to be located in one of the following locations within the person's body: implanted within the person's mouth or oral cavity; attached or implanted with the person's soft palate; attached or implanted within the person's teeth; attached to or implanted within the person's tongue. In various examples, such a sensor can be configured to be attached to, or implanted within, the person's hard palate, palatal vault and/or upper mouth roof, teeth, tongue, or soft palate. In an example, such a food-consumption sensor can detect consumption or digestion of selected types or amounts of food within the person's mouth.

In an example, a food-consumption sensor can be configured to be attached to, implanted within, or attached underneath a person's tongue. In an example, a food-consumption sensor can be inserted into a person's tongue. In an example, a food-consumption sensor can be attached or implanted sublingually. In an example, a food-consumption sensor can be configured to be attached to, or inserted into, the soft palate tissues at the rear of a person's oral cavity.

In an example, a food-consumption sensor can be configured to be attached to, or implanted within, a person's teeth. In various examples, a food-consumption sensor can be attached to the lingual, palatal, buccal, and/or labial surfaces of a person's teeth. In an example, a food-consumption sensor can be incorporated into a dental and/or orthodontic appliance. In an example, a food-consumption sensor can be incorporated into a dental bridge, cap, or crown.

In an example, a food-consumption sensor can be a chemical sensor that uses chemical analysis to identify particular types of food and/or nutrients. In an example, a food-consumption sensor can analyze the chemical composition of a person's saliva in order to automatically and selectively detect when a person is digesting a food that is high in (simple) sugar or (saturated) fat. In an example, a food-consumption sensor can perform intra-oral analysis of saliva in order to differentiate between consumption of unhealthy food versus healthy food. In various examples, a chemical sensor can detect the amount or concentration of sugars, simple carbohydrates, fats, saturated fats, cholesterol fat, and/or sodium in food as food is being digested within a person's mouth.

In an example, a food-consumption sensor can identify the type of food as it is being consumed, and beginning to be digested, within a person's mouth. In an example, a food-consumption sensor that is in fluid communication with a person's mouth can identify food as being unhealthy using one or more methods selected from the group consisting of: chemical analysis of food as it begins to be digested within a person's mouth; olfactory analysis of food as it beings to be digested within a person's mouth; image analysis of images of food as it approaches the person's mouth; sonic analysis of chewing or swallowing as food is consumed; and analysis of signals from nerves that innervate the person's taste buds and/or olfactory receptors.

There are advantages to having a food-consumption sensor be implanted within, attached to, and/or in fluid communication with a person's oral cavity and/or nasal cavity. A food-consumption sensor that is located in this "upstream location" within the person's gastrointestinal tract can detect consumption and/or digestion of unhealthy food earlier than an intragastric sensor. A sensor in a person's mouth can detect such food at the point of initial consumption, just as it is starting to be digested. In this manner, a mouth-based food-consumption sensor can provide "advance notice" that a bolus of unhealthy food (or an excessive amount of food) will be coming down the esophagus to enter the stomach. Such "advance notice" can provide more time for activation of an intragastric valve (or other flow-directing component of a flow-control member) to selectively divert that unhealthy bolus of food through a second, lower-absorption food-flow route.

Compared to an intragastric food sensor, a mouth-based or nose-based food-consumption sensor can provide more time for modification of the stomach or intestine to reduce absorption of nutrients from a selected bolus of food. In an example, "advance notice" from a mouth-based or nose-based food-consumption sensor can provide more lead time for adjustment of food flow through an Adjustable Gastrointestinal Bifurcation (AGB) so that unhealthy food is selectively diverted through a lower-absorption second food-flow route.

There are other alternative locations for placement of a food-consumption sensor. In an example, a food-consumption sensor can be configured to be implanted in a subcutaneous site or in an intraperitoneal site. In an example, a food-consumption sensor can be configured to be attached to a nerve that is connected to the stomach. In another example, a food-consumption sensor can be configured to be implanted in adipose tissue or in muscular tissue.

There are advantages to having a food-consumption sensor be implanted somewhere within a person's body. As compared to an external and/or mobile food-consumption sensor, an implanted food-consumption sensor can be: more consistent and automatic its food consumption monitoring function; less prone to compliance problems or circumvention on the part of the person whose food consumption is being monitored; and less dependent on voluntary action by the person being monitored. Also, an implanted food-consumption monitor can provide types of information concerning food consumption based on direct fluid communication with food (such as chemical interaction) which are not available from external devices (such as cameras, motion sensors, and sound sensors) that do not come into direct fluid communication with food.

Although there can be advantages to using an implanted food-consumption sensor as compared to an external food-consumption sensor, there are also some respects in which an external food-consumption sensor can be superior to an implanted one. As an example of an advantage of an external food-consumption sensor, an external food-consumption sensor can be less invasive and less-costly than an implanted sensor. As another advantage, an external sensor may be able to detect food-consumption even earlier than a mouth-based or nose-based sensor. In an example, an external sensor can detect pending food consumption even as a person reaches for food, brings it up to their mouth, or inserts it into their mouth. As another potential advantage of an external sensor, some types of food identification are easier when performed before food is inserted into the person's mouth. For example, image-based analysis to determine of food type is generally easier when food is on a plate than when it is being chewed within a person's mouth.

For these reasons, in an example, this invention can include an external (wearable, portable, or and/mobile) food-consumption sensor that sends information (in a wireless manner) to an internal (intragastric) flow-control member. In an example, a flow-control member can wirelessly communicate with a food-consumption sensor that is carried by, or worn by, a person. In an example, a food-consumption sensor can be incorporated into a mobile electronic device, such as a cell phone, mobile phone, or electronic tablet that is carried by the person. In an example, an external sensor can be in wireless communication with an implanted member that selectively modifies consumption of a given bolus of food in order to reduce absorption of unhealthy food and to allow normal absorption of healthy food. In an example, an external sensor, or a mobile device of which this sensor is an application or component, can communicate with the internet and/or other mobile devices.

In an example, a person can wear a food-consumption sensor. In various examples, a person can wear a food-consumption sensor on their wrist, hand, finger, arm, torso, neck, head, and/or ear. In an example, a food-consumption sensor can be part of a piece of electronically-functional jewelry. In an example, an external sensor, or piece of electronically-functional jewelry of which this sensor is a part, can communicate with the internet and/or other people via other electronic communication means. In an example, an external food-consumption sensor can be incorporated into one or more of the following wearable members: wrist watch, bluetooth device, bracelet, arm band, button, earring, eyeglasses, finger ring, headphones, hearing aid, necklace, nose ring, and pendant.

In an example, this invention can be embodied in a device and method that uses an Adjustable Gastrointestinal Bifurcation (AGB) to selectively reduce absorption of unhealthy types and/or amounts of food. In an example, this invention can be embodied in a device and method that can selectively reduce absorption of nutrients from unhealthy food, but not reduce absorption of nutrients from healthy food. In an example, this device and method can selectively and automatically reducing absorption of nutrients from unhealthy food in a person's gastrointestinal tract by diverting unhealthy food through the lower-absorption branch of an Adjustable Gastrointestinal Bifurcation (AGB).

Selective malabsorption of unhealthy food, while allowing normal absorption of healthy food, can help a person to lose weight without suffering the deficiencies of essential nutrients that can occur with food-blind bariatric procedures and malabsorption devices in the prior art. This is a significant improvement over food-blind procedures and devices in the prior art that cause relatively-permanent and indiscriminant malabsorption of all types of food.

In an example, this invention can be embodied in a device to selectively reduce absorption of unhealthy food and allow normal absorption of healthy food. In an example, this discriminatory ability can be adjusted or programmed to change the types and/or quantities of food which are classified as unhealthy versus healthy. Such a device and method with food discrimination capability can be superior to bariatric surgery and malabsorption devices in the prior art that are blind to whether a selected bolus of food traveling through the gastrointestinal tract is healthy or unhealthy. This device and method can avoid the deficiencies concerning essential nutrients that can occur with food-blind malabsorption devices and methods in the prior art. In an example, this device can be a key part of an overall system to ensure that a person still gets proper nutrition, even while losing weight.

In an example, this invention can be embodied in a device and method that uses information from a food-consumption sensor to automatically send healthy types and/or amounts of food into a first food-flow route and automatically send unhealthy types and/or amounts of food into a second food-flow route. In an example, a device and method can selectively, temporarily, and automatically divert foods into a second lower-absorption food-flow route within a person's gastrointestinal tract in response to consumption of unhealthy types or amounts of food. In an example, a device and method that can automatically divert unhealthy types or excess amounts of food through a lower-absorption second food-flow route in a person's gastrointestinal tract.

In an example, a device can be programmed to allow unmodified absorption of nutrients from selected foods for a limited time period or up to a certain amount. In an example, a device and method can allow up to a certain amount of one or more selected types of food or nutrients to be consumed by a person before food is diverted into a second lower-absorption food-flow route. In an example, a device can be programmed to allow moderate consumption of some foods without diverting food into a second food-flow route, but can divert food if there is excessive consumption of those foods. In an example, a device and method can selectively direct food passing through the person's gastrointestinal tract into a gastric bypass when the person is consuming unhealthy types and/or amounts of food.

In an example, a device and method can use information from a food-consumption sensor to automatically send (up to) a selected amount of food consumed during a given time period or episode of eating through a first (relatively-higher absorption) food-flow route and to automatically send amounts of food consumed over that selected amount during that time period or episode of eating through a second (relatively-lower absorption) food-flow route.

In an example, a device can start diverting food into a second food-flow route when a food-consumption sensor detects that the person has begun consuming unhealthy food and can stop diverting food into the second food-flow route when the sensor detects that the person has begun consuming healthy food. In an example, a device can automatically stop diverting food into a second food-flow route when a food-consumption sensor identifies that a person is consuming or digesting healthy food.

In an example, this invention can be embodied in a device for selectively reducing nutrient absorption from selected types and/or amounts of food using an Adjustable Gastrointestinal Bifurcation (AGB) comprising: (a) a first opening into which food passing through a person's gastrointestinal tract can enter, wherein food that enters this first opening passes through a first food-flow route; (b) a second opening into which food passing through a person's gastrointestinal tract can enter, wherein food that enters this second opening passes through a second food-flow route, and wherein there is less absorption of nutrients from food that passes through the second food-flow route than if the same food were to pass through the first food-flow route; and (c) a flow-control member, wherein this flow-control member can post-operatively and reversibly adjust the types and/or amounts of food that are sent into the first opening to pass through the first food-flow route versus the types and/or amounts of food that are sent into the second opening to pass through the second food-flow route, and wherein this flow-control member enables this food flow adjustment to be done in a minimally-invasive or non-invasive manner.

In an example, this invention can be embodied in a device for selectively reducing nutrient absorption from selected types and/or amounts of food using an Adjustable Gastrointestinal Bifurcation (AGB) comprising: (a) a first opening into which food can enter to flow through a first food-flow route through a portion of a person's gastrointestinal tract; (b) a second opening into which food can enter to flow through a second food-flow route through a portion of a person's gastrointestinal tract, wherein there is less absorption of nutrients from food flowing through the second food-flow route than from that food if it were to flow through the first food-flow route; and (c) an implantable flow-control member wherein this flow-control member is configured to be implanted within a person's body, wherein this flow-control member adjusts the types and/or amounts of food that are sent into the first food-flow route versus the types and/or amounts of food that are sent into the second food-flow route, wherein this flow-control member can be adjusted in a minimally-invasive or non-invasive manner.

In an example, this invention can be embodied in a method for selectively reducing absorption of nutrients from selected types and/or amounts of food using Adjustable Gastrointestinal Bifurcation (AGB) comprising: (a) creating a first opening into which food passing through a person's gastrointestinal tract can enter, wherein food that enters this first opening passes through a first food-flow route; (b) creating a second opening into which food passing through a person's gastrointestinal tract can enter, wherein food that enters this second opening passes through a second food-flow route, wherein there is less absorption of nutrients from food that passes through the second food-flow route than if the same food were to pass through the first food-flow route; and (c) using an implanted flow-control member to post-operatively and reversibly adjust the types and/or amounts of food that are sent into the first opening to pass through the first food-flow route versus the types and/or amounts of food that are sent into the second opening to pass through the second food-flow route, wherein this adjustment is done in a minimally-invasive or non-invasive manner.

In an example, this invention can be embodied in a method for selectively reducing the absorption of unhealthy food comprising: (a) creating a bypass route in a portion of a person's gastrointestinal tract, wherein there is less absorption of nutrients from food flowing through this bypass route than there was absorption of nutrients from food flowing through the original route before the bypass was created, and wherein the possibility of food flowing through the original route is maintained; and (b) implanting a flow-control member in the person's body, wherein this flow-control member directs the flow of selected types and/or quantities of food through the bypass route and directs the flow of other types and/or quantities of food through the original route, wherein the types and/or quantities of food that that flow through the bypass route relative to the types and/or quantities of food that flow through the original route can be post-operatively and reversibly adjusted in a minimally-invasive or non-invasive manner.

In an example, this invention can be embodied in a device for selectively reducing absorption of nutrients from selected types and/or amounts of food using Adjustable Gastrointestinal Bifurcation (AGB) comprising: (a) a first opening into which food passing through a person's gastrointestinal tract can enter, wherein food that enters this first opening passes through a first food-flow route; (b) a second opening into which food passing through a person's gastrointestinal tract can enter, wherein food that enters this second opening passes through a second food-flow route, and wherein there is less absorption of nutrients from food that passes through the second food-flow route than if the same food were to pass through the first food-flow route; (c) a food-consumption sensor; and (d) a flow-control member, wherein this flow-control member is configured to be implanted without the person's body, wherein this flow-control member uses information from the food-consumption sensor to automatically send healthy types and/or amounts of food into the first opening to pass through the first food-flow route and to automatically send unhealthy types and/or amounts of food into the second opening to pass through the second food-flow route.

In an example, this invention can be embodied in a device for selectively reducing nutrient absorption from selected types and/or amounts of food using an Adjustable Gastrointestinal Bifurcation (AGB) comprising: (a) a first opening through which food can enter to flow through a first food-flow route through a portion of a person's gastrointestinal tract; (b) a second opening through which food can enter to flow through a second food-flow route through a portion of a person's gastrointestinal tract, wherein there is less absorption of nutrients from food flowing through the second food-flow route than from that food if it were to flow through the first food-flow route; (c) a food-consumption sensor; and (d) an implantable flow-control member wherein this flow-control member is configured to be implanted within a person's body, wherein this flow-control member adjusts the types and/or amounts of food that are sent into the first food-flow route versus the types and/or amounts of food that are sent into the second food-flow route, wherein this flow-control member uses information from the food-consumption sensor to automatically send healthy types and/or amounts of food through the first food-flow route and send unhealthy types and/or amounts of food through the second food-flow route.

In an example, this invention can be embodied in a device for changing the absorption of nutrients from food using an adjustable gastrointestinal bifurcation comprising: (a) a first opening to a first food-flow route through which food can pass through a portion of the gastrointestinal tract; (b) a second opening to a second food-flow route through which food can pass through a portion of the gastrointestinal tract, wherein there is less absorption of nutrients from food if this food passes through the second food-flow route than if this food passes through the first food-flow route; and (c) a flow-control member that is in fluid communication with the first and second openings, wherein this flow-control member is configured to be implanted within the person's body, wherein the flow-control member automatically sends a healthy type and/ or quantity of food into the first food-flow route for higher absorption of nutrients and sends an unhealthy type and/or quantity of food over that selected amount into the second food-flow route for lower absorption of nutrients.

In an example, this invention can be embodied in a device for selectively and automatically reducing the absorption of unhealthy food by a person's gastrointestinal tract comprising: (a) a food-identifying sensor that selectively detects when the person is consuming and/or digesting unhealthy food, wherein unhealthy food is identified as food that has a relatively large amount or concentration of one or more nutrients selected from the group consisting of: sugars, simple sugars, simple carbohydrates, fats, saturated fats, cholesterol, and sodium; and (b) a flow-control member that is configured to be in fluid communication with a bifurcation in the person's gastrointestinal tract, wherein there is less absorption of nutrients from food passing through this bifurcation into a second food-flow route than there is absorption of nutrients from food passing through this bifurcation into a first food-flow route, and wherein this flow-control member selectively and automatically directs healthy food through the first food-flow route and unhealthy food through the second food-flow route.

In an example, this invention can be embodied in a device for selectively reducing the absorption of unhealthy food comprising: (a) a food consumption sensor that detects the types and/or quantities of food consumed by a person, wherein this sensor is implanted within the person's body; and (b) a gastrointestinal flow-diverting member, wherein this flow-diverting member can automatically, reversibly, and selectively change the types and/or amounts of food that are diverted through a gastrointestinal bypass route versus the types and/or amounts of food that flow through the original gastrointestinal route, where such diversion of food through the bypass route is based on the results of the food consumption sensor, wherein there is less absorption of nutrients from food that passes through the bypass route than food that passes through the original route, and wherein this gastrointestinal flow-diverting member is implanted within the person's body.

In an example, this invention can be embodied in a device for changing the absorption of nutrients from food using an adjustable gastrointestinal bifurcation comprising: (a) a first opening to a first food-flow route through which food can pass through a portion of the gastrointestinal tract; (b) a second opening to a second food-flow route through which food can pass through a portion of the gastrointestinal tract, wherein there is less absorption of nutrients from food if this food passes through the second food-flow route than if this food passes through the first food-flow route; and (c) a flow-control member that is in fluid communication with the first and second openings, wherein this flow-control member is configured to be implanted with the person's body, wherein this flow-control member can post-operatively and reversibly adjust the amount and/or type of food that passes into the first food-flow route versus the second food-flow route, wherein this flow-control member can make these adjustments automatically in response to signals from a food sensor or wherein a person can make these adjustments using the flow-control member in a minimally-invasive or non-invasive manner.

In an example, this invention can be embodied in a method for changing the absorption of nutrients from food using an adjustable gastrointestinal bifurcation comprising: (a) creating a bifurcation within a person's gastrointestinal tract, wherein there is less absorption of nutrients from food passing through a second food-flow route from this bifurcation that there would be from this food passing through a first food-flow route from this bifurcation; and (b) configuring a flow-control member to be implanted within the person's body, wherein this flow-control member is in fluid communication with the first food-flow route and second food-flow route, wherein this flow-control member can post-operatively and reversibly adjust the amount and/or type of food that passes into the first food-flow route versus the second food-flow route, wherein this flow-control member can make these adjustments automatically in response to signals from a food sensor or wherein a person can make these adjustments using the flow-control member in a minimally-invasive or non-invasive manner.

In an example, this invention can be embodied in a method for selectively and automatically reducing the absorption of selected types of food in the gastrointestinal tract comprising: (a) selectively and automatically detecting when a person is consuming or digesting selected types of food by means of a sensor that is configured to be implanted or attached within the person's oral cavity, the person's nasal cavity, or tissue surrounding one of these cavities; and (b) selectively and automatically reducing the absorption of food within the person's gastrointestinal tract by selectively and automatically diverting this selected food through a second food-flow route from a gastrointestinal bifurcation with lower absorption of nutrients from food than a first food-flow route from this gastrointestinal bifurcation.

In an example, this invention can be embodied in a method for selectively reducing absorption of unhealthy food comprising: (a) creating an bypass route for food to flow through a portion of a person's gastrointestinal tract instead of flowing through an original route through a portion of the person's gastrointestinal tract; (b) creating a bifurcation in the person's gastrointestinal tract through which food can be directed to flow through the bypass route or through the original route; and (c) implanting an adjustable flow-directing member, wherein this adjustable flow-directing member can be post-operatively and reversibly adjusted to direct food to flow through either the bypass route or through the original route, and wherein this adjustable flow-control member automatically and selectively directs unhealthy food to flow through the bypass route and healthy food to flow through the original route.

In an example, this invention can be embodied in a method for selectively reducing absorption of unhealthy food comprising: (a) creating a bypass route for a portion of a person's gastrointestinal tract, wherein food can be diverted to flow through this bypass route or be allowed to continue to flow through the original route, and wherein there is less absorption of nutrients from food that passes through the bypass route than food that passes through the original route; and (b) implanting an adjustable flow-diverting member into the person's body, wherein this flow-diverting member can automatically, reversibly, and selectively change the types and/or amounts of food that are diverted to flow through the bypass route versus the types and/or amounts of food that flow through the original route.

In an example, this invention can be embodied in a device for adjustably reducing absorption of nutrients from consumed food using an Adjustable Gastrointestinal Bifurcation (AGB) comprising: (a) a first opening into which food passing through a person's gastrointestinal tract can enter, wherein food that enters this first opening passes through a first food-flow route; (b) a second opening into which food passing through a person's gastrointestinal tract can enter, wherein food that enters this second opening passes through a second food-flow route, and wherein there is less absorption of nutrients from food that passes through the second food-flow route than if the same food were to pass through the first food-flow route; and (c) a flow-control member, wherein this flow-control member is configured to be implanted within the person's body, wherein this flow-control member can post-operatively and reversibly adjust the types and/or amounts of food that are sent into the first opening to pass through the first food-flow route versus the types and/or amounts of food that are sent into the second opening to pass through the second food-flow route, and wherein this flow-control member enables this food flow adjustment to be done in a minimally-invasive or non-invasive manner.

In an example, the first food-flow route can be substantially the same route which food would naturally travel when passing through a portion of an unmodified gastrointestinal tract and absorption of food passing through the first food-flow route is not significantly modified. In an example, the second food-flow route can also be substantially the same route which food would naturally travel when passing a portion of a unmodified gastrointestinal tract, but absorption of food passing through the second food-flow route can be significantly reduced because this food flows through a gastrointestinal sleeve or other absorption-reducing device.

In an example, there can be less absorption of nutrients from food flowing through the second food-flow route than there would be from that food if that food were to flow through the first food-flow route because food passing through the second food-flow route passes through a gastrointestinal sleeve or other artificial gastrointestinal lumen with walls that reduce absorption of food.

In an example, the first food-flow route can be the route which food would naturally travel when passing through a portion of an unmodified gastrointestinal tract; and the second food-flow route can bypasses a portion of the gastrointestinal tract which food would naturally travel. In an example, there can be less absorption of nutrients from food flowing through the second food-flow route than there would be from that food if that food were to flow through the first food-flow route because food passing through the second food-flow route bypasses the person's duodenum or some other portion of the person's gastrointestinal tract.

In an example, the first opening and/or the upstream end of the first food-flow route can be located within the person's esophagus or stomach and the second opening and/or the upstream end of the second food-flow route can be located within the person's esophagus or stomach. In an example, the upstream ends of the first food-flow route and the second food-flow route can form a bifurcation of the person's gastrointestinal tract and the downstream ends of the first food-flow route and the second food-flow route can reconverge at a downstream location in the person's gastrointestinal tract.

In an example, the flow-control member can include a valve selected from the group consisting of: ball valve, balloon valve, butterfly valve, check valve, diaphragm valve, electromechanical valve, flap valve, fluid control valve, hydraulic valve, pneumatic valve, pressure regulator valve, rotating cylinder valve, and solenoid valve. In an example, a flow-control member can comprise: an adjustable valve; an actuator; a central processing unit, an energy source, a wireless transmitter, and a food-consumption sensor.

In an example, a flow-control member can receive information from a food-consumption sensor that is configured to be implanted within, or attached to, one of the following locations within the person's body: the person's mouth, soft palate, tongue, teeth, and/or oral cavity; the person's nose or nasal cavity; and the person's esophagus, stomach, or intestine. In an example, a flow-control member can receive information about the types and/or amount of food that the person is consuming and/or digesting from a food-consumption sensor.

In an example, a flow-control member can receive information about the types and/or amount of food that the person is consuming and/or digesting from a food-consumption sensor that is selected from the group consisting of: chemical sensor, biochemical sensor, accelerometer, amino acid sensor, biological sensor, camera, chemoreceptor, cholesterol sensor, chromatography sensor, EGG sensor, electrolyte sensor, electromagnetic sensor, electronic nose, EMG sensor, enzyme-based sensor, fat sensor, flow sensor, particle size sensor, peristalsis sensor, genetic sensor, glucose sensor, imaging sensor, impedance sensor, infrared sensor, interferometer, medichip, membrane-based sensor, Micro Electrical Mechanical System (MEMS) sensor, microfluidic sensor, micronutrient sensor, molecular sensor, motion sensor, muscle activity sensor, nanoparticle sensor, neural impulse sensor, nutrient sensor, optical sensor, osmolality sensor, pH level sensor, pressure sensor, protein-based sensor, reagent-based sensor, smell sensor, sound sensor, strain gauge, taste sensor, and temperature sensor.

In an example, a flow-control member receives information from a food-consumption sensor that can discriminate between consumption of unhealthy types and/or amounts of food versus healthy types and/or amounts of food. In an example, a flow-control member can receive information from a food-consumption sensor that can detect consumption and/or digestion of unhealthy types of food, wherein unhealthy food is identified as having a large concentration or amount of one or more nutrients selected from the group consisting of: sugars, simple sugars, simple carbohydrates, fats, saturated fats, cholesterol, and sodium. In an example, a flow-control member can use information from a food-consumption sensor to automatically send healthy types and/or amounts of food into the first opening to pass through first food-flow route and to automatically send unhealthy types and/or amounts of food into the second opening to pass through the second food-flow route.

In an example, a flow-control member can use information from a food-consumption sensor to automatically send up to a selected amount of food consumed during a given time period or episode of eating into the first opening to pass through first food-flow route and to automatically send amounts of food consumed over that selected amount during that time period or episode of eating into the second opening to pass through the second food-flow route.

In an example, a flow-control member can communicate wirelessly with a remote control unit that is external to the person's body. In an example, a flow-control member can be wirelessly programmed to adjust one or more of the following aspects of its response to the food-identifying sensor: the type of food which is sent through the first versus second food-flow routes; the quantity of food which is sent through the first versus second food-flow routes; the time of day, day of the week, or other timing parameter wherein food is sent through the first versus second food-flow routes; the effect of the person's past food consumption on the manner in which food is sent through the first versus second food-flow routes; the effect of the person's caloric expenditure on the manner in which food is sent through the first versus second food-flow routes; and the effect of a personalized diet plan created for the person by a health care professional on the manner in which food is sent through the first versus second food-flow routes.

In an example, this invention can be embodied in a device for selectively reducing absorption of nutrients from selected types and/or amounts of food using an Adjustable Gastrointestinal Bifurcation (AGB) comprising: (a) a first opening into which food passing through a person's gastrointestinal tract can enter, wherein food that enters this first opening passes through a first food-flow route; (b) a second opening into which food passing through a person's gastrointestinal tract can enter, wherein food that enters this second opening passes through a second food-flow route, and wherein there is less absorption of nutrients from food that passes through the second food-flow route than if the same food were to pass through the first food-flow route; (c) a food-consumption sensor; and (d) a flow-control member, wherein this flow-control member is configured to be implanted without the person's body, wherein this flow-control member uses information from the food-consumption sensor to automatically send healthy types and/or amounts of food into the first opening to pass through the first food-flow route and to automatically send unhealthy types and/or amounts of food into the second opening to pass through the second food-flow route.

In an example, this invention can be embodied in a method for selectively reducing absorption of nutrients from selected types and/or amounts of food using an Adjustable Gastrointestinal Bifurcation (AGB) comprising: (a) creating a first opening into which food passing through a person's gastrointestinal tract can enter, wherein food that enters this first opening passes through a first food-flow route; (b) creating a second opening into which food passing through a person's gastrointestinal tract can enter, wherein food that enters this second opening passes through a second food-flow route, wherein there is less absorption of nutrients from food that passes through the second food-flow route than if the same food were to pass through the first food-flow route; and (c) using an implanted flow-control member to post-operatively and reversibly adjust the types and/or amounts of food that are sent into the first opening to pass through the first food-flow route versus the types and/or amounts of food that are sent into the second opening to pass through the second food-flow route, wherein this adjustment is done in a minimally-invasive or non-invasive manner.

I claim:

1. A device for adjustably reducing absorption of nutrients from consumed food using an Adjustable Gastrointestinal Bifurcation (AGB) comprising:
   a first opening into which food passing through a person's gastrointestinal tract can enter, wherein food that enters this first opening passes through a first food-flow route;
   a second opening into which food passing through a person's gastrointestinal tract can enter, wherein food that enters this second opening passes through a second food-flow route, and wherein there is less absorption of nutrients from food that passes through the second food-flow route than if the same food were to pass through the first food-flow route, wherein the upstream ends of the first food-flow route and the second food-flow route form a bifurcation of the person's gastrointestinal tract, and wherein downstream ends of the first food-flow route and the second food-flow route reconverge at a downstream location in the person's gastrointestinal tract; and
   a flow-control member, wherein this flow-control member is configured to be implanted within the person's body, wherein this flow-control member can post-operatively and reversibly block the first opening, wherein this flow-control member can post-operatively and reversibly block the second opening, wherein the ability to selectively block the first opening or the second opening at different times enables the flow-control member to post-operatively and reversibly adjust the types and/or amounts of food that are sent into the first opening to pass through the first food-flow route versus the types and/or amounts of food that are sent into the second opening to pass through the second food-flow route, and wherein this flow-control member enables this food flow adjustment to be done in a minimally-invasive or non-invasive manner.

2. The device in claim 1 wherein absorption of food passing through the second food-flow route is significantly reduced because this food flows through a gastrointestinal sleeve or other absorption-reducing device.

3. The device in claim 1 wherein there is less absorption of nutrients from food flowing through the second food-flow route than there would be from that food if that food were to flow through the first food-flow route because food passing through the second food-flow route passes through a gastrointestinal sleeve or other artificial gastrointestinal lumen with walls that reduce absorption of food.

4. The device in claim 1 wherein: the first food-flow route is the route which food would naturally travel when passing through a portion of an unmodified gastrointestinal tract; and the second food-flow route that bypasses a portion of the gastrointestinal tract which food would naturally travel.

5. The device in claim 1 wherein there is less absorption of nutrients from food flowing through the second food-flow route than there would be from that food if that food were to flow through the first food-flow route because food passing through the second food-flow route bypasses the person's duodenum or some other portion of the person's gastrointestinal tract.

6. The device in claim 1 wherein: the first opening and/or the upstream end of the first food-flow route is located within the person's esophagus or stomach; and the second opening and/or the upstream end of the second food-flow route is located within the person's esophagus or stomach.

7. The device in claim 1 wherein the flow-control member includes a valve selected from the group consisting of: ball valve, balloon valve, butterfly valve, check valve, diaphragm valve, electromechanical valve, flap valve, fluid control valve, hydraulic valve, pneumatic valve, pressure regulator valve, rotating cylinder valve, and solenoid valve.

8. The device in claim 1 wherein the flow-control member comprises: an adjustable valve; an actuator; a central processing unit, an energy source, a wireless transmitter, and a food-consumption sensor.

9. The device in claim 1 wherein the flow-control member receives information from a food-consumption sensor that is configured to be implanted within, or attached to, one of the following locations within the person's body: the person's mouth, soft palate, tongue, teeth, and/or oral cavity; the person's nose or nasal cavity; and the person's esophagus, stomach, or intestine.

10. The device in claim 1 wherein the flow-control member receives information about the types and/or amount of food that the person is consuming and/or digesting from a food-consumption sensor.

11. The device in claim 1 wherein the flow-control member receives information about the types and/or amount of food that the person is consuming and/or digesting from a food-consumption sensor that is selected from the group consisting of: chemical sensor, biochemical sensor, accelerometer, amino acid sensor, biological sensor, camera, chemoreceptor, cholesterol sensor, chromatography sensor, EGG sensor, electrolyte sensor, electromagnetic sensor, electronic nose, EMG sensor, enzyme-based sensor, fat sensor, flow sensor, particle size sensor, peristalsis sensor, genetic sensor, glucose sensor, imaging sensor, impedance sensor, infrared sensor, interferometer, medichip, membrane-based sensor, Micro Electrical Mechanical System (MEMS) sensor, microfluidic sensor, micronutrient sensor, molecular sensor, motion sensor, muscle activity sensor, nanoparticle sensor, neural impulse sensor, nutrient sensor, optical sensor, osmolality sensor, pH level sensor, pressure sensor, protein-based sensor, reagent-based sensor, smell sensor, sound sensor, strain gauge, taste sensor, and temperature sensor.

12. The device in claim 1 wherein the flow-control member receives information from a food-consumption sensor that can discriminate between consumption of unhealthy types and/or amounts of food versus healthy types and/or amounts of food.

13. The device in claim 1 wherein the flow-control member receives information from a food-consumption sensor that can detect consumption and/or digestion of unhealthy types of food, wherein unhealthy food is identified as having a large concentration or amount of one or more nutrients selected from the group consisting of: sugars, simple sugars, simple carbohydrates, fats, saturated fats, cholesterol, and sodium.

14. The device in claim 1 wherein the flow-control member uses information from a food-consumption sensor to automatically send healthy types and/or amounts of food into the first opening to pass through first food-flow route and to automatically send unhealthy types and/or amounts of food into the second opening to pass through the second food-flow route.

15. The device in claim 1 wherein the flow-control member uses information from a food-consumption sensor to automatically send up to a selected amount of food consumed during a given time period or episode of eating into the first opening to pass through first food-flow route and to automatically send amounts of food consumed over that selected amount during that time period or episode of eating into the second opening to pass through the second food-flow route.

16. The device in claim 1 wherein the flow-control member can communicate wirelessly with a remote control unit that is external to the person's body.

17. The device in claim 1 wherein the flow-control member can be wirelessly programmed to adjust one or more of the following aspects of its response to the food-identifying sensor: the type of food which is sent through the first versus second food-flow routes; the quantity of food which is sent through the first versus second food-flow routes; the time of day, day of the week, or other timing parameter wherein food is sent through the first versus second food-flow routes; the effect of the person's past food consumption on the manner in which food is sent through the first versus second food-flow routes; the effect of the person's caloric expenditure on the manner in which food is sent through the first versus second food-flow routes; and the effect of a personalized diet plan created for the person by a health care professional on the manner in which food is sent through the first versus second food-flow routes.

18. A device for selectively reducing absorption of nutrients from selected types and/or amounts of food using an Adjustable Gastrointestinal Bifurcation (AGB) comprising:
a first opening into which food passing through a person's gastrointestinal tract can enter, wherein food that enters this first opening passes through a first food-flow route;
a second opening into which food passing through a person's gastrointestinal tract can enter, wherein food that enters this second opening passes through a second food-flow route, and wherein there is less absorption of nutrients from food that passes through the second food-flow route than if the same food were to pass through the first food-flow route, wherein the upstream ends of the first food-flow route and the second food-flow route form a bifurcation of the person's gastrointestinal tract, and wherein downstream ends of the first food-flow route and the second food-flow route reconverge at a downstream location in the person's gastrointestinal tract; and
a food-consumption sensor; and
a flow-control member, wherein this flow-control member is configured to be implanted without the person's body, wherein this flow-control member can post-operatively and reversibly block the first opening, wherein this flow-control member can post-operatively and reversibly block the second opening, and wherein this flow-control member uses information from the food-consumption sensor to automatically send healthy types and/or amounts of food into the first opening to pass through the first food-flow route and to automatically send unhealthy types and/or amounts of food into the second opening to pass through the second food-flow route.

19. A method for selectively reducing absorption of nutrients from selected types and/or amounts of food using an Adjustable Gastrointestinal Bifurcation (AGB) comprising:
creating a first opening into which food passing through a person's gastrointestinal tract can enter, wherein food that enters this first opening passes through a first food-flow route;
creating a second opening into which food passing through a person's gastrointestinal tract can enter, wherein food that enters this second opening passes through a second food-flow route, wherein there is less absorption of nutrients from food that passes through the second food-flow route than if the same food were to pass through the first food-flow route; wherein the upstream ends of the first food-flow route and the second food-flow route form a bifurcation of the person's gastrointestinal tract, and wherein downstream ends of the first food-flow route and the second food-flow route reconverge at a downstream location in the person's gastrointestinal tract; and
using an implanted flow-control member to post-operatively and reversibly block the first opening or block the second opening at different times to adjust the types and/or amounts of food that are sent into the first opening to pass through the first food-flow route versus the types and/or amounts of food that are sent into the second opening to pass through the second food-flow route, wherein this adjustment is done in a minimally-invasive or non-invasive manner.

* * * * *